United States Patent
Shields et al.

(10) Patent No.: US 11,561,224 B2
(45) Date of Patent: Jan. 24, 2023

(54) METHODS FOR PREDICTING RESPONSIVENESS OF A CANCER TO AN IMMUNOTHERAPEUTIC AGENT AND METHODS OF TREATING CANCER

(71) Applicant: BIOVENTURES, LLC, Little Rock, AR (US)

(72) Inventors: Bradley Shields, Little Rock, AR (US); Alan Tackett, Little Rock, AR (US); Stephanie Byrum, Little Rock, AR (US); Fade Mahmoud, Little Rock, AR (US); Sara Shalin, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 294 days.

(21) Appl. No.: 16/483,943

(22) PCT Filed: Feb. 6, 2018

(86) PCT No.: PCT/US2018/017077
§ 371 (c)(1),
(2) Date: Aug. 6, 2019

(87) PCT Pub. No.: WO2018/145095
PCT Pub. Date: Aug. 9, 2018

(65) Prior Publication Data
US 2019/0346446 A1    Nov. 14, 2019

Related U.S. Application Data

(60) Provisional application No. 62/455,209, filed on Feb. 6, 2017.

(51) Int. Cl.
*G01N 33/574* (2006.01)
*A61K 38/45* (2006.01)
*A61K 45/06* (2006.01)

(52) U.S. Cl.
CPC ....... *G01N 33/57423* (2013.01); *A61K 38/45* (2013.01); *G01N 33/5743* (2013.01); *A61K 45/06* (2013.01)

(58) Field of Classification Search
CPC ......... G01N 33/57423; G01N 33/5743; A61K 38/45; A61K 45/06
See application file for complete search history.

(56) References Cited

U.S. PATENT DOCUMENTS

| | | | | |
|---|---|---|---|---|
| 2007/0071675 A1* | 3/2007 | Wu | ............ | C07K 16/2887 424/1.49 |
| 2011/0251216 A1 | 10/2011 | Chinnaiyan | | |
| 2014/0030255 A1* | 1/2014 | Loboda | ............ | C12Q 1/6886 424/133.1 |
| 2015/0301058 A1* | 10/2015 | Schettini | ............ | A61K 39/0011 424/193.1 |
| 2016/0194718 A1* | 7/2016 | Lane | ............ | G01N 33/57492 514/217.01 |
| 2016/0361309 A1 | 12/2016 | McCabe | | |

OTHER PUBLICATIONS

Scott et al., Antibody therapy of cancer, Nature Review Cancer, 12, 278-287 (Year: 2012).*
Atkins, D., et al. "Immunohistochemical detection of EGFR in paraffin-embedded tumor tissues: variation in staining intensity due to choice of fixative and storage time of tissue sections." Journal of Histochemistry & Cytochemistry 52.7 (2004): 893-901.
Atkins, M. B., et al. "High-dose recombinant interleukin 2 therapy for patients with metastatic melanoma: analysis of 270 patients treated between 1985 and 1993." Journal of clinical oncology 17.7 (1999): 2105-2105.
Brown, J. A. et al. Blockade of programmed death-1 ligands on dendritic cells enhances T cell activation and cytokine production. J. Immunol. 170, 1257-66 (2003).
Byrum, S. et al. A quantitative proteomic analysis of FFPE melanoma. J. Cutan. Pathol. 38, 933-936 (2011).
Byrum, S et al. Quantitative Proteomics Identifies Activation of Hallmark Pathways of Cancer in Patient Melanoma. J. Proteomics Bioinform. 6, 43-50 (2013).
Cappuzzo, F., et al. "Epidermal growth factor receptor gene copy number gene mutations and protein level predict outcome to gefitinib therapy in advanced non-small cell lung cancer." J Natl Cancer Inst 97.643 (2005): 643-655.
Chapman, P. B., et al. "Rapid eradication of a bulky melanoma mass with one dose of immunotherapy." New England Journal of Medicine 372.21 (2015): 2073-2074.
Dunn, G. P., et al. The Three Es of Cancer Immunoediting. Annu. Rev. Immunol. 22, 329-360 (2004).
Felip, E., et al. "A phase II pharmacodynamic study of erlotinib in patients with advanced non-small cell lung cancer previously treated with platinum-based chemotherapy." Clinical Cancer Research 14.12 (2008): 3867-3874.
Gori, S., et al. "EGFR, pMAPK, pAkt and PTEN status by immunohistochemistry: correlation with clinical outcome in HER2-positive metastatic breast cancer patients treated with trastuzumab." Annals of oncology 20.4 (2009): 648-654.
Guha, M. "The new era of immune checkpoint inhibitors." Pharmaceutical Journal, Nov. 18, 2014.
Hamid, O. et al. Safety and Tumor Responses with Lambrolizumab (Anti-PD-1) in Melanoma. N. Engl. J. Med. 369, 134-144 (2013).
Hanahan, D. et al. "The hallmarks of cancer." Cell 100.1 (2000): 57-70.

(Continued)

Primary Examiner — Peter J Reddig
Assistant Examiner — Cheng Lu
(74) Attorney, Agent, or Firm — Quarles & Brady LLP

(57) ABSTRACT

The invention generally relates to methods for predicting responsiveness of a cancer to an immunotherapeutic agent and methods of treating cancer. More specifically, the invention relates in part to the use of histone H3 lysine (27) trimethylation (H3K27me3), E-cadherin, and other biomarkers to treat cancer and determine the responsiveness of a cancer tumor to treatment with an immunotherapeutic agent.

8 Claims, 36 Drawing Sheets
Specification includes a Sequence Listing.

(56) References Cited

OTHER PUBLICATIONS

Harlin, H. et al. Chemokine expression in melanoma metastases associated with CD8+ T-cell recruitment. Cancer Res. 69, 3077-85 (2009).

Hirsch, F. R., et al. "Epidermal growth factor receptor immunohistochemistry: Comparison of antibodies and cutoff points to predict benefit from gefitinib in a phase 3 placebo-controlled study in advanced nonsmall-cell lung cancer." Cancer: Interdisciplinary International Journal of the American Cancer Society 112.5 (2008): 1114-1121.

Hirsch, F. R., et al. "Epidermal growth factor receptor in non-small-cell lung carcinomas: correlation between gene copy number and protein expression and impact on prognosis." Journal of clinical oncology 21.20 (2003): 3798-3807.

Hugo, W. et al. Genomic and Transcriptomic Features of Response to Anti-PD-1 Therapy in Metastatic Melanoma. Cell 165, 35-44 (2016).

International Searching Authority. International Search Report and Written Opinion for application PCT/US2018/17077, dated on Jun. 7, 2018. 13 pages.

Ji, R.-R. et al. An immune-active tumor microenvironment favors clinical response to ipilimumab. Cancer Immunol. Immunother. 61, 1019-1031 (2012).

Kreizenbeck, G. M., et al. Prognostic significance of cadherin-based adhesion molecules in cutaneous malignant melanoma. Cancer Epidemiol. Biomarkers Prev. 17, 949-58 (2008).

Lamouille, S., et al. Molecular mechanisms of epithelial-mesenchymal transition. Nat. Rev. Mol. Cell Biol. 15, 178-196 (2014).

Larkin, J. et al. Combined Nivolumab and Ipilimumab or Monotherapy in Untreated Melanoma. N. Engl. J. Med. 373, 23-34 (2015).

Lee, H. J., et al. "Protein overexpression and gene amplification of epidermal growth factor receptor in nonsmall cell lung carcinomas: Comparison of four commercially available antibodies by immunohistochemistry and fluorescence in situ hybridization study." Lung Cancer 68.3 (2010): 375-382.

Lupia, A. et al. CD63 Tetraspanin Is a Negative Driver of Epithelial-to-Mesenchymal Transition in Human Melanoma Cells. J. Invest. Dermatol. 134, 2947-2956 (2014).

Robert, C., et al. "Improved overall survival in melanoma with combined dabrafenib and trametinib." New England Journal of Medicine 372.1 (2015): 30-39.

Robert, C., et al. "Nivolumab in previously untreated melanoma without BRAF mutation." New England journal of medicine 372.4 (2015): 320-330.

Schadendorf, D, et al. Pooled Analysis of Long-Term Survival Data From Phase II and Phase III Trials of Ipilimumab in Unresectable or Metastatic Melanoma. Journal of clinical oncology: official journal of the American Society of Clinical Oncology 33 (2015): 1889-1894.

Schwanhausser, B. et al. Global quantification of mammalian gene expression control. Nature 473, 337-42 (2011).

Schwartzentruber DJ, et al. "Gp100 peptide vaccine and interleukin-2 in patients with advanced melanoma." N Engl j Med 364.22 (2011): 2119-2127.

Sengupta, D. et al. Quantitative Histone Mass Spectrometry Identifies Elevated Histone H3 Lysine 27 (Lys27) Trimethylation in Melanoma. Mol. Cell. Proteomics 15, 765-75 (2016).

Snyder, A. et al. Genetic Basis for Clinical Response to CTLA-4 Blockade in Melanoma. N. Engl. J. Med. 371, 2189-2199 (2014).

Souroullas, G. P. et al. An oncogenic Ezh2 mutation induces tumors through global redistribution of histone 3 lysine 27 trimethylation. Nat. Med. 22, 632-40 (2016).

Spranger, S. et al. "Melanoma-intrinsic β-catenin signalling prevents anti-tumour immunity." Nature 523.7559 (2015): 231-235.

Topalian, S. L. et al. Safety, Activity, and Immune Correlates of Anti-PD-1 Antibody in Cancer. N. Engl. J. Med. 366, 2443-2454 (2012).

Tumeh, P. C. et al. PD-1 blockade induces responses by inhibiting adaptive immune resistance. Nature 515, 568-71 (2014).

Weber, J. "Ipilimumab: controversies in its development, utility and autoimmune adverse events." Cancer immunology, immunotherapy 58.5 (2009): 823.

Wolchok, J. D. et al. Guidelines for the evaluation of immune therapy activity in solid tumors: immune-related response criteria. Clin. Cancer Res. 15, 7412-20 (2009).

Zingg, D. et al. The epigenetic modifier EZH2 controls melanoma growth and metastasis through silencing of distinct tumour suppressors. Nat. Commun. 6, 6051 (2015).

\* cited by examiner

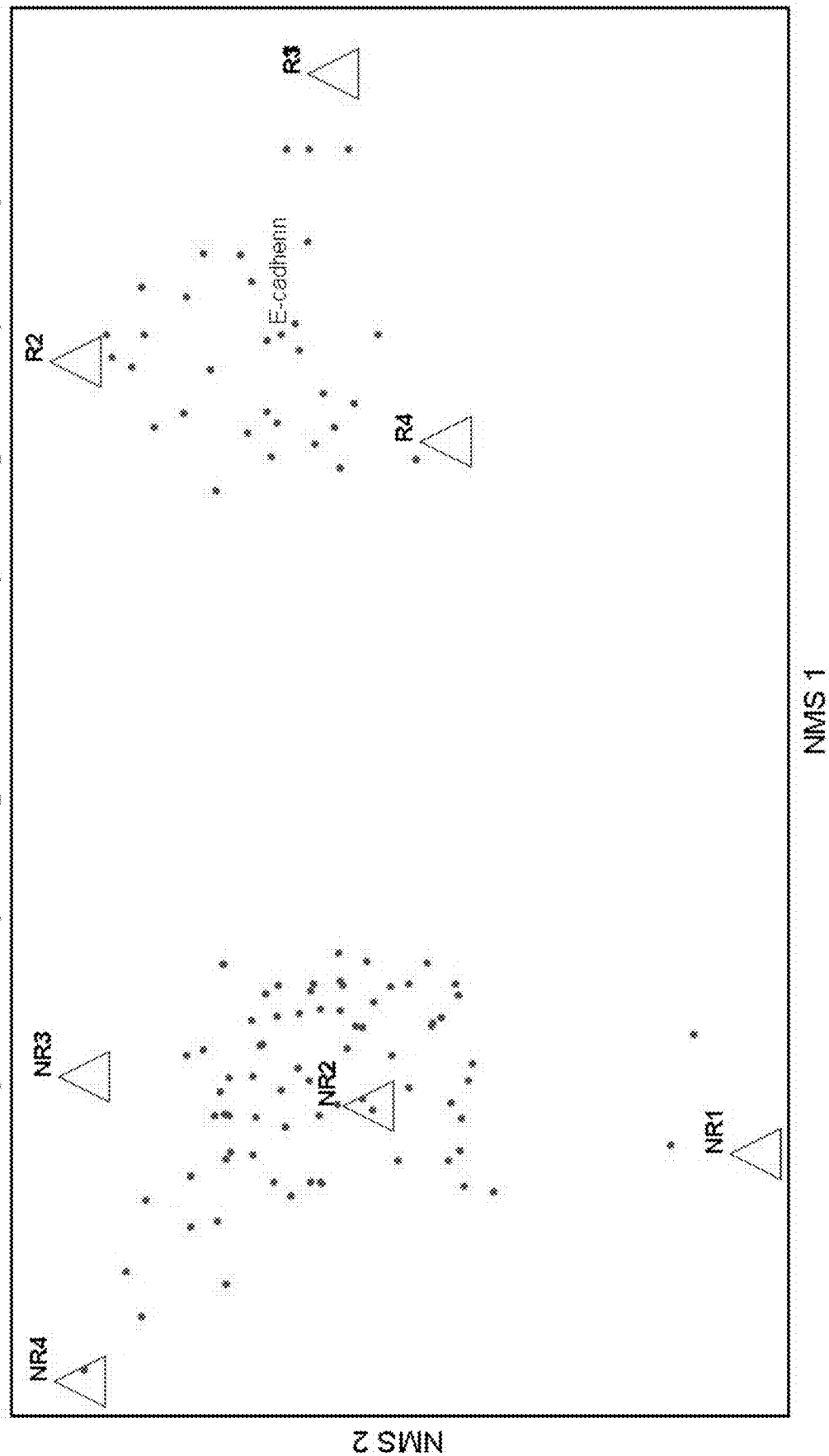

SEQUENCE LISTING

<160> NUMBER OF SEQ ID NOS: 4

<210> SEQ ID NO 1
<211> LENGTH: 20
<212> TYPE: DNA

```
<213> ORGANISM: Artificial Sequence
<220> FEATURE:
<223> OTHER INFORMATION: Synthetic: E-CADHERIN forward

<400> SEQUENCE: 1
agagggtcac cgcgtctatg                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic: E-CADHERIN reverse

<400> SEQUENCE: 2
tcacaggtgc tttgctgttc                                                 20

<210> SEQ ID NO 3
<211> LENGTH: 19
<212> TYPE: DNA
<213> ORGANISM: Artificial Sequence
<220> FEATURE:
<223> OTHER INFORMATION: Synthetic: Beta-actin forward

<400> SEQUENCE: 3
cttggcatcc acgaaacta                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic: Beta-actin reverse

<400> SEQUENCE: 4
gagccagagc agtgatctcc                                                 20
```

METHODS FOR PREDICTING RESPONSIVENESS OF A CANCER TO AN IMMUNOTHERAPEUTIC AGENT AND METHODS OF TREATING CANCER

CROSS-REFERENCE TO RELATED PATENT APPLICATIONS

The present application claims the benefit of priority to U.S. Provisional Patent Application No. 62/455,209, filed on Feb. 6, 2017, the content of which is incorporated herein by reference in its entirety.

STATEMENT REGARDING FEDERALLY SPONSORED RESEARCH

This invention was made with United States government support awarded by the National Institute of Health grant numbers R01GM106024, R21ES025268, and R21DA041822. The United States has certain rights in this invention.

SEQUENCE LISTING

This application is being filed electronically via EFS-Web and includes an electronically submitted Sequence Listing in .txt format. The .txt file contains a sequence listing entitled "2018-02-06_6401-00025_ST25.txt" created on Feb. 6, 2018 and is 1230 bytes in size. The Sequence Listing contained in this .txt file is part of the specification and is hereby incorporated by reference herein in its entirety.

INTRODUCTION

One function of the immune system is to monitor for and eliminate cancerous cells. In accordance, metastatic cancer represents a tumor that has escaped from proper immunosurveillance. Modulation of the immune system can produce anti-tumor responses in various cancer types, including melanoma. Recently, immunotherapeutic agents such as immune checkpoint inhibitors, in single agent and combination regimens, have produced durable and long-lasting clinical responses in a subset of metastatic cancer patients. These therapeutics, developed against CTLA-4 and PD-1, block immune-inhibitory receptors on activated T-cells, amplifying the immune response. However, even when using anti-CTLA-4 and anti-PD-1 therapeutics in combination, approximately half of patients exhibit innate resistance and suffer from disease progression. Currently, it is impossible to predict whether a subject will respond to treatment with immune checkpoint inhibitors and thus there remains a need in the art for new methods of predicting responsiveness of a cancer to an immunotherapeutic agent and new methods of treating cancer that may not be responsive to current immunotherapies.

SUMMARY

In one aspect, methods for predicting the responsiveness of a cancer to an immunotherapeutic agent are provided. The methods may include i) obtaining a tumor sample from a subject and ii) measuring the expression level of at least one biomarker in the tumor sample. The biomarker may be any one of those listed in Table 1 or H3K27me3.

In another aspect, methods of treating cancer in a subject are also provided. The methods of treating cancer in a subject may include administering to the subject a therapeutically effective amount of an immunotherapeutic agent based on the expression level of at least one biomarker in a tumor sample from the subject. The biomarker may be selected from the group consisting of any one of the biomarkers listed in Table 1 or H3K27me3.

In a further aspect, the methods of treating cancer in a subject may include administering to the subject a therapeutically effective amount of an EZH2 methyltransferase inhibitor based on the expression level of at least one biomarker in a tumor sample from the subject. The biomarkers may be selected from the group consisting of the biomarkers listed in Table 1 and H3K27me3.

In a still further aspect, the methods of treating cancer in a subject may include administering a therapeutically effective amount of an EZH2 methyltransferase inhibitor to the subject, and administering a therapeutically effective amount of an immunotherapeutic agent to the subject.

BRIEF DESCRIPTION OF DRAWINGS

(FIGS. 1A, 1C) Representative CD8+ and CD3+ IHC staining of the invasive tumor margin and intratumoral region in pretreatment metastatic melanoma tumors (responding n=4, non-responding n=4). Tumor compartments were demarcated by a dermatopathologist. (FIGS. 1B, 1D) Average CD8+ and CD3+ cell counts for responding and non-responding tumors' compartments. T-cell counts were generated by averaging the counts of 10 randomly selected fields at 20× objective for each tumor compartment (10 invasive margin; 10 intratumoral). Individual tumor counts can be found in FIGS. 5A-5D. RIM=Responding invasive margin; NRIM=Non-responding invasive margin; RIT=Responding intratumoral; NRIT=Non-responding intratumoral. (FIG. 1E) Reverse western assay with the human chemokine antibody arrays (R&D Systems). Results are ratios of summed intensities of responding and non-responding tumors, ratios >2 were defined as a significant change. Chemokine signaling was higher in responding tumors with 10 of 31 chemokines showing >2 fold change. All error bars denote the s.e.m.

FIGS. 2A-2D show a proteomics analysis of metastatic melanoma lesions from ICI therapy non-responders and responders identified mis-regulated proteins. (FIG. 2A) Isolation of proteins from metastatic melanoma lesions from ICI therapy responders and non-responders. Venn diagram of total protein IDs from the ICI patient dataset. (FIG. 2B) Volcano plot of significantly differentiating proteins between responding and non-responding tumors. The negative log (base 10) of the p-values is plotted on the y-axis and the log (base 2) of the fold change is plotted on the x-axis. The blue data points indicate proteins with a p-value <0.05 and a fold change >2. (FIG. 2C) An unsupervised hierarchical clustering of all 8 patients and the 106 proteins with significant changes in abundance clearly separated the responding and non-responding tumors. Blue data points indicate lower protein abundance and a red color indicates elevated abundance. (FIG. 2D) Non-metric multidimensional scaling (NMS) ordination of responding and non-responding tumor protein profiles. Patients (triangles) clearly clustered into groups by response status using protein abundance data (red dots) (R=responding; NR=non-responding). The protein E-cadherin (CDH1) was highly correlated with NMS axis 1 and was selected for further studies. NMS axes 1 and 2 are mathematical expressions which represent the specific ordination (placement of the patients based upon protein abundance data) which resulted in the minimal amount of stress between the patients.

(FIG. 3A) Ingenuity pathway analysis protein abundance values revealed enriched pathways in non-responding tumors. (FIG. 3B) Network map generated by IPA of top pathways, depicting a subset of proteins involved in EMT. Red proteins indicated down-regulation in non-responding tumors, while green indicates up-regulation in non-responding tumors, compared to protein levels in responding tumors. Canonical Pathway tags (CP) show solid lines to proteins which represent biological interactions of select proteins contributing to EMT. (FIG. 3C) Levels of proteins implicated in EMT and chemokines (by gene name) differentially expressed between the responding versus non-responding pre-treatment tumors. (FIG. 3D) Proteomic iBAQ scores for EMT proteins and chemokines. (FIGS. 3E-3F) Immunohistochemical staining for E-cadherin (FIG. 3E) and CD63 (FIG. 3F) confirmed reduced expression in non-responding tumors. Each image is shown at 20× magnification. Compiled H-score of IHC slides is shown below the histologic images. n=4 for responding and non-responding tumors. E-cadherin loss is a central event in EMT, while CD63 has been shown to be a negative driver of EMT in melanoma (*p<0.05).

(FIG. 4A) Quantitative analysis of histone peptide intensities revealed H3K27me3 was elevated in non-responding tumors relative to responding tumors. Standard error was calculated for the specific peptide in the biological replicate samples as displayed in the chart. n=4 for responding and non-responding tumors (*P<0.05). (FIG. 4B) Immunoblot analyses of tumor cell extracts showed elevated H3K27me3 in non-responding tumors. Histone H3 was used as the loading control. Immunoblot quantitation and statistical analysis using ImageJ software and Student's T test (*P<0.05). (FIG. 4C) ChIP-qPCR performed on FFPE tumor samples with Histone H3 and H3K27me3-specific antibodies followed by qPCR analysis showed significant fold enrichment of H3K27me3 (P=0.01) at E-cadherin promoter relative to the β-ACTIN promoter, in ICI therapy responding versus non-responding tumors. (FIG. 4D) Overall survival of anti-PD-1-treated patients whose melanoma tumors harbored high (top half) versus low (bottom half) E-cadherin transcripts; p values, log-rank test. (FIG. 4E) Response designation of anti-PD-1-treated patients whose melanoma tumors harbored high (top half) versus low (bottom half) E-cadherin transcripts. CR=complete response, PR=partial response, PD=progressive disease, according to irRECIST. Error bars denote the s.e.m.

(FIGS. 5A, 5C) Average invasive margin CD8+ and CD3+ cell counts across 10 fields at 20× objective. Each dot represents one field count. (FIGS. 5B, 5D) Average intratumoral CD8+ and CD3+ cell counts across 10 fields at 20× objective. Each dot represents one field count. Error bars denote the maximum and minimum values; horizontal bars denote the mean.

DETAILED DESCRIPTION

Figure 1B:
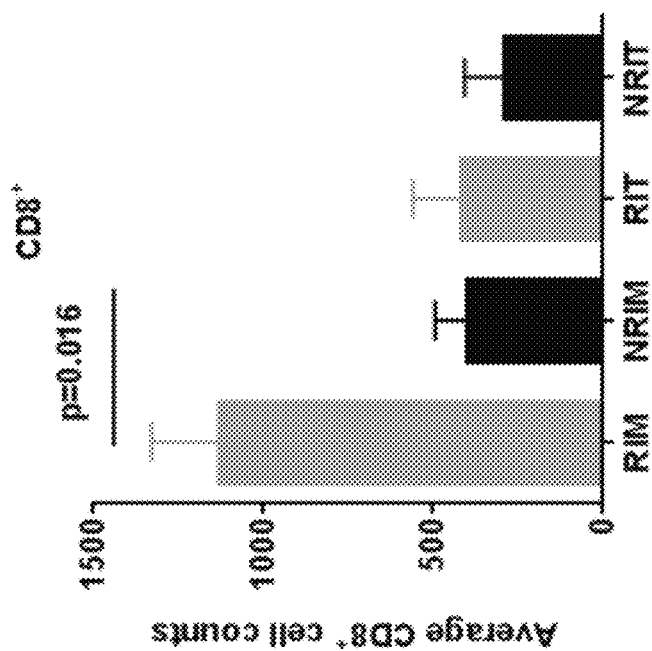
FIGS. 1A-1E show that responding tumors show increased T-cells and Chemokines prior to treatment.

Here, the present inventors identify putative biomarkers indicating the responsiveness of a cancer tumor to treatment with an immunotherapeutic agent, and the first evidence of epigenetically-driven epithelial-mesenchymal transition, a known mechanism of immune-escape, in non-responding tumors such as melanoma tumors. Using high-resolution proteomics, the present inventors identified elevated histone H3 lysine (27) trimethylation (H3K27me3), decreased E-cadherin, and other protein biomarkers (See, e.g., Table 1) indicating a more mesenchymal phenotype in non-responding tumors. Furthermore, we show E-cadherin is transcriptionally regulated by the EZH2-catalyzed H3K27me3 epigenetic mark in non-responding tumors. The repressive epigenetic mark H3K27me3, has known roles in melanoma pathogenesis and progression, but not in response to immunotherapies. Thus, the inventors provide the first report of an epigenetic program directly linking elevated levels of H3K27me3 to non-responding tumors. These results further demonstrate how epigenetic modulating agents such as EZH2 inhibitors may be used to restore a more epithelial phenotype, and influence immune checkpoint inhibitor responsiveness in cancer tumors.

Methods for predicting the responsiveness of a cancer to an immunotherapeutic agent are provided. The methods may include i) obtaining a tumor sample from a subject and ii) measuring the expression level of at least one biomarker selected from the biomarkers listed Table 1 or H3K27me3 in the tumor sample.

As used herein, a "tumor sample" is a sample containing at least one cell taken from or around a cancer tumor by, for example, a biopsy or obtained after a tumor is removed from the subject. In accordance with the present methods, the cancer may be any cancer including, without limitation, melanoma, carcinoma, epithelial, breast, colorectal, pancreatic, liver, esophageal, gastric, kidney, small bowel, cholangiocarcinoma, lung (such as non-small cell lung cancer), head and neck, thyroid, renal, bladder, ovarian, cervical, uterine, prostate, lymphomas, leukemias, neuroendocrine, glioblastoma or any other form of brain cancer. Suitably, the cancer is a melanoma, carcinoma, lung cancer (such as non-small cell lung cancer), bladder cancer, or an epithelial cancer and the tumor sample is from a melanoma tumor, carcinoma tumor, lung cancer tumor, bladder cancer tumor, or an epithelial cancer tumor.

The terms "subject" and "patient" are used interchangeably herein and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. Preferably, the subject is a human patient. More preferably, the subject is a human patient diagnosed with cancer.

As used herein, a "biomarker" is a protein or polynucleotide whose level of expression in a sample is indicative of a condition. In the Examples, the biomarkers are measured by assessing the expression levels of proteins encoded by genes expressed in cells of a tumor sample. In some embodiments, the expression level of the biomarker is the protein expression level. In some embodiments, the expression level of the biomarker is the mRNA expression level. These expression levels have, for example, been found to correlate with the responsiveness of a cancer to an immunotherapeutic agent. Biomarker expression in some instances may be normalized against the expression levels of all proteins or RNA transcripts in the sample, or against a reference set of proteins or RNA transcripts in the sample.

Fragments and variants of biomarker mRNA transcripts and proteins are also encompassed by the present invention. A "fragment" is intended to refer to a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of biomarker polypeptides will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs.

Any methods available in the art for detecting expression of biomarkers are encompassed herein. The expression of a biomarker of the invention can be detected on a polynucleotide level (e.g., as an mRNA transcript) or a protein level. "Measuring the expression level" means determining the quantity or presence of a protein or its RNA transcript for at least one of the biomarkers disclosed herein. Thus, "measuring the expression level" encompasses instances where a biomarker is determined not to be expressed, not to be detectably expressed, expressed at a low level, expressed at a normal level, or overexpressed. As discussed further below, the expression level may be measured relative to a reference level of the biomarker or a control.

Methods suitable for measuring, detecting, or determining the expression levels of protein biomarkers are known to those of skill in the art and include, but are not limited to, mass spectrometry, ELISA, immunofluorescence, FACS analysis, Western blot, magnetic immunoassays, both antibody-based microarrays and non-antibody-based microarrays, and other antibody-based methods. In the past, the gold standard for detection of protein biomarkers was the use of ELISAs; however, mass spectrometry offers an attractive alternative approach for protein biomarker analysis.

Several multiplex platforms also currently exist and may be used for measuring, detecting, or determining the expression levels of protein biomarkers. The Luminex bead-based systems are the most established, being used to detect protein biomarkers in both mice and humans. This method is based on the use of microparticles that have been pre-coated with specific antibodies. These particles are then mixed with sample and the captured analytes are detected using specific secondary antibodies. This allows for up to 100 different analytes to be measured simultaneously in a single microplate well. The advantages of this flow cytometry-based method compared to traditional ELISA assays are in the conservation of patient samples as well as significant savings in terms of cost and labor. An alternative, plate-based system is produced by Meso Scale Discovery (MSD). This system utilizes its proprietary Multi-Array® and Multi-Spot® microplates with electrodes directly integrated into the plates. This enables the MSD system to have ultra-sensitive detection limits, high specificity, and low background signal. Another plate-based multiplex system is the SearchLight Plus CCD Imaging System produced by Aushon Biosystems. This novel multiplexing technology allows for the measurement of up to 16 different analytes simultaneously in a single microplate well. The assay design is similar to a sandwich ELISA where the capture antibodies are pre-spotted into individual wells of a 96-well plate. Samples or standards are added which bind to the specific capture antibodies and are detected using Aushon's patented SuperSignal ELISA Femto Chemiluminescent Substrate.

Methods for detecting expression of the biomarkers described herein are not limited to protein expression. Gene expression profiling including methods based on hybridization analysis of polynucleotides, methods based on sequencing of polynucleotides, immunohistochemistry methods, and proteomics-based methods may also be used. The most commonly used methods known in the art for the quantification of mRNA expression in a sample include northern blotting and in situ hybridization (Parker and Barnes, Methods Mol. Biol. 106:247-83, 1999), RNAse protection assays (Hod, Biotechniques 13:852-54, 1992), PCR-based methods, such as reverse transcription PCR (RT-PCR) (Weis et al., TIG 8:263-64, 1992), including real time quantitative PCR and array-based methods (Schena et al., Science 270: 467-70, 1995). Alternatively, antibodies may be employed that can recognize specific duplexes, including DNA duplexes, RNA duplexes, and DNA-RNA hybrid duplexes, or DNA-protein duplexes. Representative methods for sequencing-based gene expression analysis include Serial Analysis of Gene Expression (SAGE) and gene expression analysis by massively parallel signature sequencing.

In the methods described herein the expression level of the disclosed biomarkers in the tumor sample from the subject are determined using any one of the detection methods described herein. Then the level in the tumor sample from the subject is compared to a reference level of the biomarker or a control. The "reference level" may be determined empirically such as it was in the Examples, by the relative comparison of the levels found in a set of samples from cancer patients that responded to the administered immunotherapeutic agent (i.e., responders) to the levels found in a set of samples from cancer patients that did not respond to the administered immunotherapeutic agent (i.e., non-responders). Alternatively, the reference level may be a level of the biomarker found in tumor samples which becomes a standard and can be used as a predictor for new samples.

In accordance with the present invention, the biomarkers measured in the tumor sample may include at least 1, 2, 3, 4, 5, 6, 7, 8, 9, 10, or more of the biomarkers listed Table 1 and/or H3K27me3. The biomarkers measured in the tumor sample may include at least 1, 2, 3, 4, 5, 6, 7, 8, 9, 10, or all of biomarkers selected from the group consisting of CDH1, CD63, CXCL4, MYLK, CXCL12, PIGR, ILK, TPM2, CREB1, LIMS1, and H3K27me3. In some embodiments, the biomarkers include CDH1, H3K27me3, or both. In some embodiments, the expression levels of no more than 10, 12, 15, 18, 20, 25, 30, or 40 biomarkers are measured.

The methods disclosed herein may further include administering a therapeutically effective amount of an EZH2 methyltransferase inhibitor to the subject following the measurement of the expression levels of the biomarkers. In part, the present inventors discovered increased expression levels of H3K27me3 in non-responding tumor levels. Based on this discovery, the inventors predict that administering an EZH2 methyltransferase inhibitor to a subject with a non-responding tumor may increase the responsiveness of the subject's cancer and/or tumor to an immunotherapeutic agent.

As used herein, an "EZH2 methyltransferase inhibitor" is any agent capable of partially or fully inhibiting one or more of the biological activities of an EZH2 methyltransferase protein including, without limitation, a polypeptide, a polynucleotide, or a small molecule. An EZH2 methyltransferase inhibitor may function in a direct or indirect manner. For example, the EZH2 methyltransferase inhibitor may directly bind to an EZH2 methyltransferase protein, thus partially or fully inhibiting one or more biological activities of an EZH2 methyltransferase protein, in vitro or in vivo. The EZH2 methyltransferase inhibitor may also function indirectly by (1) interacting with (e.g., activating, inducing, blocking or inhibiting) another molecule that can bind to an EZH2 methyltransferase protein or (2) modulating or affecting the expression (i.e, transcription or translation) of an EZH2 methyltransferase protein in a cell.

Using a S-adenosyl-L-methionine cofactor, mammalian EZH2 methyltransferase proteins catalyze the addition of methyl groups to histone H3 at lysine 27. The trimethylation of lysine 27 of histone H3 has been shown to facilitate heterochromatin formation and transcriptional repression.

EZH2 methyltransferase proteins may be any of the EZH2 methyltransferase proteins found in any mammal including, without limitation, humans or domesticated animals such as dogs, cats, horses, cows, pigs, mice, or rats. Suitably, the EZH2 methyltransferase inhibitors disclosed herein inhibit the human EZH2 methyltransferase protein.

The EZH2 methyltransferase inhibitor may be a polypeptide including, without limitation, a peptide or an antibody. As used herein, the term "antibody" is used in the broadest sense used in the art to refer to polypeptide affinity agents based on antibodies. For example, the antibody may include a polyclonal antibody, a monoclonal antibody, a single chain antibody, or antibody fragments such as Fab, Fab', F(ab')$_2$, Fv fragments, diabodies, linear antibodies, or multispecific antibodies formed from antibody fragments. The antibody may be chimeric, humanized, or fully human. The antibody may be any one of the five known major classes of immunoglobulins including IgA, IgD, IgE, IgG, and IgM. In some embodiments, the EZH2 methyltransferase inhibitor may be an antibody that is capable of binding an EZH2 methyltransferase protein and thereby partially or fully inhibiting one or more of the biological activities of the EZH2 methyltransferase protein.

Peptides useful as EZH2 methyltransferase inhibitors may be identified using techniques well-known in the art such as phage display.

Aptamers are polynucleotides (e.g., ssDNA or ssRNA) that bind to a specific target molecule. In some embodiments, the EZH2 methyltransferase inhibitor may be an aptamer that is capable of binding an EZH2 methyltransferase protein and thereby partially or fully inhibiting one or more of the biological activities of the EZH2 methyltransferase protein.

The EZH2 methyltransferase inhibitor may be a small molecule including, without limitation, EPZ-6438, GSK-126, DZNep, El1, EPZ005687, GSK-343, and UNC-1999. The small molecule may be a chemical molecule having a molecular weight below about 2500 Daltons, 2000 Daltons, 1000 Daltons, or 500 Daltons.

In some embodiments, the EZH2 methyltransferase inhibitor is administered to the subject if the expression of the biomarker(s) is/are altered as indicated in the "Fold-Change" of Table 1 to predict that the subject is a non-responder. For example, row 1 of Table 1 indicates that CDH1 expression levels were decreased in non-responding tumors as compared to responding tumors by greater than 2-fold. See, e.g., "FoldChange" column of Table 1 indicating that CDH1 was expressed 3.897 fold lower in non-responding tumors as compared to responding tumors. Thus, if the expression level of CDH1 is measured in a new tumor sample and the expression level is decreased compared to the levels measured in responding tumors by greater than 2-fold, the tumor sample may be characterized as a non-responder and the subject may benefit from administration of an EZH2 methyltransferase inhibitor.

The methods disclosed herein may further include administering a therapeutically effective amount of an immunotherapeutic agent to the subject following the measurement of the expression levels of the biomarkers. In part, the present inventors discovered that the expression levels of the biomarkers (either alone or in combination) in Table 1 and H3K27me3 could be used to determine whether a tumor sample would be responsive to treatment with an immunotherapeutic agent. If a tumor sample is found to be a responder then the subject may benefit from the administration of an immunotherapeutic agent.

As used herein, an "immunotherapeutic agent" is refers to any therapeutic that is used to treat cancer in a subject by inducing and/or enhancing an immune response in that subject. Immunotherapeutic agents may include, without limitation, checkpoint inhibitors. Checkpoint inhibitors are therapeutics, such as antibodies, that block the immune checkpoint pathways in immune cells that are responsible for maintaining self-tolerance and modulating the degree of an immune response. Tumors often exploit certain immune checkpoint pathways as a major mechanism of immune resistance against T cells that are specific for tumor antigens. Many of the immune checkpoints are initiated by receptor-ligand interactions and thus may be blocked by antibodies to either the ligand or receptor or may be modulated by soluble recombinant forms of the ligands or receptors. Such immune checkpoint blockade allows tumor-specific T cells to continue to function in an otherwise immunosuppressive tumor microenvironment.

Exemplary checkpoint inhibitors that may be used in accordance with the present invention include, without limitation, antibodies or other therapeutics targeting programmed cell death protein 1 (PD1, also known as CD279), programmed cell death 1 ligand 1 (PD-L1, also known as CD274), PD-L2, cytotoxic T-lymphocyte antigen 4 (CTLA4, also known as CD152), A2AR, CD27, CD28, CD40, CD80, CD86, CD122, CD137, OX40, GITR, ICOS, TIM-3, LAG3, B7-H3, B7-H4, BTLA, IDO, KIR, or VISTA. Suitable anti-PD1 antibodies include, without limitation, lambrolizumab (Merck MK-3475), nivolumab (Bristol-Myers Squibb BMS-936558), AMP-224 (Merck), and pidilizumab (CureTech CT-011). Suitable anti-PD-L1 antibodies include, without limitation, MDX-1105 (Medarex), MEDI4736 (Medimmune) MPDL3280A (Genentech/Roche) and BMS-936559 (Bristol-Myers Squibb). Exemplary anti-CTLA4 antibodies include, without limitation, ipilimumab (Bristol-Myers Squibb) and tremelimumab (Pfizer).

In some embodiments of the present methods, the EZH2 methyltransferase inhibitor may be administered prior to, concurrently, or after the immunotherapeutic agent. Preferably, to increase the responsiveness of a subject's cancer and/or tumor to the immunotherapeutic agent, the EZH2 methyltransferase inhibitor may be administered prior to the immunotherapeutic agent by at least 6 hours, 12 hours, 1 days, 2 days, 3 days, 5 days, 1 week, or more.

In some embodiments, the immunotherapeutic agent is administered to the subject if the expression of the biomarker(s) is/are altered as indicated in the "FoldChange" column of Table 1 to predict that the subject is a responder. For example, row 1 of Table 1 indicates that CDH1 expression levels were increased in responding tumors as compared to non-responding tumors by greater than 2-fold. See, e.g., the "FoldChange" column of Table 1 indicating that CDH1 was expressed 3.897 fold higher in responding tumors as compared to non-responding tumors. Thus, if the expression level of CDH1 is measured in a new tumor sample and the expression level is increased compared to the levels measured in non-responding tumors by greater than 2-fold, the tumor sample may be considered a responding tumor and the subject may benefit from administration of the immunotherapeutic agent. In a similar manner, the expression level differences for each of the biomarkers listed in Table 1 may be used to determine whether a subject should be administered an immunotherapeutic agent. As discussed above, patients with tumors characterized as non-responding or even potentially non-responding in the assays described herein may be administered an immunotherapeutic agent (a checkpoint inhibitor) and an EZH2 methyltransferase inhibitor in combination.

Methods of treating cancer in a subject are also provided. The methods of treating cancer in a subject may include administering to the subject a therapeutically effective amount of an immunotherapeutic agent based on the expression level of at least one biomarker in a tumor sample from the subject selected from the group consisting of any one of the biomarkers listed Table 1, H3K27me3, and any of the biomarkers described herein, either individually or in combination.

The methods of treating cancer in a subject may include administering to the subject a therapeutically effective amount of an EZH2 methyltransferase inhibitor based on the expression level of at least one biomarker in a tumor sample from the subject selected from the group consisting of any one of the biomarkers listed Table 1, H3K27me3, and any of the biomarkers described herein, either individually or in combination.

The methods of treating cancer in a subject may include administering a therapeutically effective amount of an EZH2 methyltransferase inhibitor to the subject, and administering a therapeutically effective amount of an immunotherapeutic agent to the subject. The EZH2 methyltransferase inhibitor may be administered before, after, or concurrently with the immunotherapeutic agent. Preferably, to increase the responsiveness of a subject's cancer and/or tumor to the immunotherapeutic agent, the EZH2 methyltransferase inhibitor may be administered prior to the immunotherapeutic agent by at least 6 hours, 12 hours, 1 days, 2 days, 3 days, 5 days, 1 week, or more.

"Treating cancer" includes, without limitation, reducing the number of cancer cells or the size of a tumor in the subject, reducing progression of a cancer to a more aggressive form (i.e. maintaining the cancer in a form that is susceptible to a therapeutic agent), reducing proliferation of cancer cells or reducing the speed of tumor growth, killing of cancer cells, reducing metastasis of cancer cells or reducing the likelihood of recurrence of a cancer in a subject. Treating a subject as used herein refers to any type of treatment that imparts a benefit to a subject afflicted with cancer or at risk of developing cancer or facing a cancer recurrence. Treatment includes improvement in the condition of the subject (e.g., in one or more symptoms), delay in the progression of the disease, delay in the onset of symptoms or slowing the progression of symptoms, etc.

As used herein, a "therapeutically effective amount" or an "effective amount" means the amount of a composition that, when administered to a subject for treating a state, disorder or condition is sufficient to effect a treatment (as defined above). The therapeutically effective amount will vary depending on the compound, formulation or composition, the disease and its severity and the age, weight, physical condition and responsiveness of the subject to be treated.

The EZH2 methyltransferase inhibitors and/or immunotherapeutic agents described herein may be administered by any means known to those skilled in the art, including, without limitation, intravenously, orally, intra-tumoral, intra-lesional, intradermal, topical, intraperitoneal, intramuscular, parenteral, subcutaneous and topical administration Thus the compositions may be formulated as an injectable, topical, ingestible, or suppository formulation. Administration of the EZH2 methyltransferase inhibitors and/or immunotherapeutic agents to a subject in accordance with the present invention may exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage of EZH2 methyltransferase inhibitors and/or immunotherapeutic agents administered in any given case will be adjusted in accordance with the composition or compositions being administered, the volume of the composition that can be effectively delivered to the site of administration, the disease to be treated or inhibited, the condition of the subject, and other relevant medical factors that may modify the activity of the compositions or the response of the subject, as is well known by those skilled in the art. For example, the specific dose of an EZH2 methyltransferase inhibitor and/or immunotherapeutic agent for a particular subject depends on age, body weight, general state of health, diet, the timing and mode of administration, the rate of excretion, medicaments used in combination and the severity of the particular disorder to which the therapy is applied. Dosages for a given patient can be determined using conventional considerations, e.g., by customary comparison of the differential activities of the compositions described herein and of a known agent, such as by means of an appropriate conventional pharmacological protocol. The compositions can be given in a single dose schedule, or in a multiple dose schedule.

The maximal dosage of an EZH2 methyltransferase inhibitor and/or immunotherapeutic agent for a subject is the highest dosage that does not cause undesirable or intolerable side effects. The number of variables in regard to an individual treatment regimen is large, and a considerable range of doses is expected. The route of administration will also impact the dosage requirements. It is anticipated that dosages of the compositions will treat cancer by, for example, by reducing tumor size or decreasing the rate of tumor growth by least 10%, 20%, 30%, 40%, 50%, 60%, 70%, 80%, 90%, 100% or more as compared to no treatment.

The effective dosage amounts of an EZH2 methyltransferase inhibitor and/or immunotherapeutic agent refers to total amounts administered, that is, if more than one composition is administered, the effective dosage amounts of an EZH2 methyltransferase inhibitor and/or immunotherapeutic agent corresponds to the total amount administered. The compositions can be administered as a single dose or as divided doses. For example, the composition may be administered two or more times separated by 4 hours, 6 hours, 8 hours, 12 hours, a day, two days, three days, four days, one week, two weeks, or by three or more weeks.

Suitable dosage ranges for an EZH2 methyltransferase inhibitor and/or immunotherapeutic agent may be of the order of several hundred micrograms of the agent with a range from about 0.001 to 10 mg/kg/day, preferably in the range from about 0.01 to 1 mg/kg/day. Precise amounts of an EZH2 methyltransferase inhibitor and/or immunotherapeutic agent required to be administered depend on the judgment of the practitioner and may be peculiar to each subject. It will be apparent to those of skill in the art that the therapeutically effective amount of the compositions and pharmaceutical compositions described herein will depend, inter alia, upon the administration schedule, the unit dose of agent administered, whether the composition is administered in combination with other therapeutic agents, the status and health of the recipient, and the therapeutic activity of the particular composition.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Example 1—Proteomic and Epigenetic Markers of Responsiveness to Immune Checkpoint Inhibitors in Melanoma One function of the immune system is to monitor for and eliminate cancerous cells. In accordance, metastatic disease represents a tumor that has escaped from proper immunosurveillance[1]. Modulation of the immune system can produce anti-tumor responses in various cancer types, including melanoma. Recently, immune checkpoint inhibitors, in single agent and combination regimens, have produced durable and long-lasting clinical responses in a subset of metastatic melanoma patients[2-4]. These monoclonal antibodies, developed against CTLA-4 and PD-1, block immune-inhibitory receptors on activated T-cells, amplifying the immune response[5-6]. However, even when using anti-CTLA-4 and anti-PD-1 in combination, approximately half of patients exhibit innate resistance and suffer from disease progression[7]. Currently, it is impossible to predict therapeutic response. Here we show putative biomarkers of responsiveness, and the first evidence of epigenetically-driven epithelial-mesenchymal transition, a known mechanism of immune-escape, in non-responding melanoma tumors. Using high-resolution proteomics, we identified elevated histone H3 lysine (27) trimethylation (H3K27me3), decreased E-cadherin, and other protein features indicating a more mesenchymal phenotype in non-responding tumors. Furthermore, we show E-cadherin is transcriptionally regulated by the EZH2-catalyzed H3K27me3 epigenetic mark in non-responding tumors. The repressive epigenetic mark H3K27me3, has known roles in melanoma pathogenesis and progression, but not in response to immunotherapies[8,9]. Here, we provide the first report of an epigenetic program directly linking elevated levels of H3K27me3 to non-responding tumors. Our results demonstrate how epigenetic modulating agents might be used to restore a more epithelial phenotype, perhaps influencing immune checkpoint inhibitor responsiveness in certain melanoma tumors.

As immune checkpoint inhibitors (ICIs) become foundational in the immunotherapeutic armamentarium, the question still remains: why do some patients respond, while other patients experience disease progression? Immune checkpoint blockade, when effective, can result in durable and long lasting clinical benefits[4]. However, response rates for monotherapies with ICIs range from 19% for anti-CTLA-4 to 43.7% for anti-PD-17. Combination therapy with anti-CTLA-4 and anti-PD1 has achieved a response rate of 57.6% and has become the standard of care for advanced melanoma cases[7]. Despite the advent of these therapies, approximately half of patients with advanced melanoma do not respond to treatment.

Recent studies have been aimed at addressing the question of responsiveness to immune checkpoint blockade in melanoma tumors. Genomic and transcriptomic analyses have been performed on both anti-CTLA-4 and anti-PD-1 pretreatment tumor samples. Response to anti-CTLA-4 therapy has been associated with a tetrapeptide signature, overall mutational load, and cytolytic markers through whole exome sequencing of pre-treatment tumors[10,11]. Intrinsic resistance to anti-PD-1 therapy has been found to correlate with increased expression of genes involved in mesenchymal transition, extracellular matrix remodeling, angiogenesis, and wound healing. Hugo and colleagues termed this transcriptional signature "IPRES" or innate anti-PD-1 resistance[12]. Additionally, evidence suggests patients whose T-cells have previously mounted an anti-tumor response achieve more therapeutic benefit from checkpoint blockade therapies[13]. Despite this progress, characterization of tumor phenotypes which display innate resistance to checkpoint blockade is still largely incomplete and unexplored. Here, we sought to identify putative protein and epigenetic markers differentiating melanomas responsive or unresponsive to ICI therapy for patient stratification and potential therapeutic targeting to elicit immune responses against tumors which demonstrate innate resistance to checkpoint blockade.

Figure 1A:
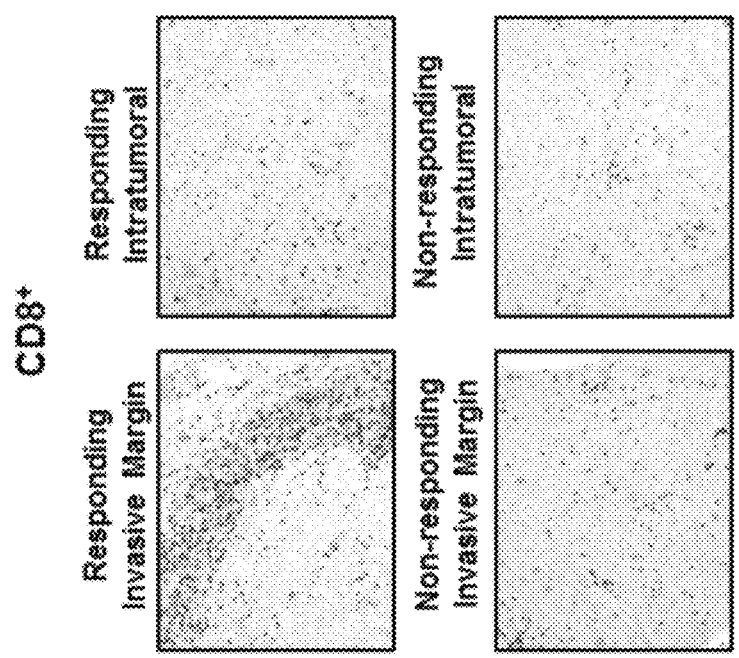
Figure 1C:
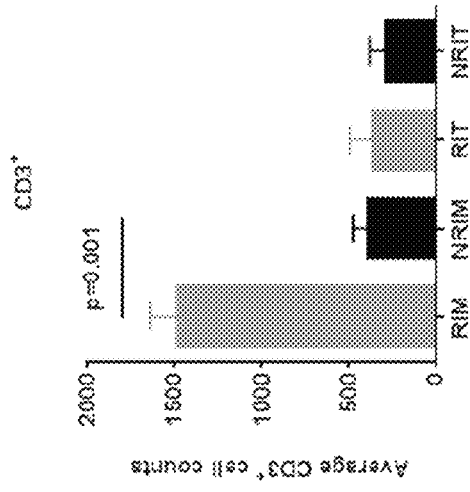
Figure 1D:
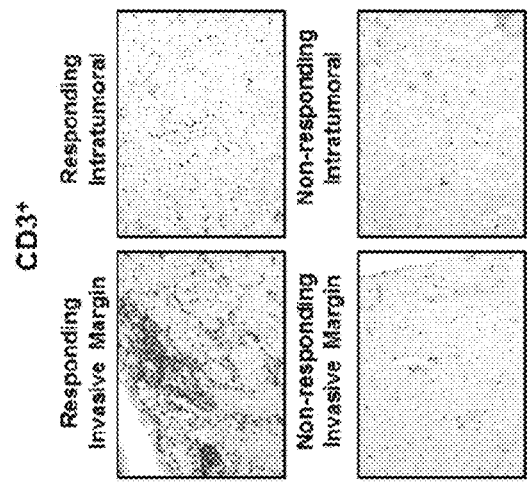
Figure 1E:
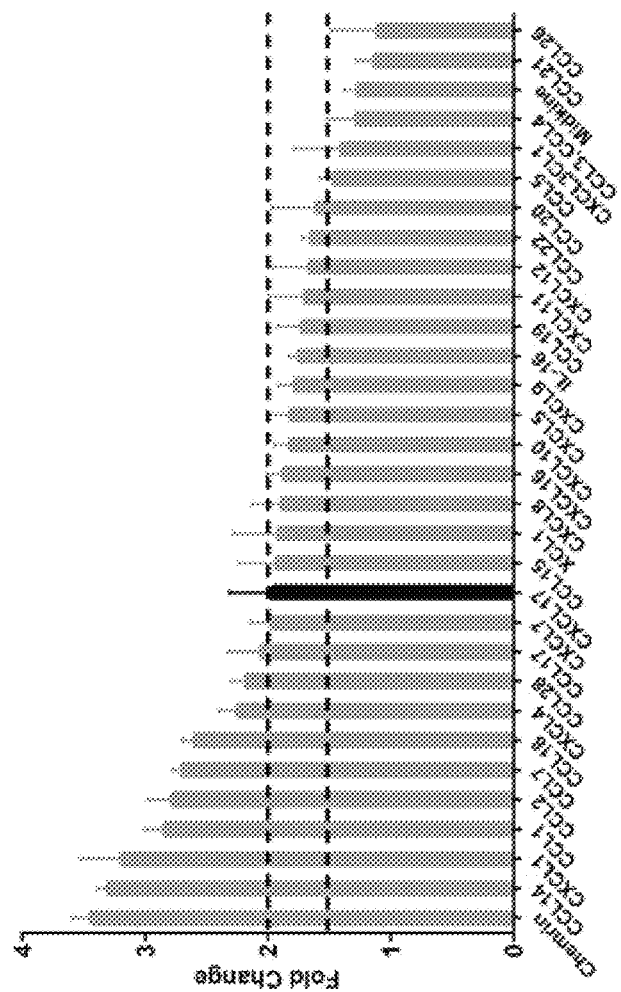
Figure 5A:
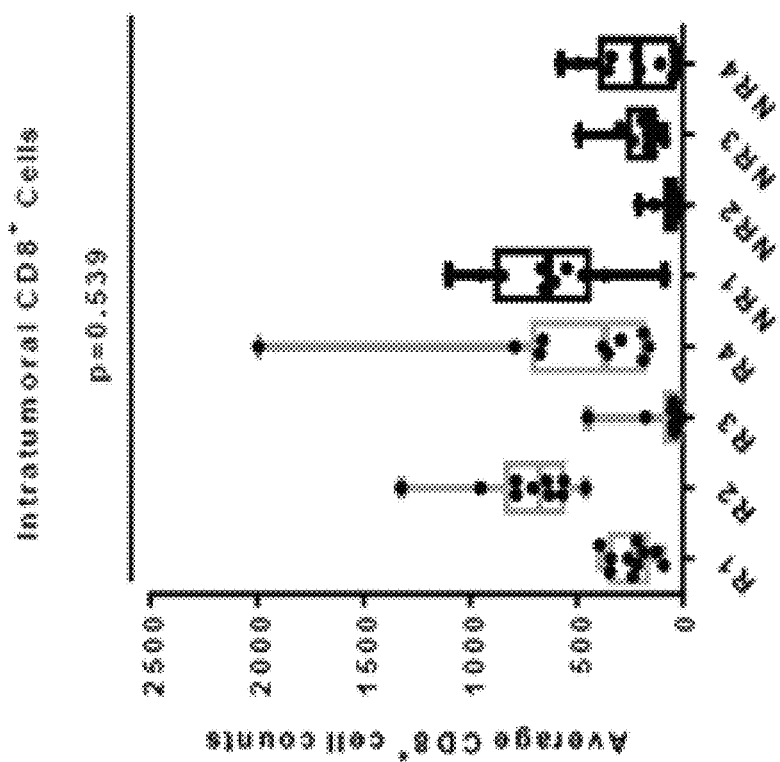
FIGS. 5A-5D show that responding tumors show increased T-cells along the invasive tumor margin prior to treatment.
Figure 5B:
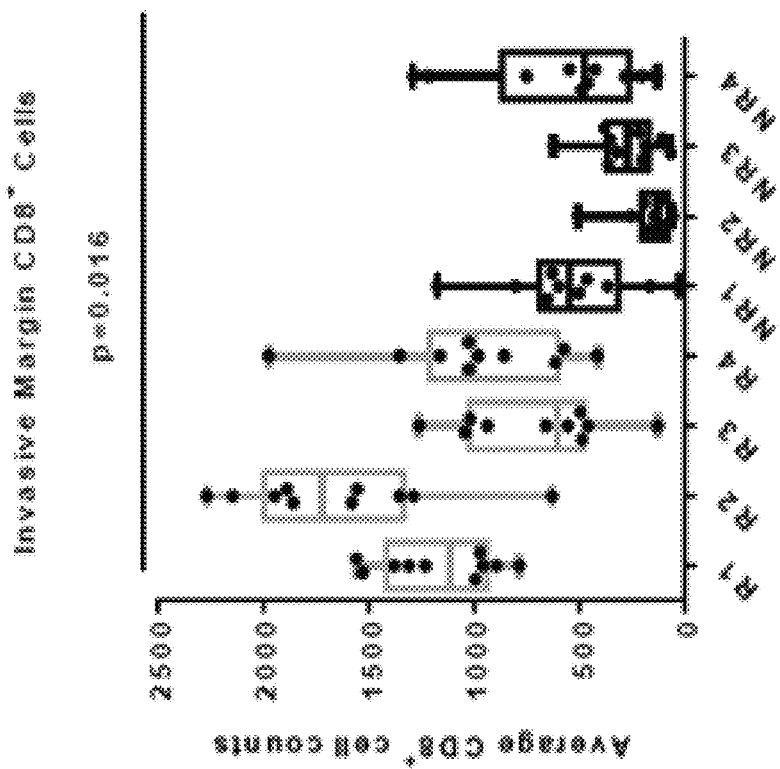
Figure 5D:
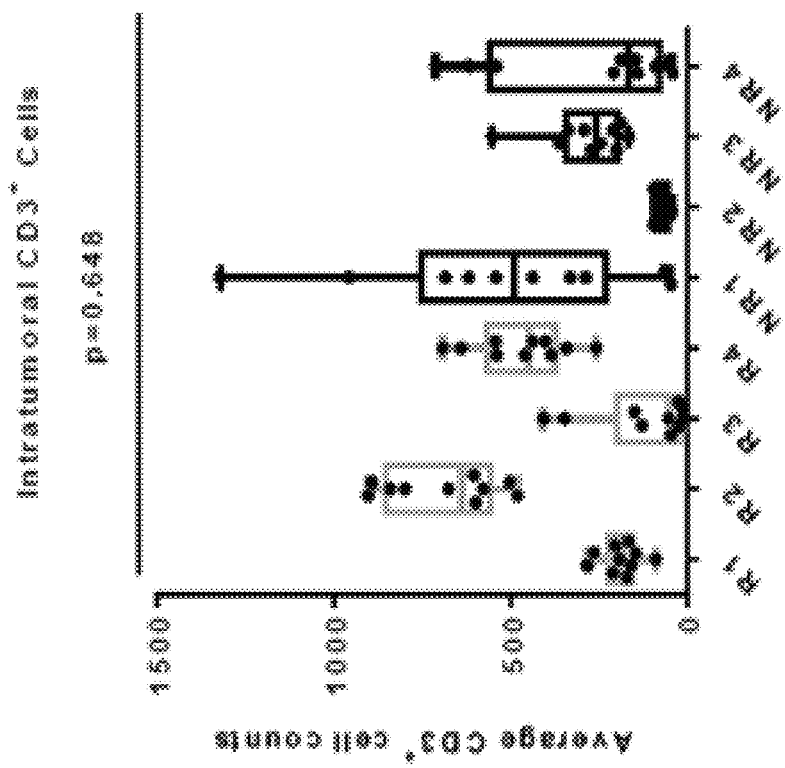
Figure 5C:
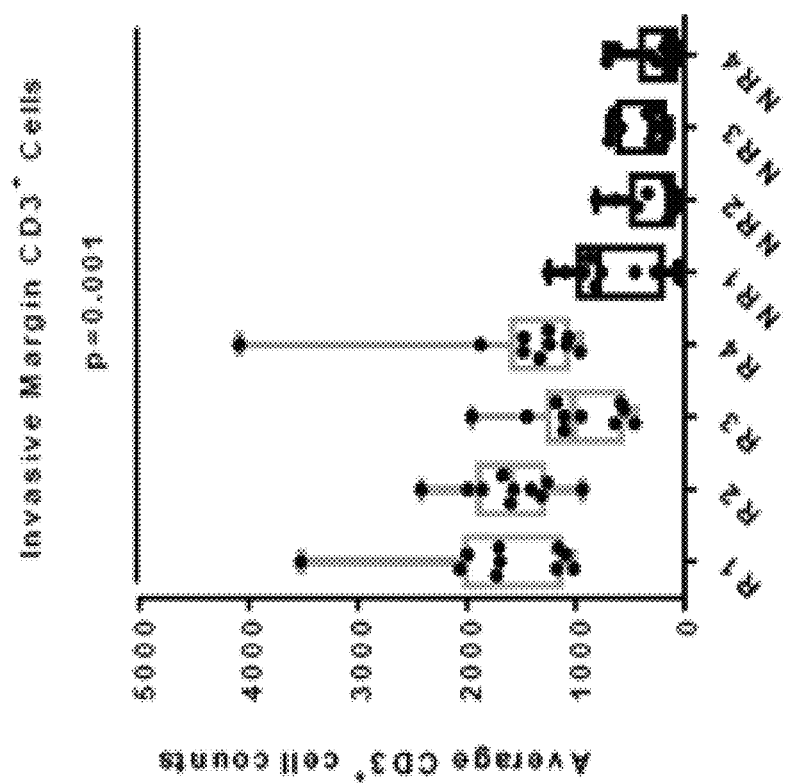
Figure 6:
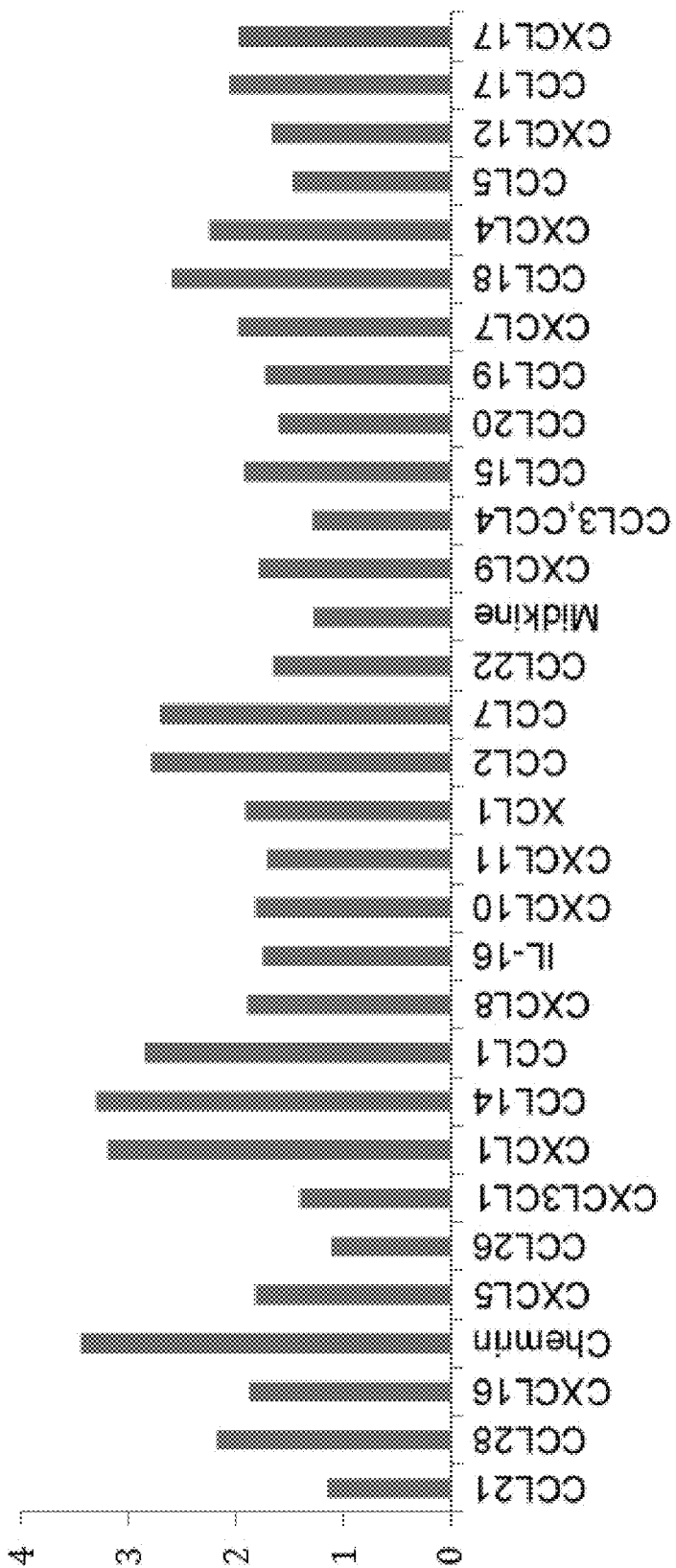
FIG. 6 shows a protein array with 31 human chemokines. 10 of 31 chemokines were elevated in responding tumors by FC>2. CXCL17 was elevated in non-responding tumors.

To determine if a bulk immune cell presence could be correlated to responsiveness, we performed CD8+ and CD3+ immunohistochemical staining and cell counting to quantify T-cells at the invasive margin and intratumoral region in metastatic melanoma tissue samples prior to any exposure to ICI therapies (n=4 per group). The tumors from patients responding to ICI (responding tumors) were found to have significantly elevated CD8+ and CD3+ counts at the invasive tumor margin (CD8+, P=0.016; CD3+, P=0.001) (FIGS. 1B, 1D; FIGS. 5A, 5C). Increased CD8+ cells along responding tumor's invasive margin is supported by a previous report[13]. However, unlike the prior report, we observed no significant difference between responding and non-responding tumors' CD8+ or CD3+ cells within the intratumoral region (CD8+, P>0.539; CD3+, P=0.648) (FIGS. 1B, 1D; FIGS. 5B, 5D). One determinant of T-cell trafficking to melanoma tumors is chemokine expression[14]. Using chemokine arrays targeting 31 human chemokines, we found responding tumors demonstrated significantly elevated levels of 10 chemokines (FC ratio >2) (FIG. 1E). CCL2, significantly elevated in responding tumors (FC=2.79), has been previously associated with CD8+ recruitment to melanoma metastases[14]. Only CXCL17 was elevated in non-responding tumors (FC=1.97). Complete array data is shown in FIG. 6. The presence of elevated immune cells along the tumor margin in responding tumors, along with elevated chemokines, provides impetus to examine protein-level features of responding versus non-responding tumors.

Figure 2A:
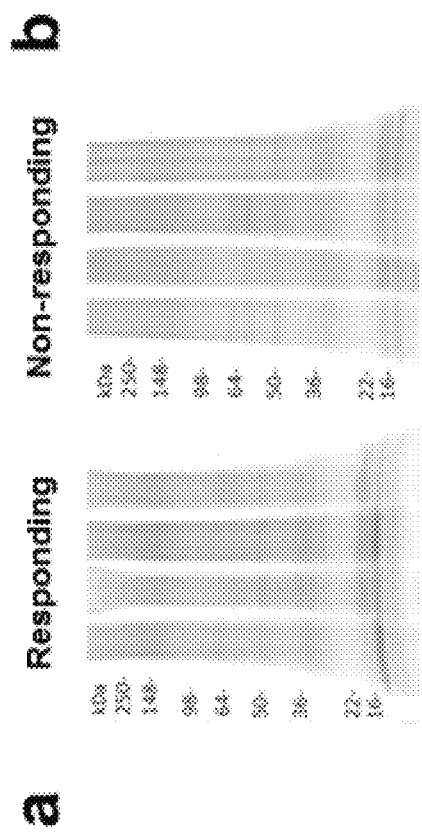
Figure 2B:
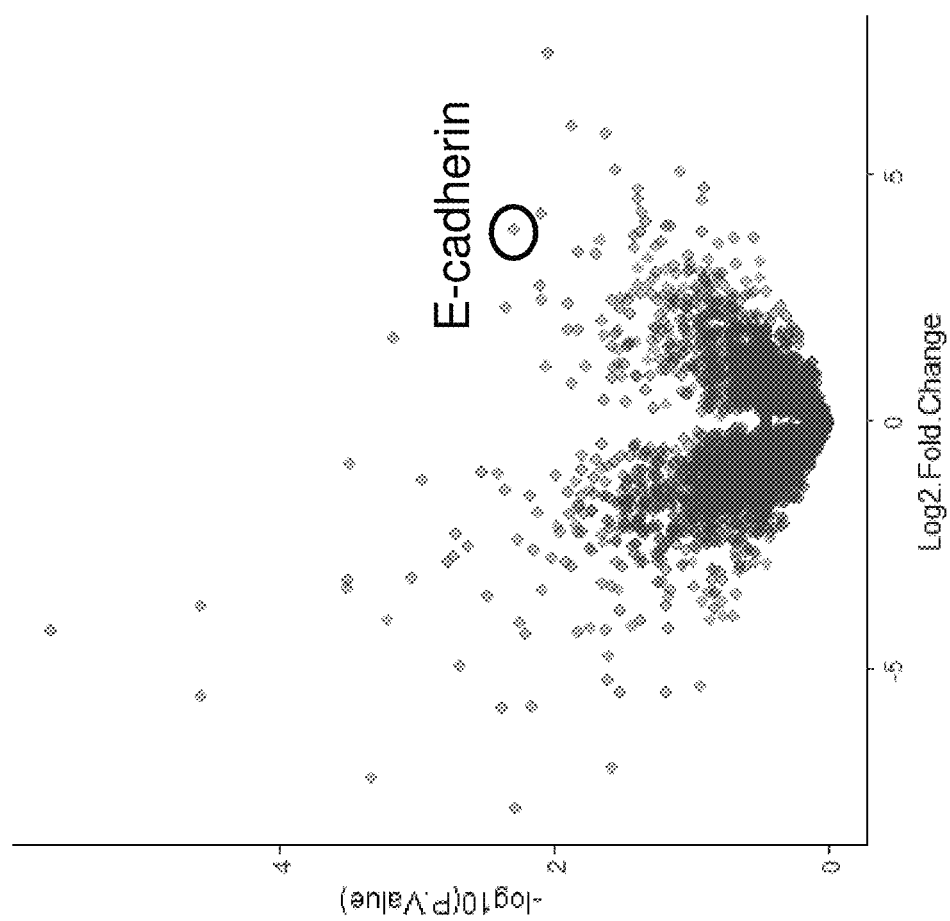
Figure 2C:
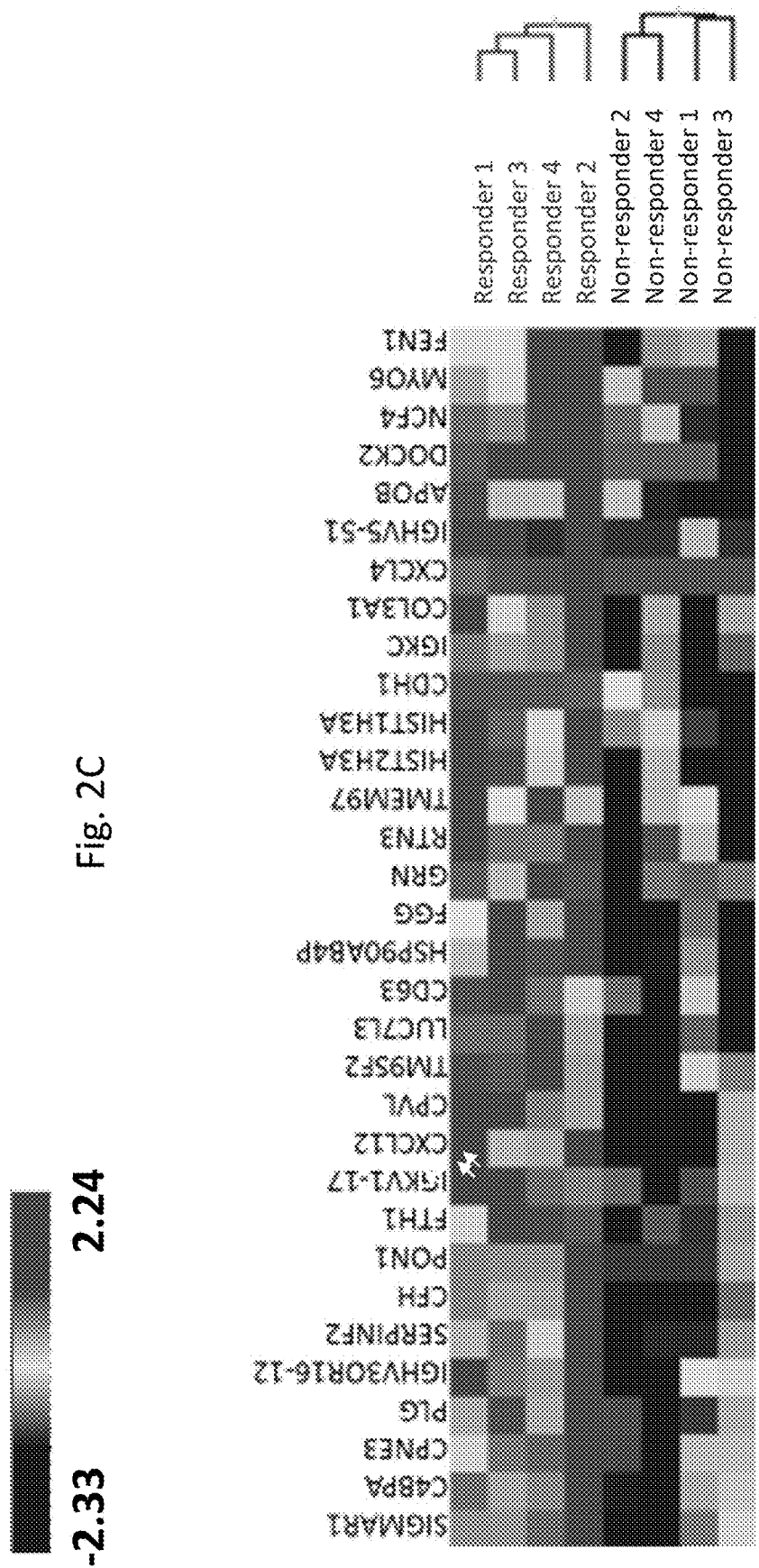
Figure 2C:
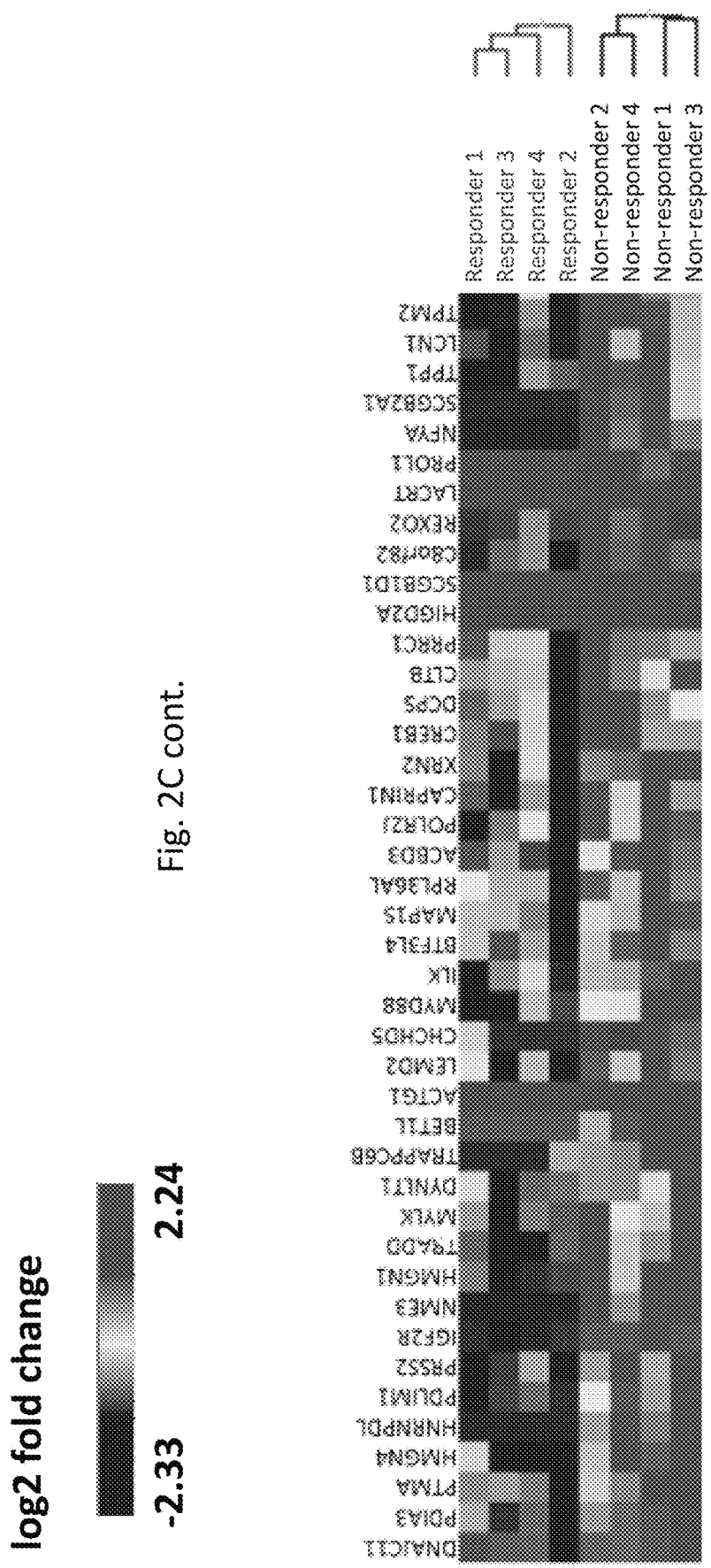
Figure 2C:
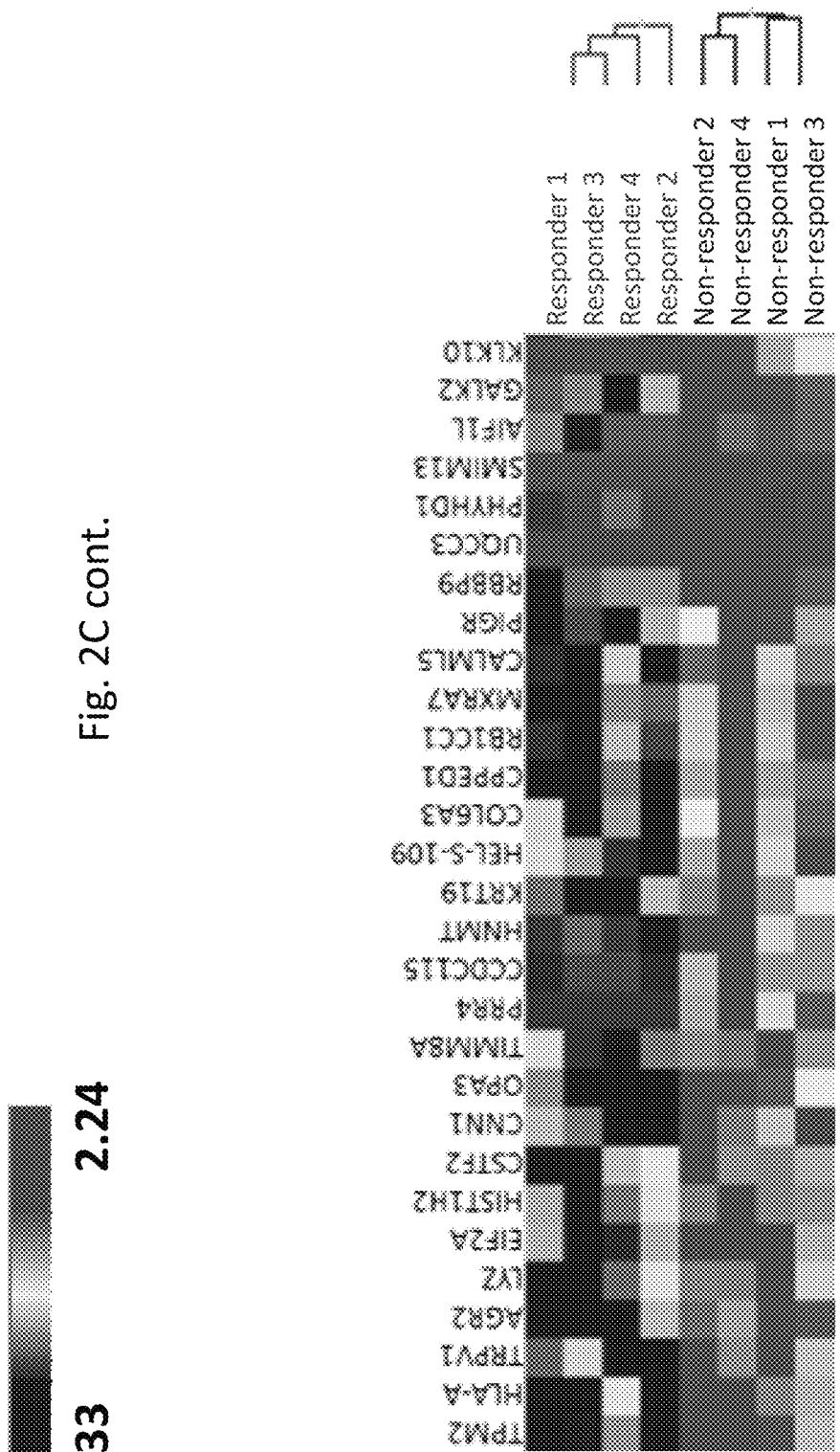

We performed the first to date proteomic analysis of pretreatment metastatic melanoma formalin-fixed, paraffin-embedded (FFPE) tissues from responding and non-responding tumors to ICI therapies. Proteins were isolated and relative levels were determined by label-free mass spectrometry, using approaches optimized from our previous studies of patient FFPE melanoma tissues[15,16]. High-resolution mass spectrometry identified 4318 proteins with high confidence (FDR of <1%) from 8 FFPE metastatic tumor samples (n=4 responding, n=4 non-responding; FIG. 2A). Remarkably, 87% (3777 of 4318) of the protein identifications were found in both the responding and non-responding tumor groups. The large number of proteins common between the groups highlights the similarities of the tumors, and confirms successful isolation of tumor tissues. Protein abundances of 106 proteins were found to be significantly different between the responding and non-responding groups by a Student's T test (p<0.05) and a log 2 fold change of >2. Significant proteins are illustrated by a volcano plot (FIG. 2B; Table 1). An unsupervised hierarchical cluster of the significant proteins from all 8 samples clearly separated the responding and non-responding tumors into two distinct clusters (FIG. 2C). These 106 significantly different proteins are putative markers for patient stratification.

TABLE 1

List of 106 proteins with p < 0.05 and log2 fold change >2. Arranged by NMS axis 1 r value.

| Protein IDs | Protein names | Gene names | NMS Axis 1 | NMS Axis 2 | Norm. Rank iBAQ | Ttest | Fold Change |
|---|---|---|---|---|---|---|---|
| A0A087WX17 | Cadherin-1; E-Cadherin | CDH1 | 0.948 | 0.076 | 1747 | 0.00508866 | 3.897 |
| P11717; | Cation-independent | IGF2R | −0.294 | −0.784 | 4107 | 0.00000215 | −4.210 |

TABLE 1-continued

List of 106 proteins with p < 0.05 and log2 fold change >2. Arranged by NMS axis 1 r value.

| Protein IDs | Protein names | Gene names | NMS Axis 1 | NMS Axis 2 | Norm. Rank iBAQ | Ttest | Fold Change |
|---|---|---|---|---|---|---|---|
| S4R328 | mannose-6-phosphate receptor | | | | | | |
| P07478 | Trypsin-2 | NFYA | −0.811 | −0.358 | 2332 | 0.00002632 | −3.710 |
| H3BPR2 | Nucleoside diphosphate kinase | NME3 | −0.664 | 0.086 | 1455 | 0.00002656 | −5.558 |
| Q9NVH1; B1AK20; Q5TH61 | DnaJ homolog subfamily C member 11 | DNAJC11 | −0.866 | 0.003 | 1901 | 0.00031416 | −3.358 |
| A0A087WU03 | Heterogeneous nuclear ribonucleoprotein D-like | HNRNPDL | −0.707 | 0.294 | 2522 | 0.00031614 | −3.198 |
| O75556 | Mammaglobin-B | SCGB2A1 | −0.589 | −0.455 | 705 | 0.00047170 | −7.218 |
| Q5TCU3 | Tropomyosin beta chain | TPM2 | −0.873 | −0.055 | 1916 | 0.00060906 | −3.996 |
| P05114; F2Z2W6 | Non-histone chromosomal protein HMG-14 | HMGN1 | −0.738 | −0.184 | 955 | 0.00090393 | −3.144 |
| P0DJ93 | Small integral membrane protein 13 | TRADD | −0.675 | 0.111 | 2825 | 0.00167426 | −2.834 |
| P23511 | Nuclear transcription factor Y subunit alpha | PRSS2 | −0.811 | 0.397 | 37 | 0.00186313 | −2.701 |
| A0A0C4DGZ9; O14773; E7EV34 | Tripeptidyl-peptidase 1 | TPP1 | −0.859 | −0.323 | 453 | 0.00194753 | −2.254 |
| O00479 | High mobility group nucleosome-binding domain-containing protein 4 | HMGN4 | −0.734 | 0.293 | 1348 | 0.00201945 | −4.948 |
| H7BZJ3 | Protein disulfide-isomerase A3 | PDIA3 | −0.79 | 0.058 | 713 | 0.00237334 | −2.492 |
| P50135 | Histamine N-methyltransferase | HNMT | −0.693 | 0.358 | 1933 | 0.00325907 | −3.535 |
| P31025; Q5VSP4 | Lipocalin-1 | LCN1 | −0.418 | −0.784 | 161 | 0.00408734 | −5.782 |
| P28799; K7EKL3 | Granulins; Acrogranin; Paragranulin | GRN | 0.663 | −0.029 | 1139 | 0.00451598 | 2.330 |
| A0A087WY73; Q16378 | Proline-rich protein 4 | PRR4 | −0.53 | 0.408 | 150 | 0.00533224 | −7.833 |
| Q9GZZ8; F8W0V3; H0YI00 | Extracellular glycoprotein lacritin | TRPV1; SHPK | −0.672 | −0.338 | 2245 | 0.00541607 | −2.398 |
| Q96NT0; F8WCZ3; B8ZZ99 | Coiled-coil domain-containing protein 115 | CCDC115 | −0.594 | 0.369 | 1634 | 0.00558181 | −4.052 |
| Q9H0D6 | 5-3 exoribonuclease 2 | XRN2 | −0.875 | −0.27 | 2728 | 0.00624304 | −4.305 |
| O95994; B5MC07; C9J3E2; H7C3Z9 | Anterior gradient protein 2 homolog | AGR2 | −0.653 | −0.531 | 881 | 0.00678979 | −5.741 |
| O00151 | PDZ and LIM domain protein 1 | PDLIM1 | −0.536 | 0.378 | 1281 | 0.00701268 | −2.571 |
| O95197 | Reticulon-3 | RTN3 | 0.883 | −0.085 | 2378 | 0.00795091 | 2.752 |
| P51911; B7Z7E1 | Calponin-1; Calponin | TIMM8A | −0.632 | −0.609 | 1454 | 0.00813868 | −3.402 |
| Q9H3G5 | Probable serine carboxypeptidase CPVL | CPVL | 0.875 | 0.008 | 1553 | 0.00816674 | 4.223 |
| Q99805 | Transmembrane 9 superfamily member 2 | TM9SF2 | 0.86 | −0.284 | 2341 | 0.00827408 | 2.505 |
| Q71DI3; Q16695 | Histone H3.2; Histone H3.1t | HIST2H3A; HIST3H3 | 0.684 | 0.36 | 301 | 0.00912684 | 7.491 |
| P16220; E9PAR2 | Cyclic AMP-dependent transcription factor ATF-1 | CREB1; CREM; ATF1 | −0.829 | 0.057 | 1846 | 0.00949588 | −2.747 |
| O95989 | Diphosphoinositol polyphosphate phosphohydrolase 1 | NUDT3 | −0.702 | −0.011 | 2026 | 0.01071611 | −2.082 |
| B8ZZQ6; P06454 | Prothymosin alpha | PTMA | −0.697 | −0.024 | 279 | 0.01091580 | −2.232 |
| P61626; F8VV32; A0A0B4J259 | Lysozyme C; Lysozyme | NACAP1 | −0.659 | −0.575 | 1699 | 0.01228735 | −2.839 |
| Q99720; Q5T1J1 | Sigma non-opioid intracellular receptor 1 | SIGMAR1 | 0.619 | 0.312 | 1397 | 0.01275638 | 2.418 |
| Q15746; D6R9C2 | Myosin light chain kinase | MYLK | −0.558 | 0.183 | 2588 | 0.01329835 | −2.908 |
| F8VV56; F8W022 | Tetraspanin; CD63 antigen | CD63 | 0.655 | −0.105 | 431 | 0.01339848 | 6.002 |

TABLE 1-continued

List of 106 proteins with p < 0.05 and log2 fold change >2. Arranged by NMS axis 1 r value.

| Protein IDs | Protein names | Gene names | NMS Axis 1 | NMS Axis 2 | Norm. Rank iBAQ | Ttest | Fold Change |
|---|---|---|---|---|---|---|---|
| Q96K17; E9PL10 | Transcription factor BTF3 homolog 4; Transcription factor BTF3 | BTF3L4 | −0.749 | −0.493 | 1157 | 0.01429076 | −2.073 |
| P04003 | C4b-binding protein alpha chain | C4BPA | 0.518 | 0.34 | 1275 | 0.01468716 | 3.465 |
| Q9BZK3 | Putative nascent polypeptide-associated complex subunit | LYZ | −0.659 | −0.59 | 36 | 0.01483640 | −2.222 |
| O60220 | Mitochondrial import inner membrane translocase subunit Tim8 A | CNN1 | −0.632 | 0.196 | 752 | 0.01502112 | −4.249 |
| K7EMS3 | Keratin, type I cytoskeletal 19 | KRT19 | −0.694 | 0.306 | 1712 | 0.01579112 | −2.207 |
| P00747; Q5TEH5 | Plasminogen; Plasmin heavy chain A | HLA-A | −0.718 | 0.06 | 1475 | 0.01831299 | −4.153 |
| F8WAE5; Q9BY44 | Eukaryotic translation initiation factor 2A | EIF2A | −0.745 | −0.518 | 3189 | 0.01844408 | −2.535 |
| P52435; A0A0B4J2F8 | DNA-directed RNA polymerase II subunit RPB11-a | POLR2J | −0.651 | −0.633 | 1996 | 0.01899335 | −2.594 |
| A0A075B7B8 | Protein IGHV3OR16-12 | IGHV3OR16-12 | 0.547 | 0.14 | 1564 | 0.02020549 | 3.432 |
| Q92608; E5RFJ0; E7ERW7; F6S220 | Dedicator of cytokinesis protein 2 | DOCK2 | −0.85 | 0.252 | 2150 | 0.02138020 | 3.713 |
| Q93077; Q7L7L0; P04908 | H2A type 1-C; H2A type 3; H2A type 1-B/E | H2AC; H2A; H2AB | −0.62 | −0.368 | 1148 | 0.02229538 | −3.285 |
| Q86SZ2; G3V4C3; G3V2H7 | Trafficking protein particle complex subunit 6B | TRAPPC6B | −0.725 | 0.381 | 2704 | 0.02235085 | −2.265 |
| O75131; A0A087WYQ3 | Copine-3 | CPNE3 | 0.412 | 0.411 | 1566 | 0.02263375 | 2.090 |
| Q9NZT1 | Calmodulin-like protein 5 | CALML5 | −0.727 | 0.414 | 78 | 0.02329383 | −2.429 |
| P30453; P30457; P30450 | HLA class I histocompatibility antigen, A-34 alpha chain | PLG | −0.718 | −0.528 | 643 | 0.02411270 | 5.840 |
| Q6UW78 | Ubiquinol-cytochrome-c reductase complex assembly factor 3 | UQCC3 | −0.697 | −0.6 | 1710 | 0.02416732 | −4.201 |
| Q9BW72 | HIG1 domain family member 2A, mitochondrial | HIGD2A | −0.713 | −0.2 | 1156 | 0.02459816 | −5.202 |
| O95968 | Secretoglobin family 1D member 1 | SCGB1D1 | −0.65 | −0.354 | 1375 | 0.02505123 | −4.725 |
| Q9H6K4; B4DK77 | Optic atrophy 3 protein | OPA3 | −0.571 | −0.092 | 2439 | 0.02529914 | −2.009 |
| Q96M27 | Protein PRRC1 | C8orf82 | 0.372 | −0.11 | 2672 | 0.02551230 | −2.134 |
| I3L4N8 | Actin, cytoplasmic 2 | ACTG1 | −0.693 | 0.227 | 2224 | 0.02622463 | −3.300 |
| P39748; I3L3E9; F5H1Y3 | Flap endonuclease 1 | FEN1 | −0.612 | 0.102 | 1464 | 0.02644831 | 2.490 |
| A0A0B4J2A0; Q9UHJ6 | Sedoheptulokinase | LACRT | −0.672 | 0.318 | 410 | 0.02654007 | −7.001 |
| O43240; M0R132 | Kallikrein-10 | KLK10 | 0.585 | 0.391 | 2383 | 0.02799232 | −2.828 |
| Q5SRE7; G5E9M0 | Phytanoyl-CoA dioxygenase domain-containing protein 1 | PHYHD1 | −0.713 | 0.176 | 2698 | 0.02817581 | −2.439 |
| P68431 | Histone H3.1 | HIST1H3A | −0.639 | 0.479 | 306 | 0.02834022 | 5.132 |
| P09497; D6RJD1; H0Y9Q6 | Clathrin light chain B | CLTB | −0.656 | 0.236 | 1802 | 0.02864028 | −2.366 |
| V9HW75; A0A087WSV8 | Nucleobindin-2; Nesfatin-1 | HEL-S-109; NUCB2; Nucb2 | −0.546 | −0.031 | 1780 | 0.02923338 | −3.375 |
| P01833 | Polymeric immunoglobulin receptor | PIGR | 0.532 | 0.509 | 487 | 0.02978636 | −3.810 |
| A0A087X0P7; Q99935 | Proline-rich protein 1; Opiorphin | PROL1 | −0.572 | 0.162 | 896 | 0.03001720 | −5.453 |
| Q8NC56; H0Y9B7 | LEM domain-containing protein 2 | LEMD2 | 0.672 | −0.136 | 2339 | 0.03031849 | −2.166 |

TABLE 1-continued

List of 106 proteins with p < 0.05 and log2 fold change >2. Arranged by NMS axis 1 r value.

| Protein IDs | Protein names | Gene names | NMS Axis 1 | NMS Axis 2 | Norm. Rank iBAQ | Ttest | Fold Change |
|---|---|---|---|---|---|---|---|
| A0A087X130; A0A0B4J1T9 | Ig kappa chain C region | IGKC | −0.678 | 0.541 | 1304 | 0.03067510 | 2.317 |
| Q15628 | Tumor necrosis factor receptor type 1-associated DEATH domain protein | SMIM13 | −0.675 | −0.707 | 2412 | 0.03117703 | −2.898 |
| Q58FF6 | Putative heat shock protein HSP 90-beta 4 | HSP90AB4P | −0.514 | 0.389 | 2177 | 0.03159875 | 2.526 |
| Q9UBU6 | Protein FAM8A1 | FAM8A1 | 0.707 | 0.179 | 3220 | 0.03204089 | −2.131 |
| Q14444; E9PLA9 | Caprin-1 | CAPRIN1 | −0.801 | 0.189 | 1600 | 0.03285755 | −2.054 |
| P63172; Q5VTU3 | Dynein light chain Tctex-type 1 | DYNLT1 | 0.483 | 0.157 | 1215 | 0.03358731 | −2.042 |
| P02794; G3V192 | Ferritin heavy chain; Ferritin heavy chain, N-terminally processed; Ferritin | FTH1 | −0.66 | −0.551 | 252 | 0.03471847 | 2.473 |
| Q9BRF8 | Serine/threonine-protein phosphatase CPPED1 | CPPED1 | 0.653 | −0.634 | 1444 | 0.03567748 | −2.144 |
| Q9UM54; A0A0A0MRM8 | Unconventional myosin-VI | MYO6 | −0.582 | 0.427 | 2795 | 0.03614352 | 2.221 |
| H0YGR4; H0YG54; Q9Y3B8; F5GYG5 | Oligoribonuclease, mitochondrial | REXO2 | 0.372 | 0.436 | 2584 | 0.03667320 | −2.496 |
| J3KPP4 | Luc7-like protein 3 | LUC7L3 | 0.695 | 0.002 | 2379 | 0.03692512 | 2.616 |
| E7ENL6 | Collagen alpha-3 | COL6A3 | −0.746 | −0.249 | 2889 | 0.03731983 | −4.143 |
| P08697; A0A0G2JPA8 | Alpha-2-antiplasmin | SERPINF2 | −0.666 | −0.172 | 1610 | 0.03773686 | 3.784 |
| A0A0B4J1Z4 | Protein IGKV1-17 | IGKV1-17 | −0.796 | −0.065 | 1260 | 0.03817804 | 3.562 |
| E9PID8; P33240 | Cleavage stimulation factor subunit 2 | CSTF2 | −0.668 | −0.346 | 3432 | 0.03833607 | −2.012 |
| P48059 | LIM and senescent cell antigen-like-containing domain protein 1 | LIMS1 | −0.786 | −0.006 | 2270 | 0.03849649 | −2.670 |
| Q96C86 | m7GpppX diphosphatase | DCPS | −0.541 | −0.128 | 1492 | 0.03852007 | −2.111 |
| Q9H3P7 | Golgi resident protein GCP60 | ACBD3 | 0.445 | 0.4 | 2148 | 0.03923983 | −2.082 |
| O75884; A0A087WYQ5 | Putative hydrolase RBBP9 | RBBP9 | 0.678 | 0.232 | 2908 | 0.03987119 | −2.453 |
| A0A0A0MS70 | Myeloid differentiation primary response protein MyD88 | MYD88 | 0.612 | 0.186 | 3312 | 0.04019127 | −2.448 |
| P02776; P10720 | Platelet factor 4; CXCL4 | PF4; PF4V1 | 0.33 | 0.404 | 2115 | 0.04076271 | 3.133 |
| P48061 | Stromal cell-derived factor 1 | CXCL12 | 0.388 | 0.481 | 2137 | 0.04079908 | 2.811 |
| P02461; H7C435 | Collagen alpha-1(III) chain | COL3A1 | −0.719 | 0.303 | 1180 | 0.04131242 | 4.525 |
| P04114 | Apolipoprotein B-100; Apolipoprotein B-48 | APOB | −0.735 | 0.385 | 2362 | 0.04157079 | 4.722 |
| P08603; A0A0D9SG88 | Complement factor H | CFH | −0.391 | −0.02 | 901 | 0.04166386 | 3.848 |
| P84157 | Matrix-remodeling-associated protein 7 | MXRA7 | −0.518 | −0.187 | 2488 | 0.04187099 | −2.006 |
| Q8TDY2 | RB1-inducible coiled-coil protein 1 | RB1CC1 | −0.791 | −0.218 | 2765 | 0.04198836 | −2.131 |
| Q9BQI0; Q5JUP3 | Allograft inflammatory factor 1-like | AIF1L | 0.587 | 0.038 | 1458 | 0.04272124 | −4.009 |
| Q9NYM9; H7BXT7 | BET1-like protein | BET1L | −0.528 | −0.622 | 2376 | 0.04298119 | −2.830 |
| H0YF29; Q6P1X6 | UPF0598 protein C8orf82 | PRRC1 | 0.372 | 0.356 | 1385 | 0.04304288 | −2.689 |
| C9JPQ9; C9JU00 | Fibrinogen gamma chain | FGG | −0.593 | −0.615 | 1147 | 0.04365846 | 4.285 |
| Q66K74; M0R1M7 | Microtubule-associated protein 1S | MAP1S | −0.507 | 0.174 | 2665 | 0.04422843 | −2.217 |
| Q15080; A0A0G2JR51; B0QY04 | Neutrophil cytosol factor 4 | NCF4 | −0.7 | −0.575 | 2618 | 0.04453049 | 2.592 |
| Q9BSY4 | Coiled-coil-helix-domain-containing protein 5 | CHCHD5 | 0.728 | 0.068 | 2613 | 0.04475782 | −2.277 |
| A0A0A0MTH3; Q13418 | Integrin-linked protein kinase | ILK | −0.658 | 0.227 | 1737 | 0.04502066 | −2.131 |

TABLE 1-continued

List of 106 proteins with p < 0.05 and log2 fold change >2. Arranged by NMS axis 1 r value.

| Protein IDs | Protein names | Gene names | NMS Axis 1 | NMS Axis 2 | Norm. Rank iBAQ | Ttest | Fold Change |
|---|---|---|---|---|---|---|---|
| Q969Q0 | 60S ribosomal protein L36a-like | RPL36AL | 0.315 | 0.402 | 1234 | 0.04573715 | −2.807 |
| A0A0C4DH38; A0A0G2JP91 | Protein IGHV5-51 | IGHV5-51 | 0.568 | −0.237 | 1409 | 0.04669038 | 4.081 |
| B7ZAX5 | N-acetylgalactosamine kinase | GALK2 | 0.701 | 0.006 | 3100 | 0.04671822 | −2.193 |
| P27169; F8WF42 | Serum paraoxonase/arylesterase 1 | PON1 | 0.318 | 0.058 | 1595 | 0.04799826 | 3.352 |
| Q5BJF2; J3KT68; Q86XC5; J3KTD1 | Transmembrane protein 97 | TMEM97 | −0.551 | −0.428 | 1851 | 0.04908993 | 2.832 |

Starting with 106 proteins with p<0.05 and log 2 FC >2, out of a total of 4318 proteins, non-metric multidimensional scaling (NMS) was used to extract non-redundant information from these data. NMS is an ordination technique that attempts to collapse a swarm of multidimensional data into a two-dimensional plot which displays any underlying structure within the data[7]. Our assumption is that, among the list of 106 significantly differing proteins, a small subset would serve to explain the majority of the variation between responding and non-responding tumors. NMS of protein abundance values produced a two-dimensional ordination (FIG. 2d) with a final stress of 0.00795. In the plane defined by the two axes of the NMS ordination, triangles representing responding tumors were distant from triangles representing non-responding tumors, plotting high on NMS 1. E-cadherin (CDH1) was found to have the largest r value for NMS axis 1 and best separated the non-responding and responding patients (r=0.984; Table 1). We reason there is a physiological explanation underlying the placement of E-cadherin within the ordination. Therefore, we targeted E-cadherin for bioinformatics analysis and further investigation.

Figures 3A, 3C:
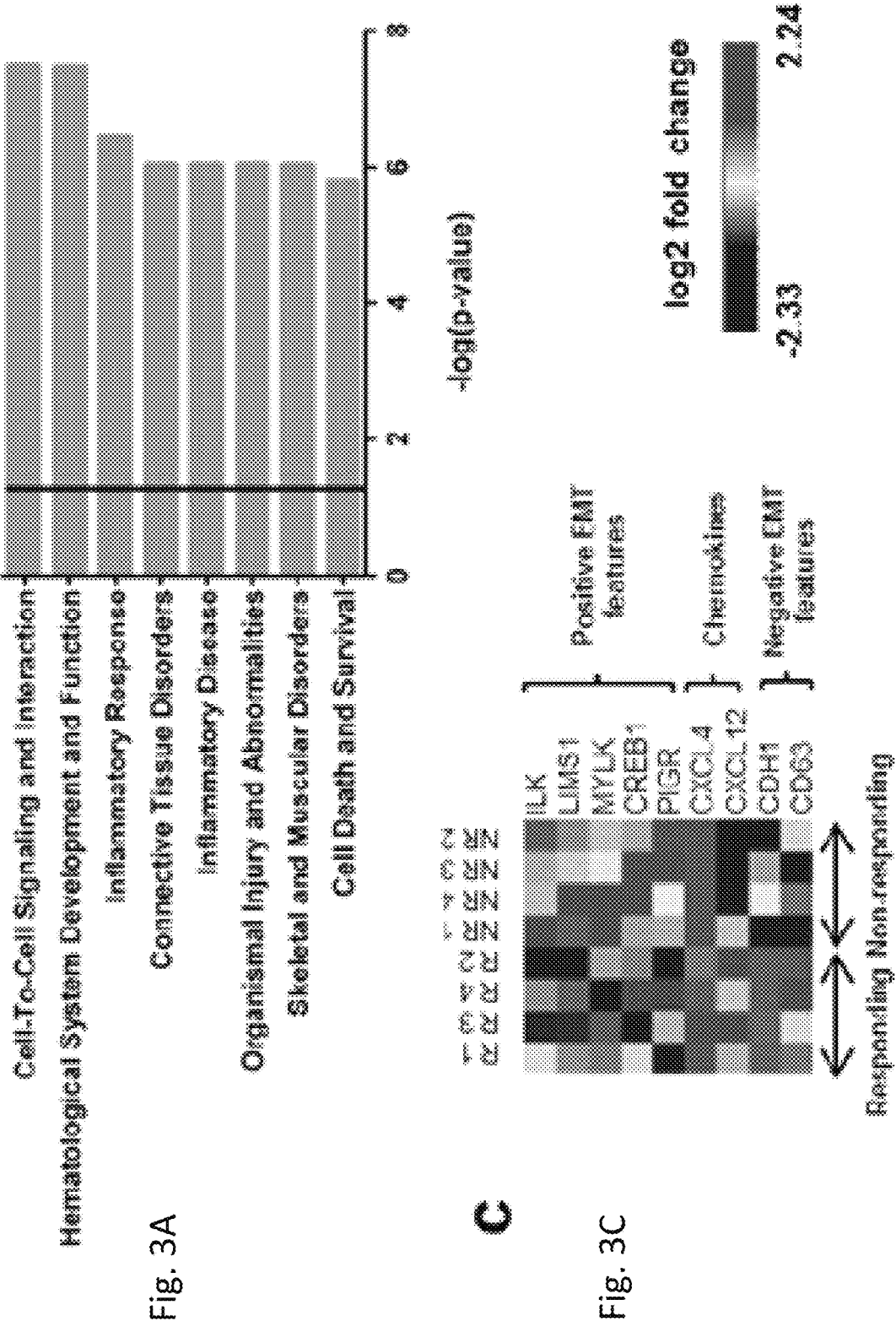
FIGS. 3A-3F show that non-responding tumors show features of EMT.
Figure 3B:
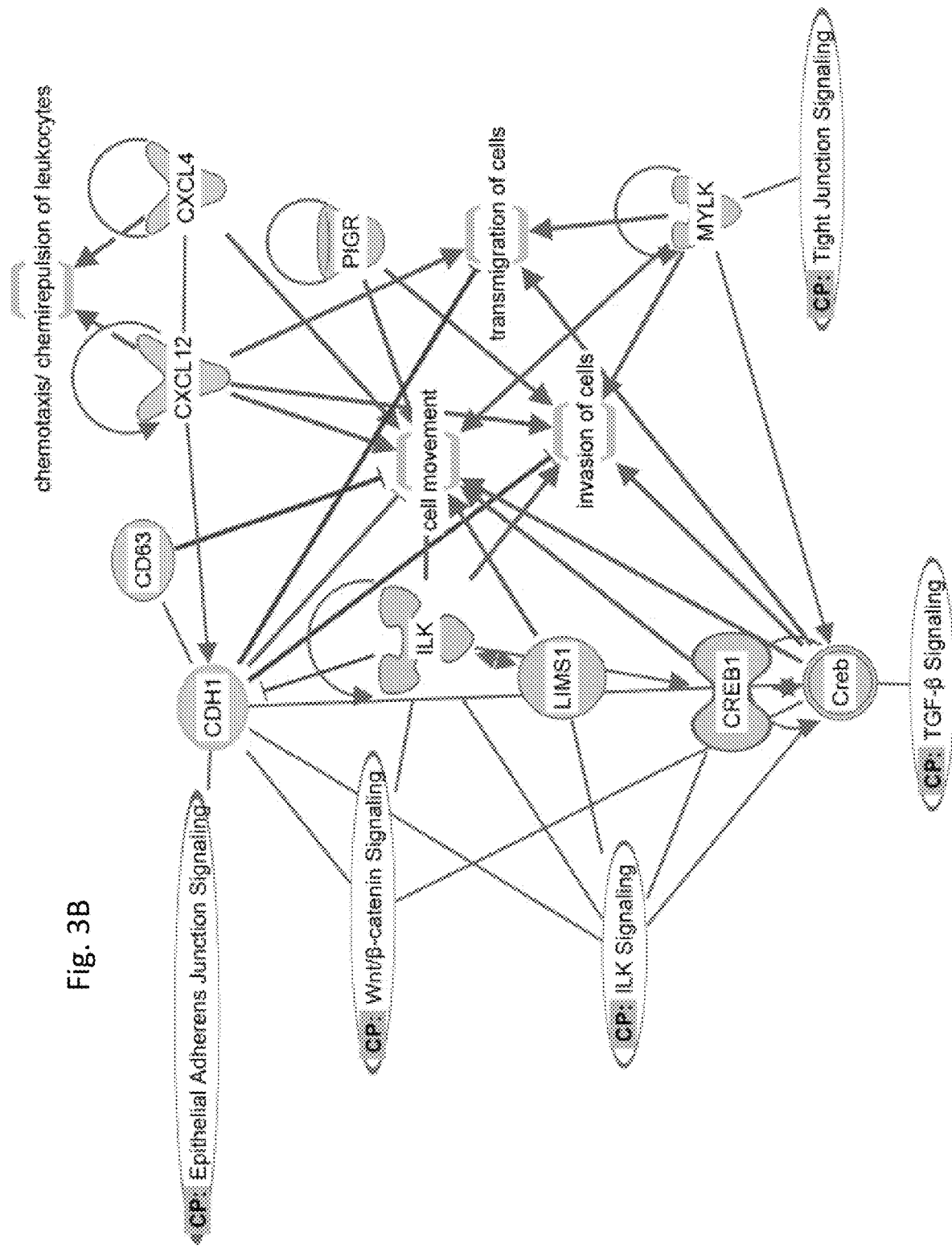
Figure 7:
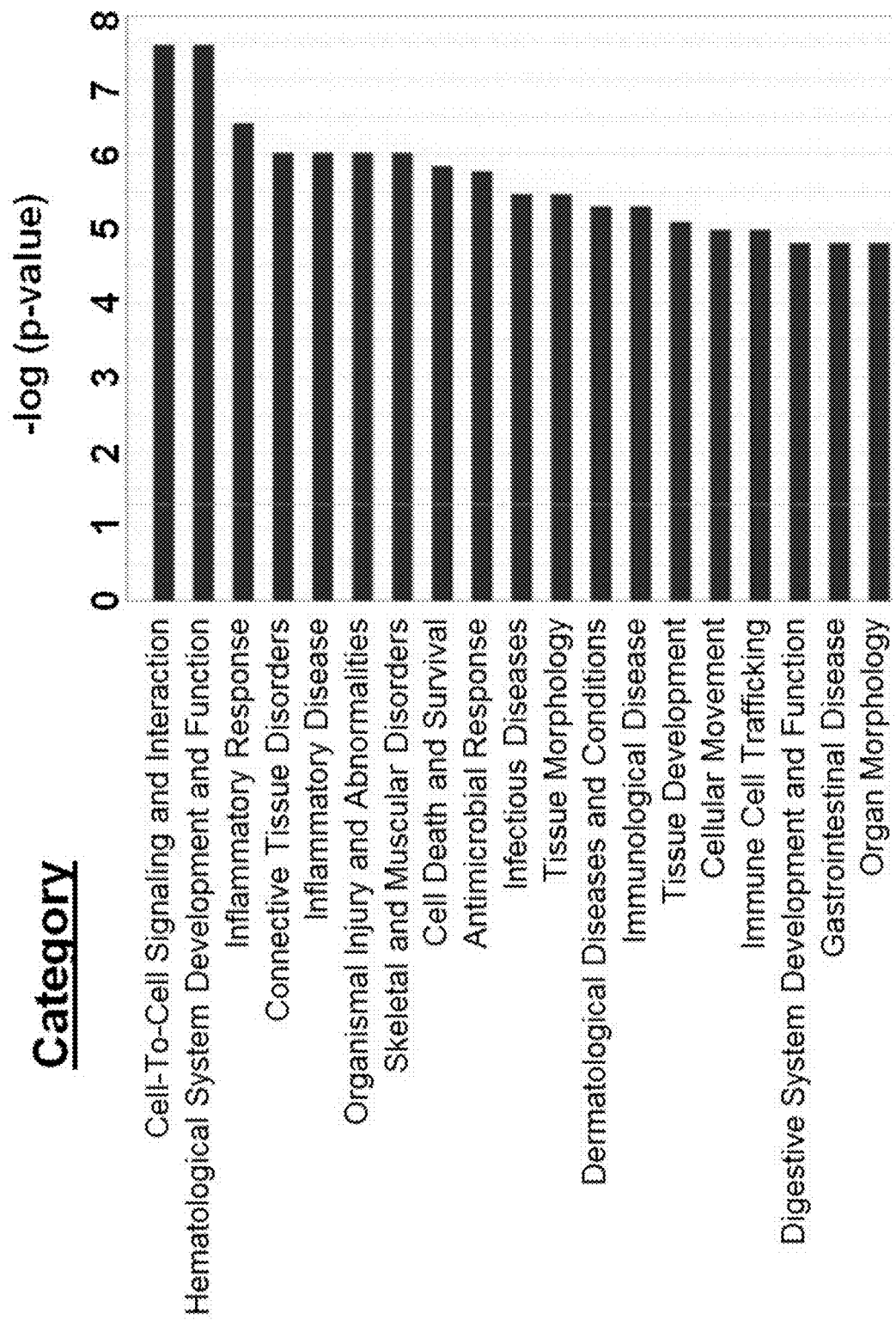
FIG. 7 shows an ingenuity Pathway Analysis of differentially regulated proteins between responding and non-responding tumors. Threshold significance was set at 0.05 (1.3 on −log scale).
Figure 7:
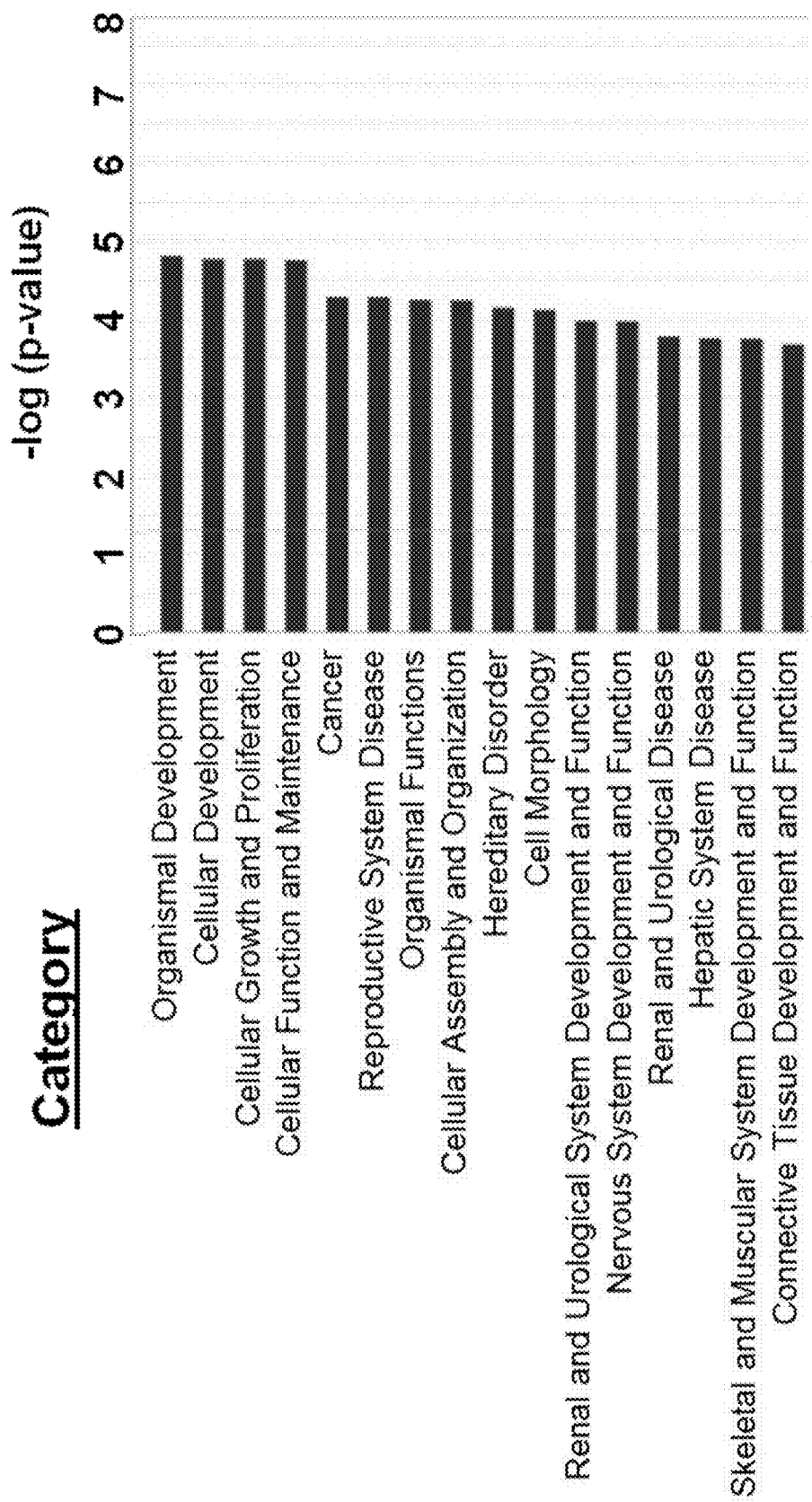
Figure 7:
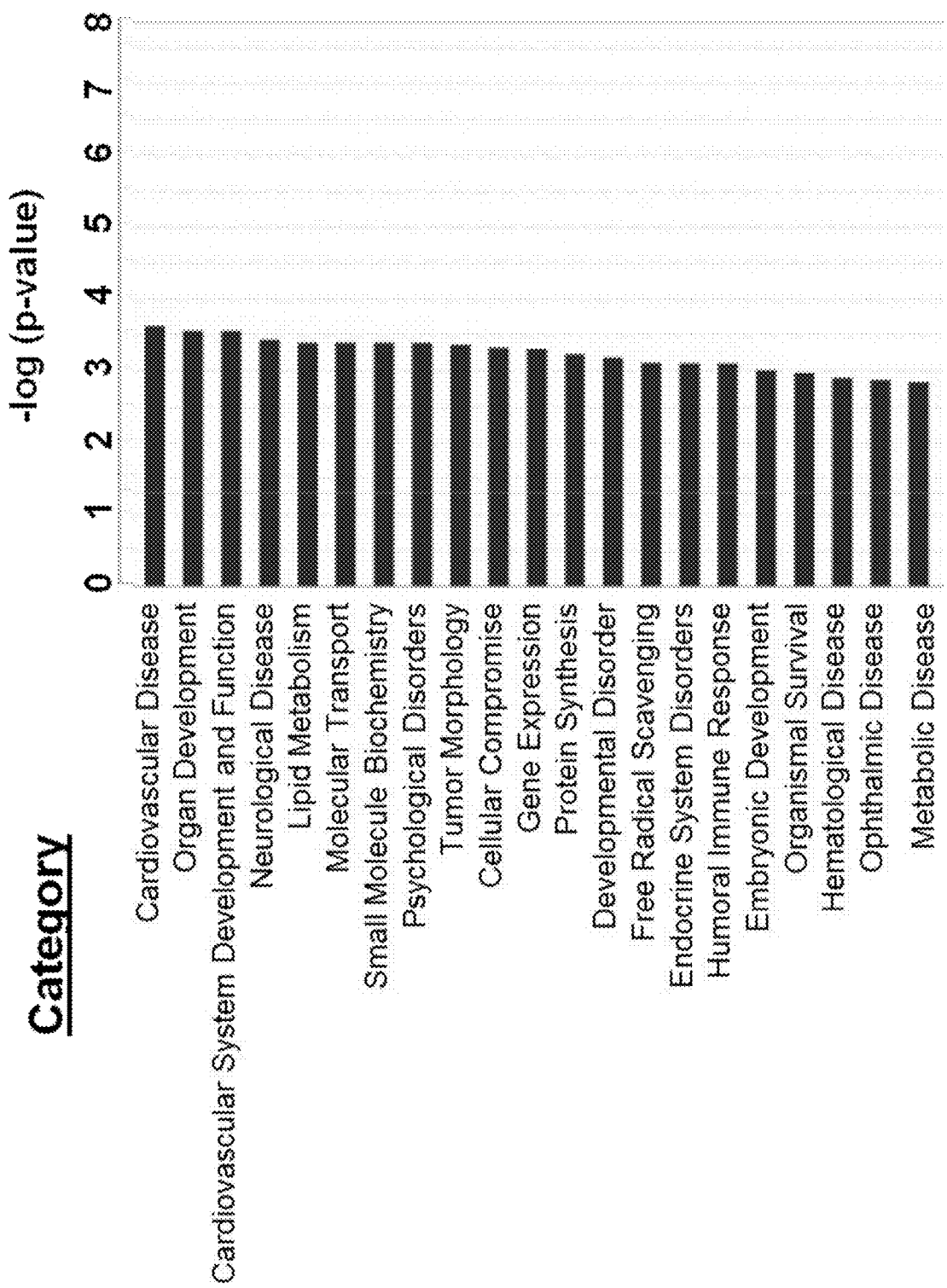
Figure 7:
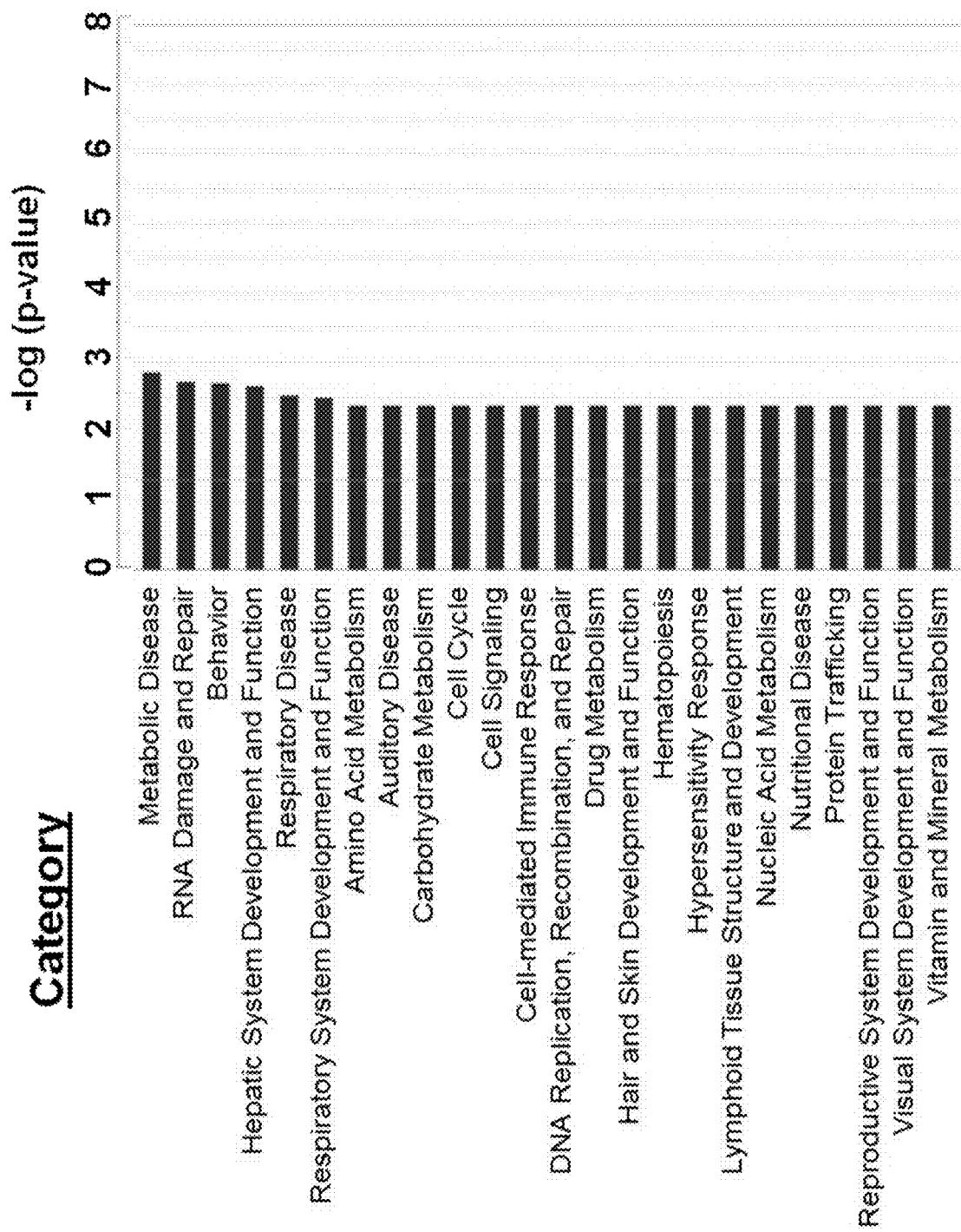

Pathway analysis was performed to examine biological processes represented by the differentially-regulated proteins with p<0.05 and log 2 FC>2. Proteins with elevated or repressed levels in non-responding (versus responding) tumors were queried to determine pathways more active in non-responding tumors. Pathways enriched included Cell-To-Cell Signaling and Interaction, Hematological System Development and Function, and the Inflammatory Response. The top 8 Functions and Diseases Pathways are shown in FIG. 3A. A total list of identified pathways significantly elevated in non-responding tumors can be found in FIG. 7. We next examined the identified network "Cell-To-Cell Signaling, Hematological System Development and Function, and Inflammatory Response" for canonical pathways. Pathways active within this network included: ILK signaling, Integrin signaling, and Wnt/β-catenin signaling. Functions included cell movement, invasion of cells, and transmigration of cells (FIG. 3B). The Ingenuity Knowledge Base, along with our own literature review, implicated this set of enriched pathways in epithelial-mesenchymal transition (EMT). Mesenchymal transition has been implicated in resistance to checkpoint blockade at the transcriptomic level[12]. Proteins separated into positive-EMT features (ILK, LIMS1, CREB1, PIGR, and MYLK; elevated in non-responding tumors), negative EMT features (CDH1 (E-cadherin), CD63; elevated in responding tumors), and chemokines CXCL4 and CXCL12 (elevated in responding tumors) (FIGS. 3C, 3D).

Figure 3D:
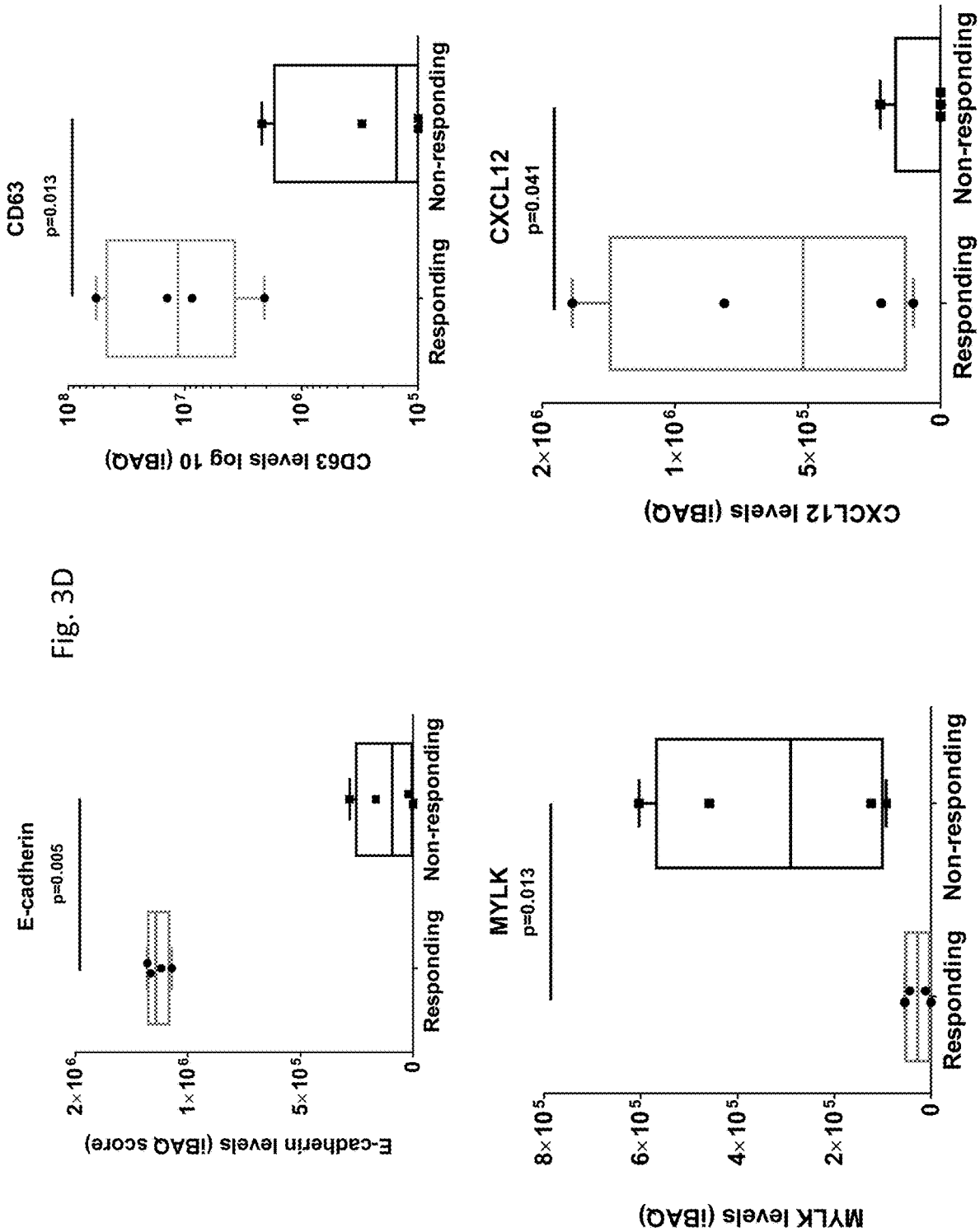
Figure 3D:
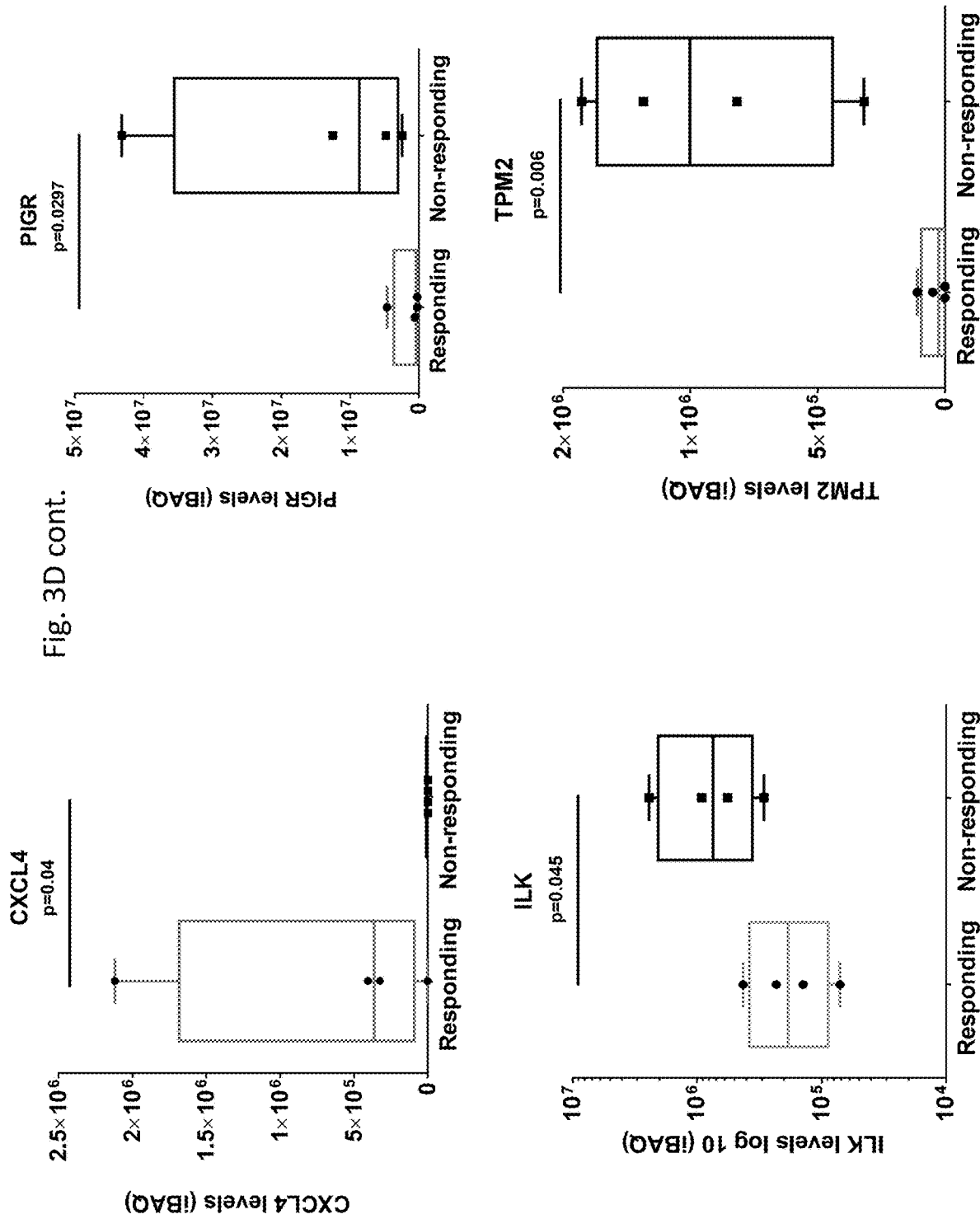
Figure 3D:
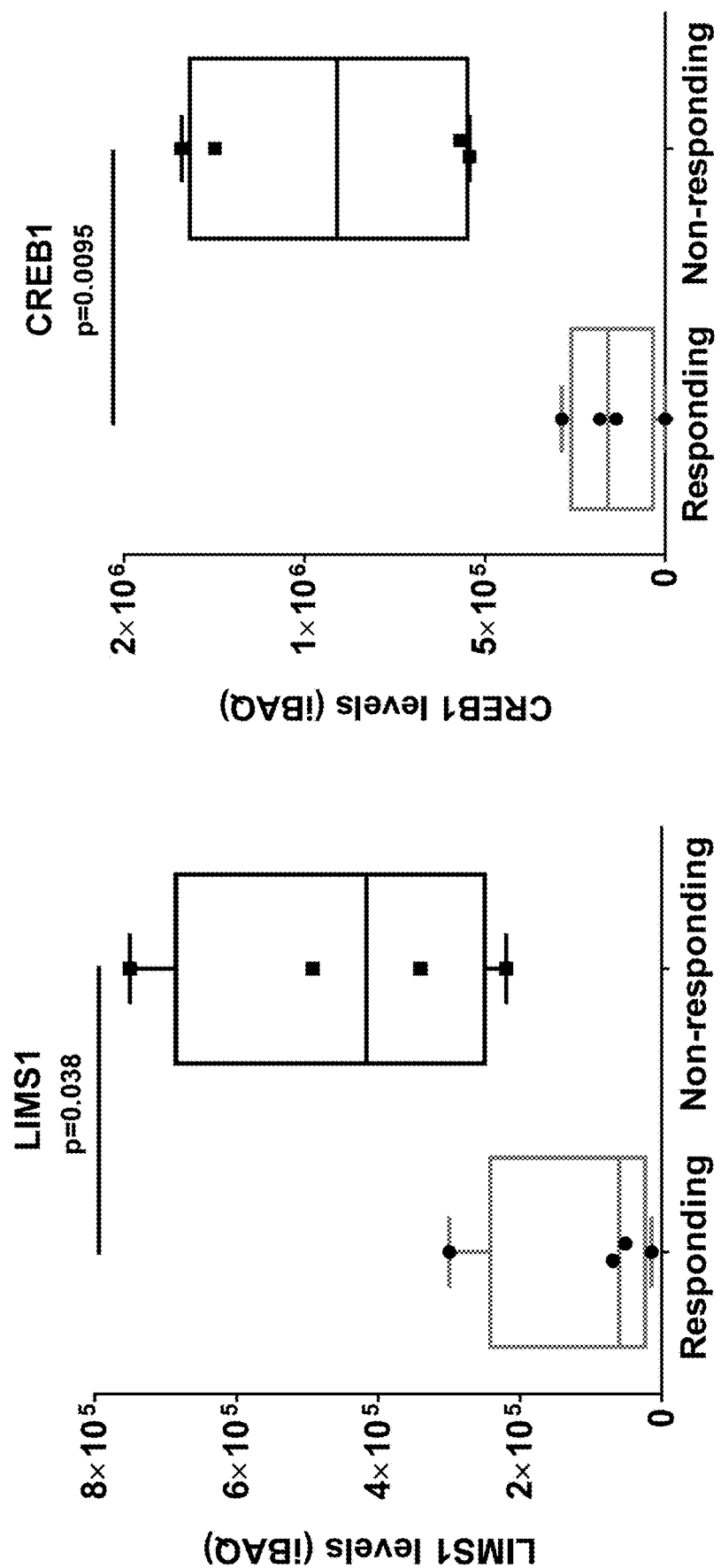
Figure 3E:
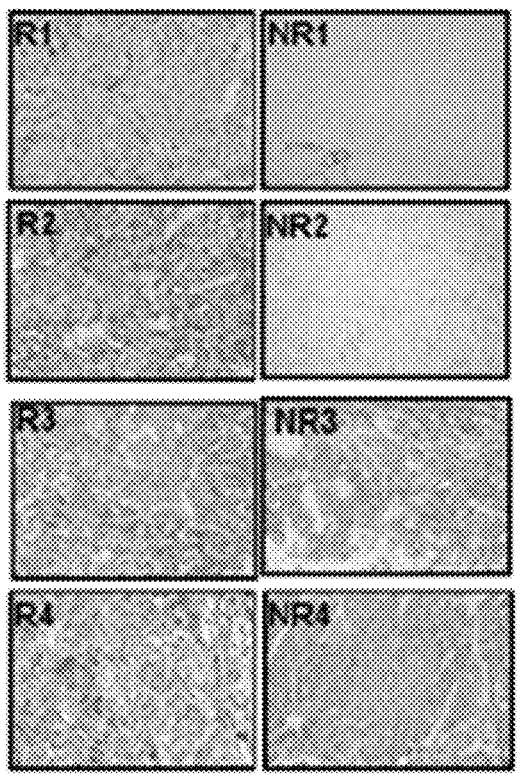
Figure 3E:
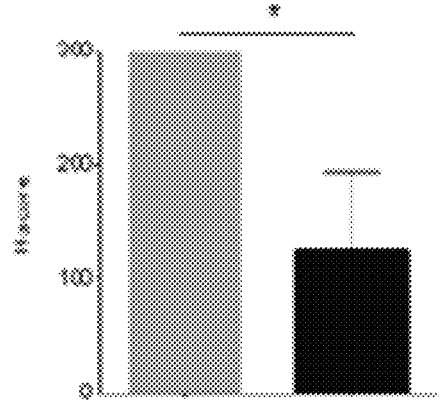
Figure 3F:
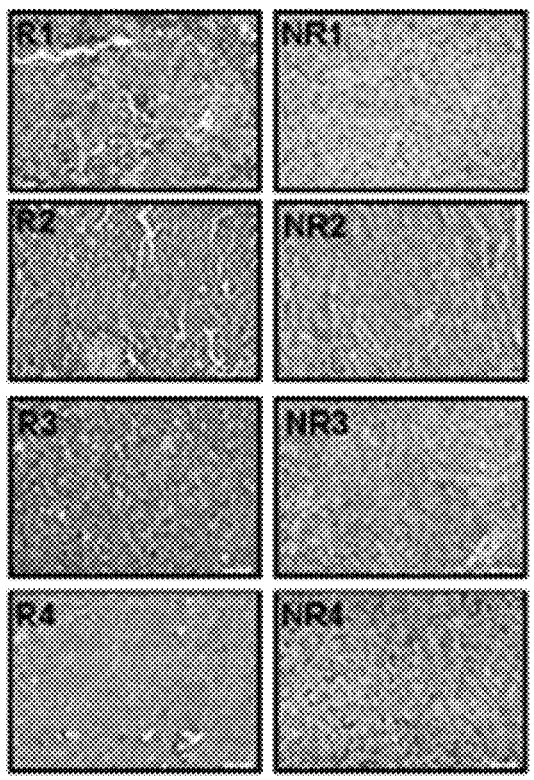
Figure 3F:
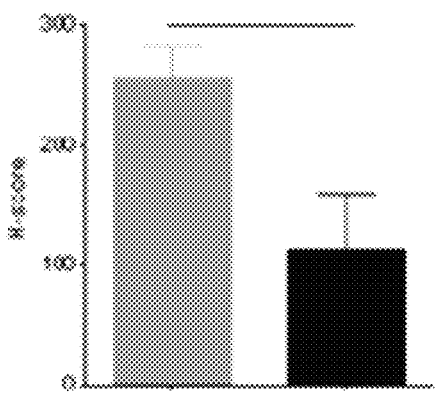

One key component of this network was lower relative levels of E-cadherin and CD63 in non-responding tumors (FIGS. 3D-3F). Interestingly, Hugo and colleagues recently reported lower levels of E-cadherin transcripts in non-responding (versus responding) pretreatment tumors to PD-1 blockade in melanoma. We confirmed the reduced E-cadherin and CD63 proteins via immunohistochemistry and H-score quantitation (FIGS. 3E, 3F). Non-responding tumors 1 and 2 showed almost complete loss of E-cadherin, which was reflected in an absent/low signal (iBAQ intensity-0) upon proteomic analysis. Non-responding tumors 3 and 4 showed positive staining for E-cadherin (reflected in the iBAQ intensity value; albeit much lower than any of the responding tumors). These results suggest patient stratification will require a panel of markers as would be anticipated with tumor heterogeneity. E-cadherin is a calcium-dependent cell-cell adhesion molecule, which has a vital role in epithelial tissue organization and tumor suppression. Loss of E-cadherin is considered to be a core event in EMT[18]. CD63 is a suppressor of melanoma tumor progression and has been shown to be a negative driver of epithelial-to-mesenchymal transition (EMT)[19]. The chemokines CXCL4 and CXCL12 were elevated in responding tumors. CXCL4 and CXCL12 were also elevated on the chemokine array >1.5 fold (FIG. 1E).

Figure 4A:
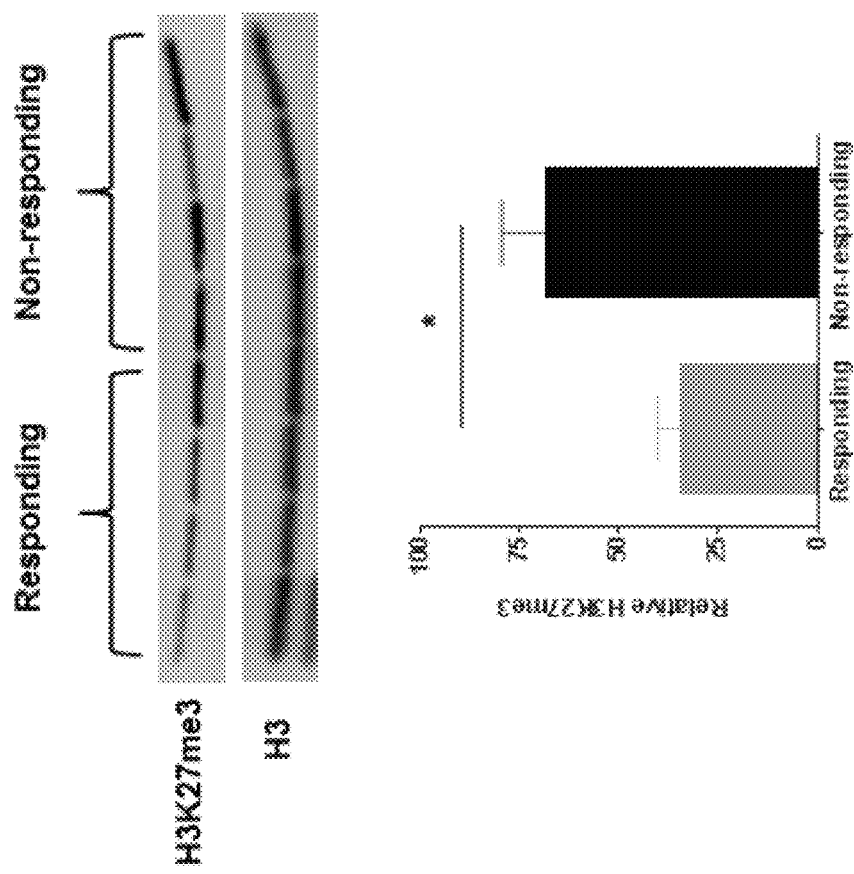
FIGS. 4A-4E show H3K27me3 is upregulated in ICI non-responding tumors.
Figure 4B:
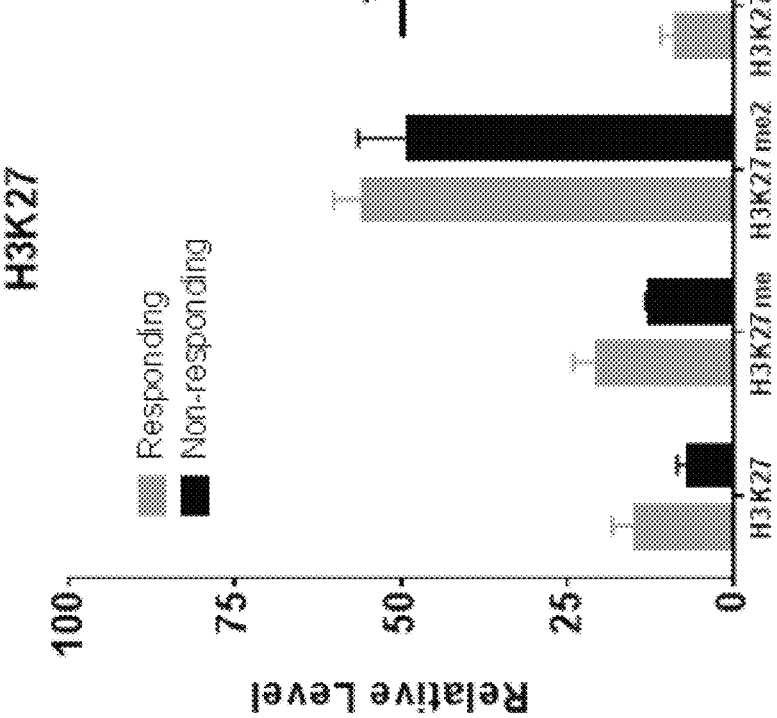
Figure 8:
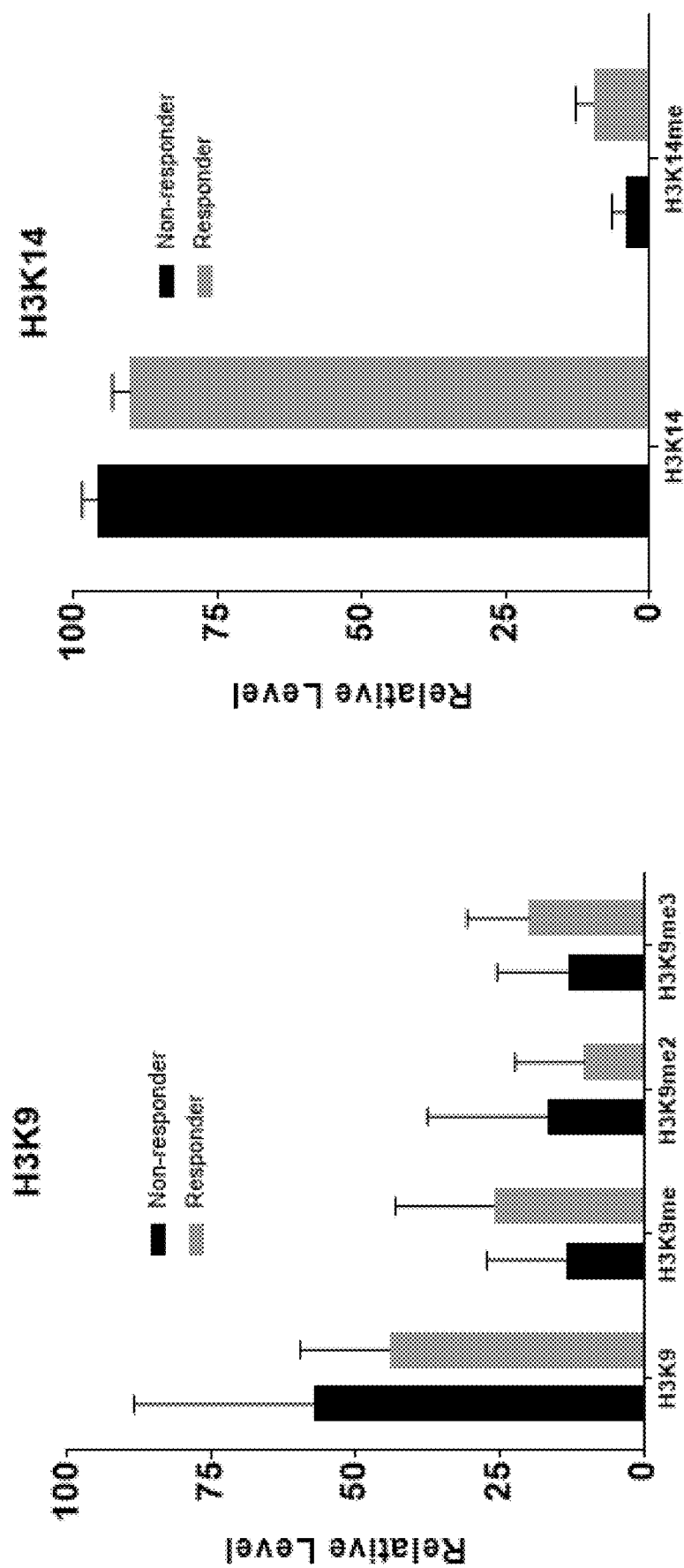
FIG. 8 shows Histone H3 comparisons in responders and non-responders. Quantitative analysis of histone peptide intensities in responding tumors relative to non-responding tumors. Standard error was calculated for the specific peptide in the biological replicate samples as displayed in the chart. n=4 for responding and non-responding tumors (*p<0.05).
Figure 8:
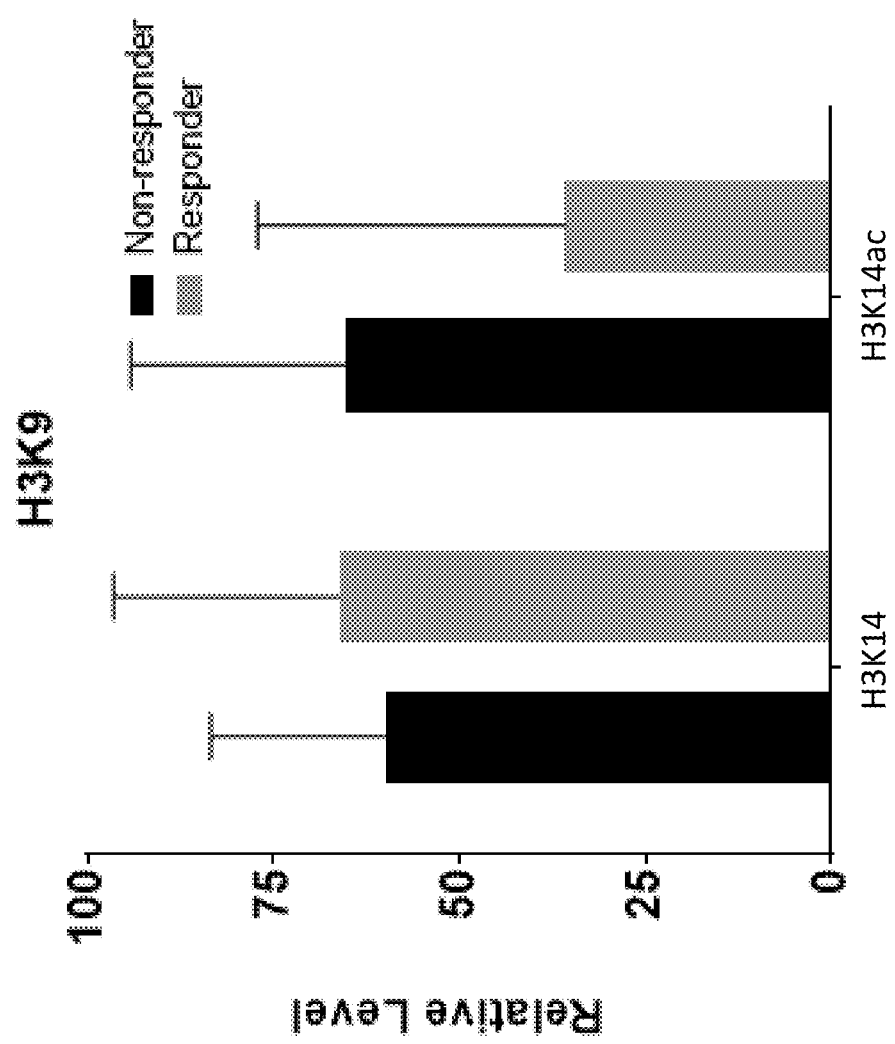
Figure 8:
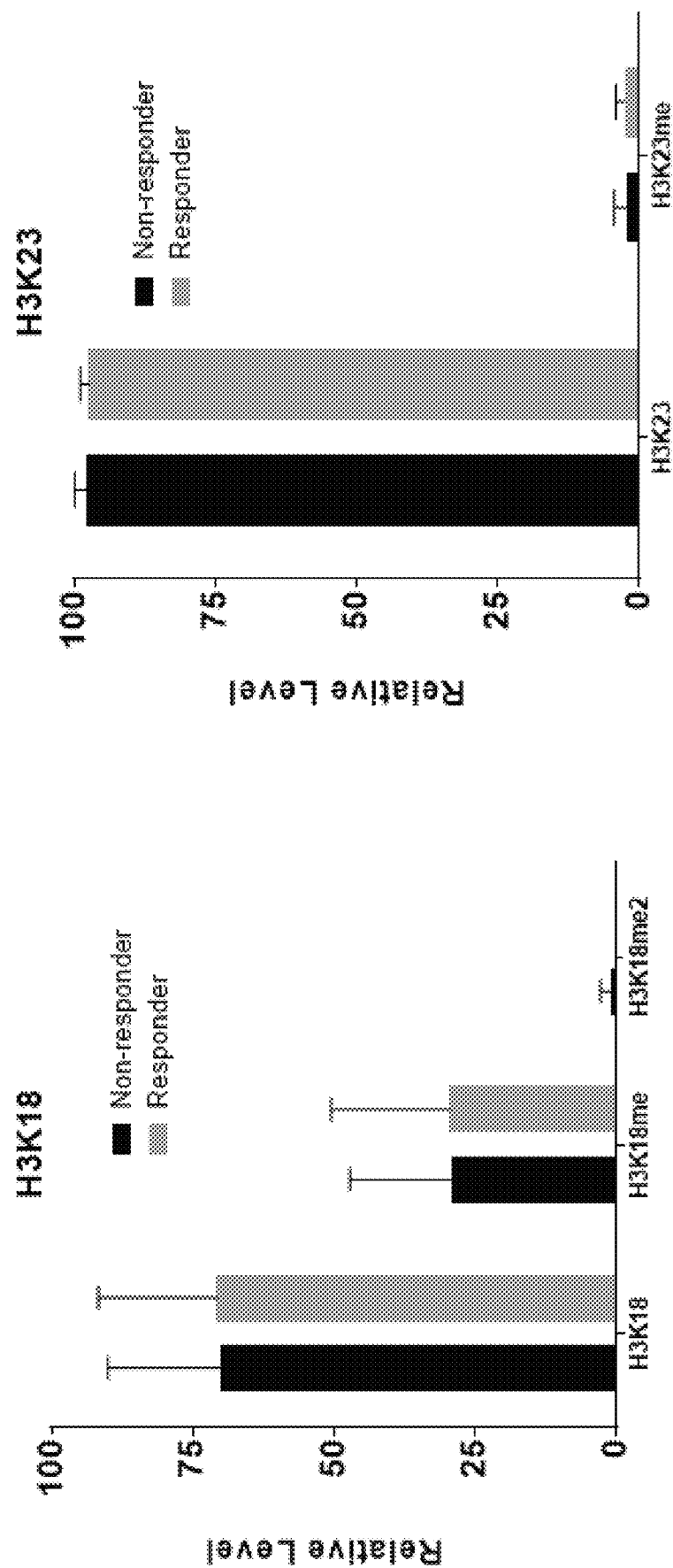
Figure 8:
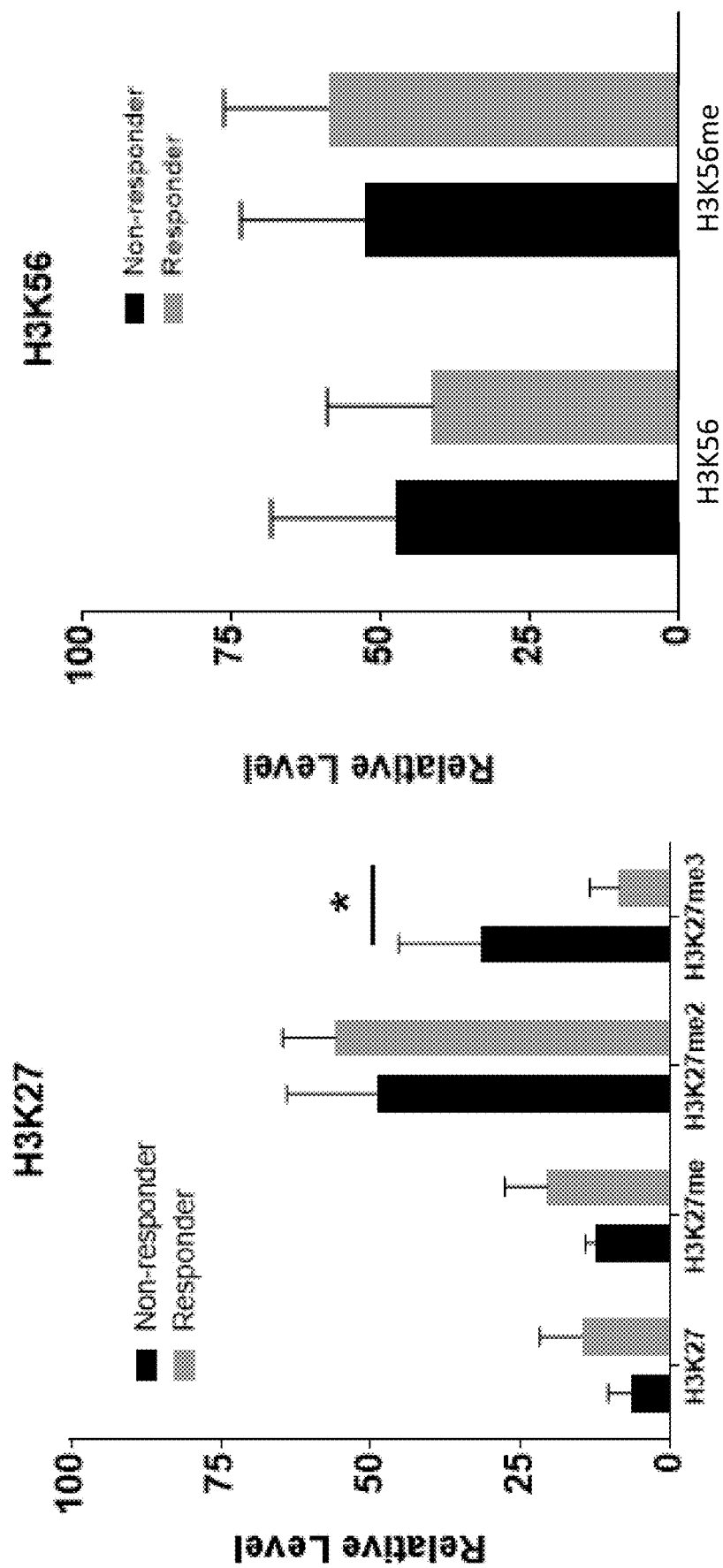
Figure 8:
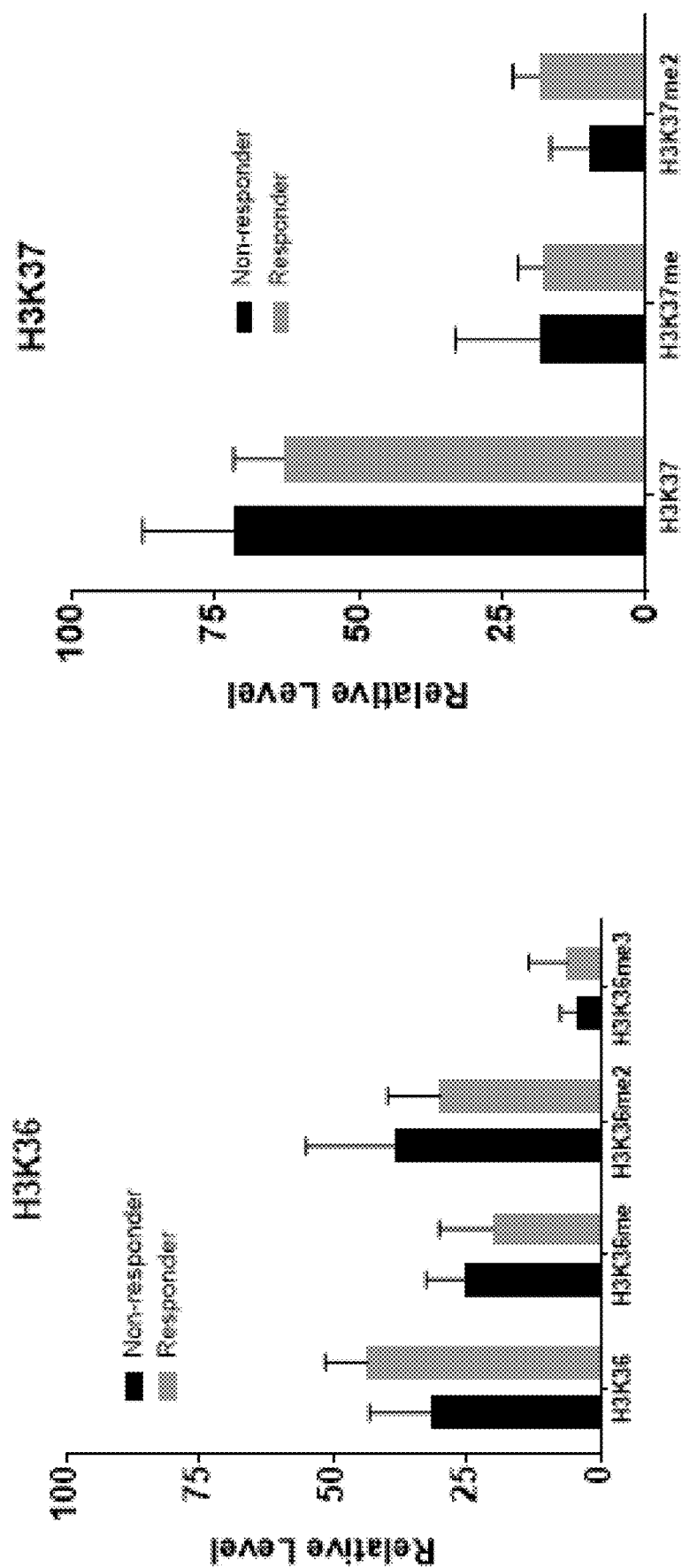
Figure 8:
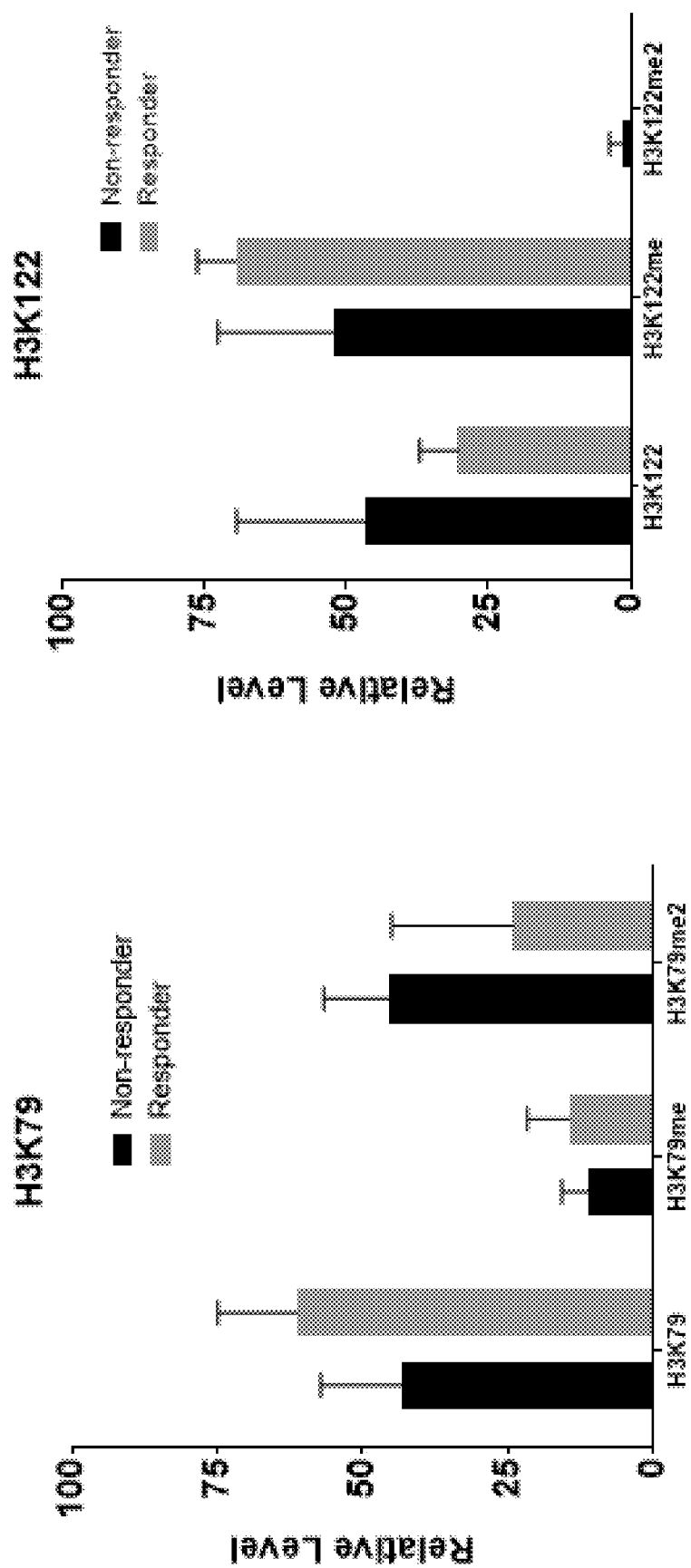
Figure 9:
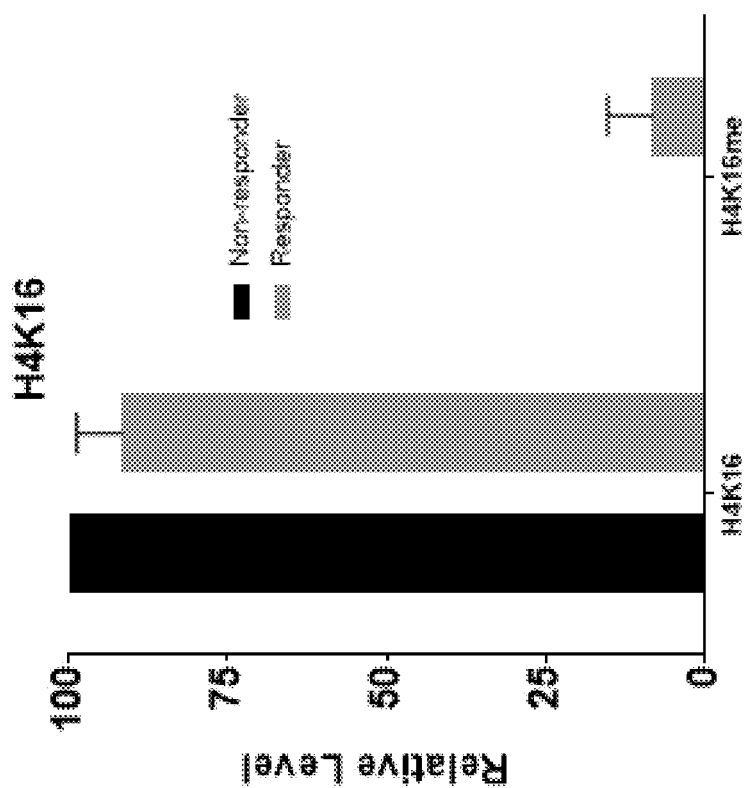
FIG. 9 shows Histone H4 comparisons in responders and non-responders. Quantitative analysis of histone peptide intensities in responding tumors relative to non-responding tumors. Standard error was calculated for the specific peptide in the biological replicate samples as displayed in the chart. n=4 for responding and non-responding tumors (*p<0.05).
Figure 9:
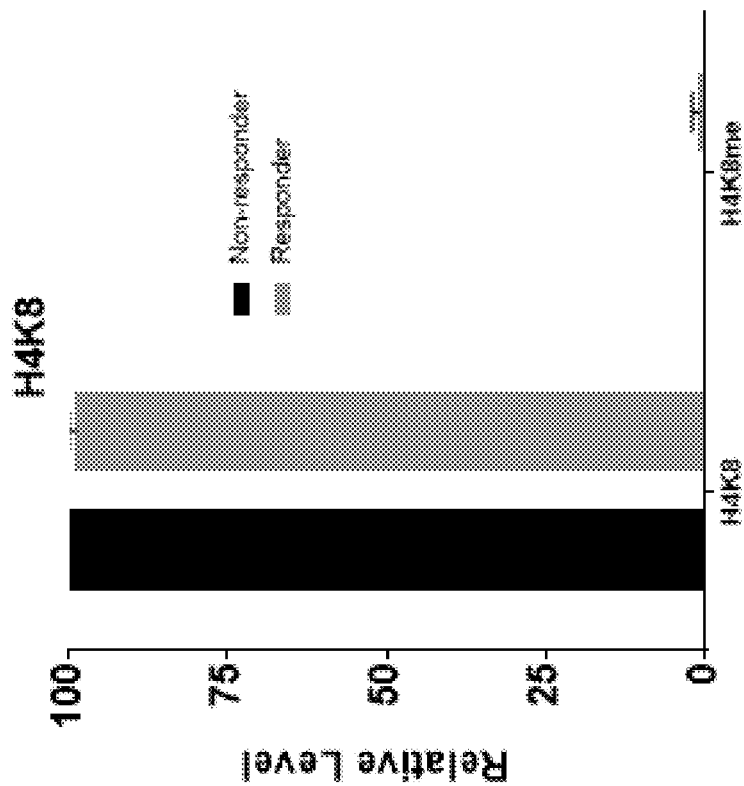
Figure 9:
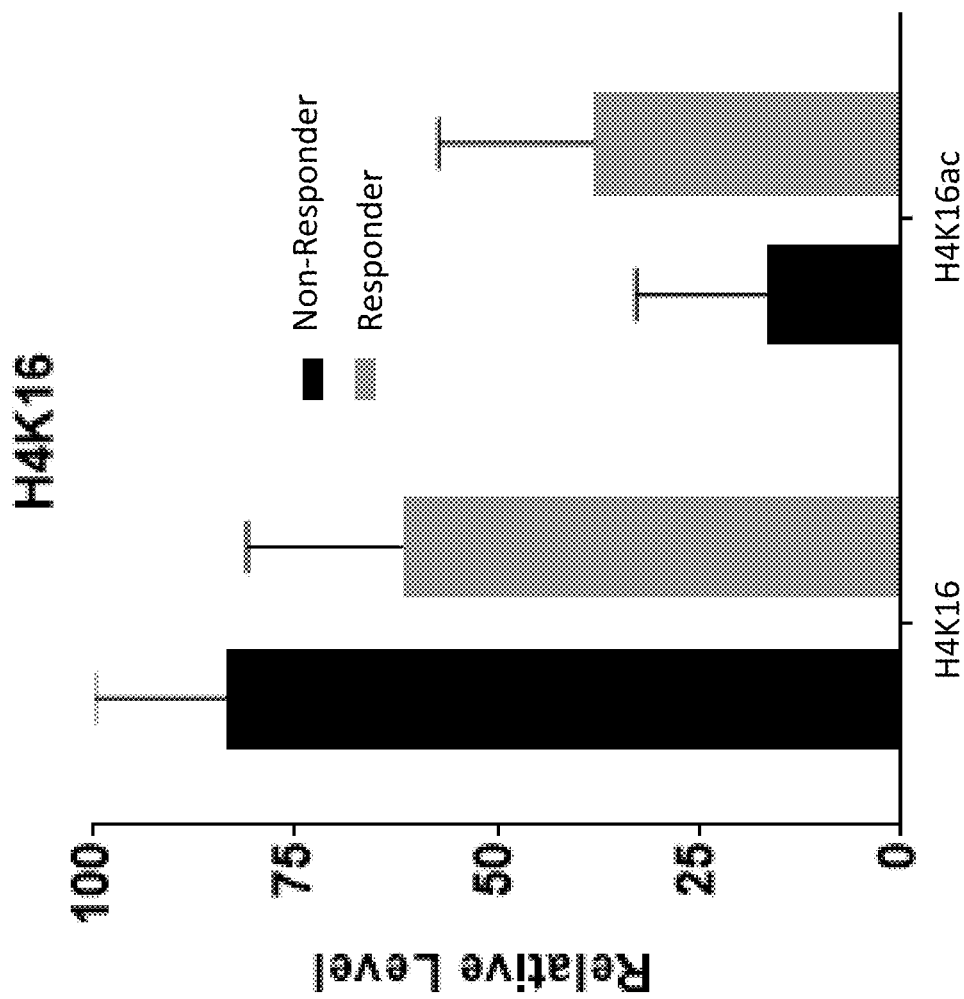
Figure 9:
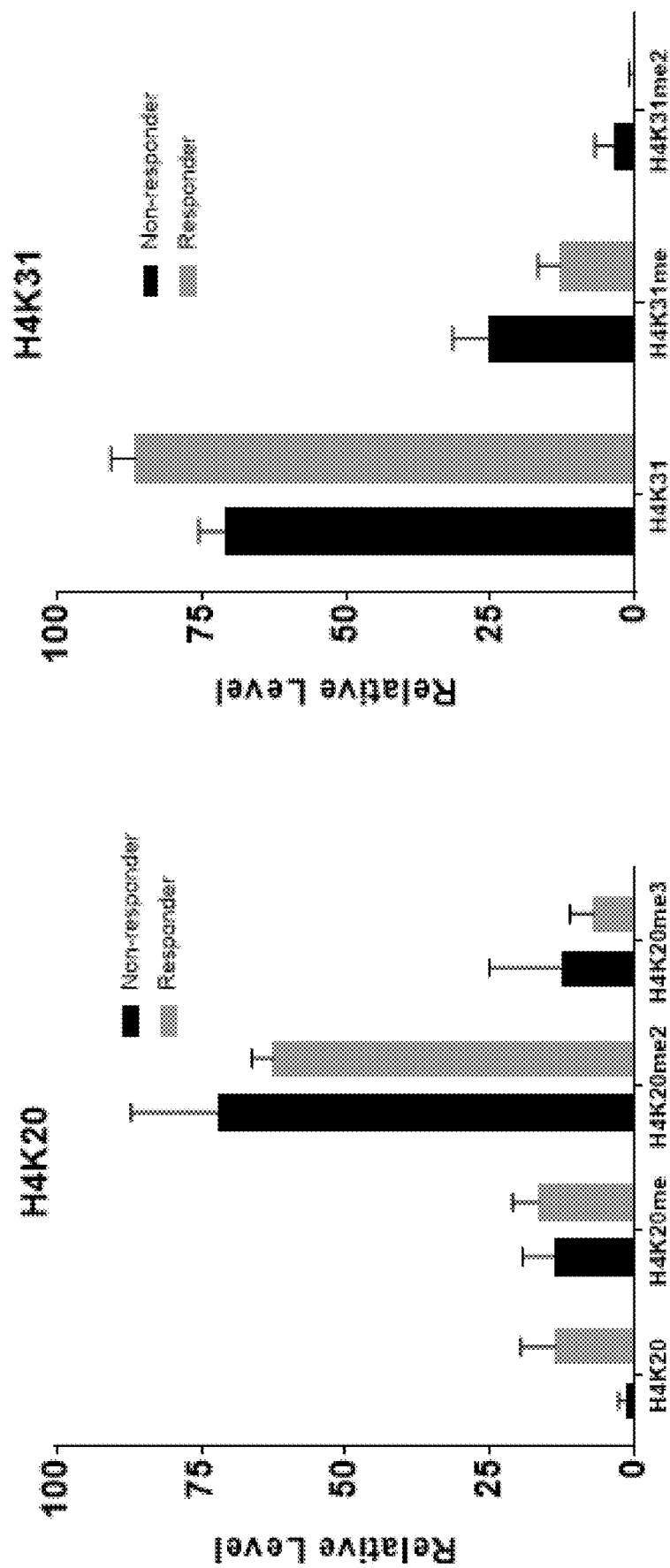
Figure 9:
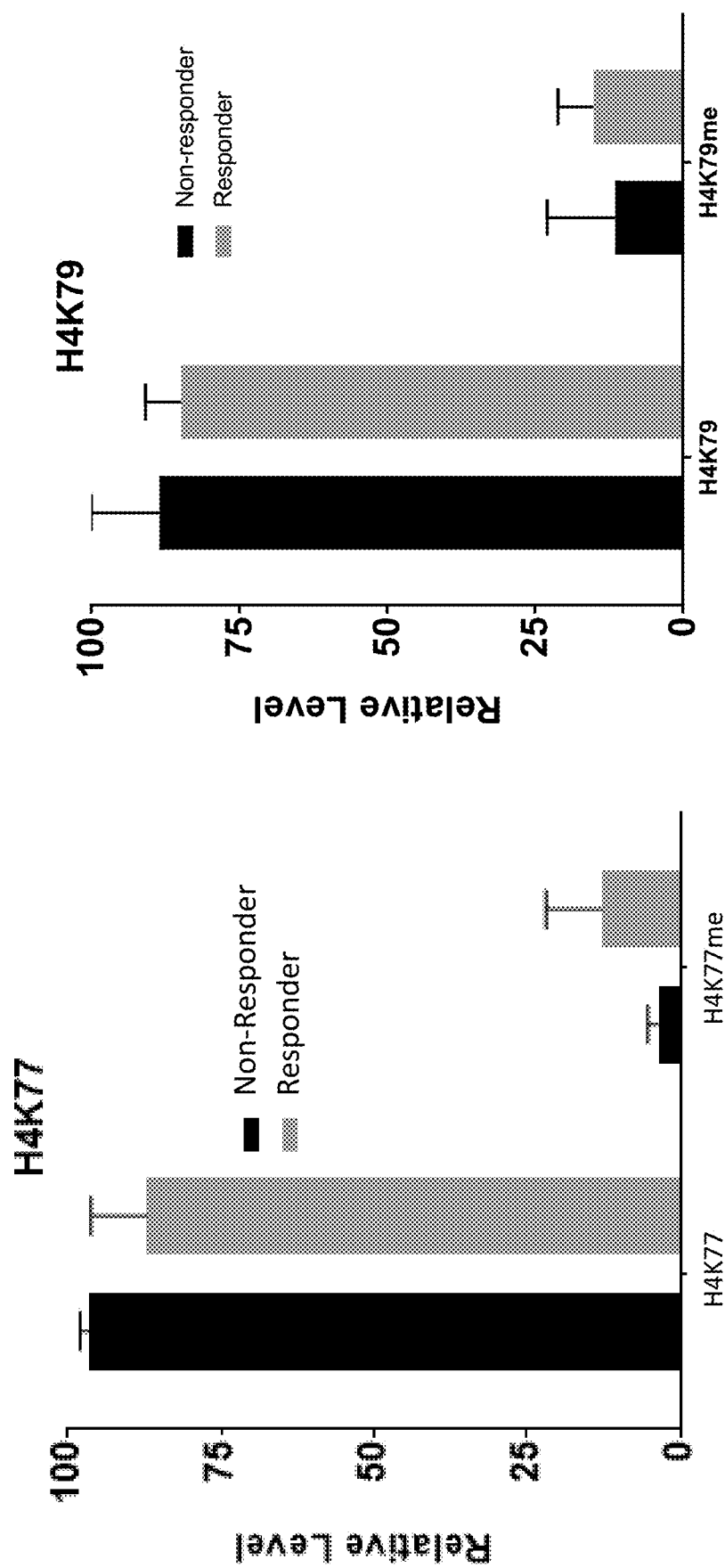
Figure 10:
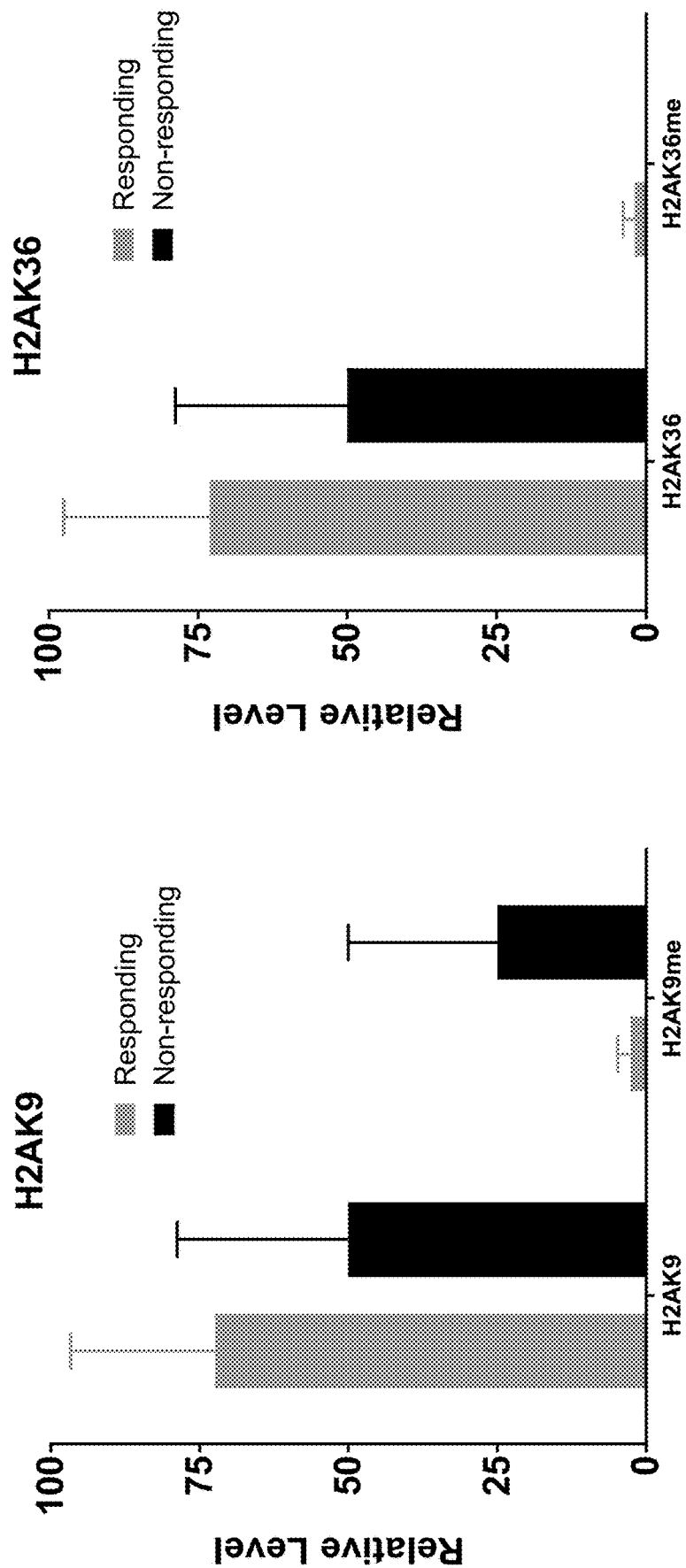
FIG. 10 shows Histone H2A and H2B comparisons in responders and non-responders. Quantitative analysis of histone peptide intensities in responding tumors relative to non-responding tumors. Standard error was calculated for the specific peptide in the biological replicate samples as displayed in the chart. n=4 for responding and non-responding tumors (*p<0.05).
Figure 10:
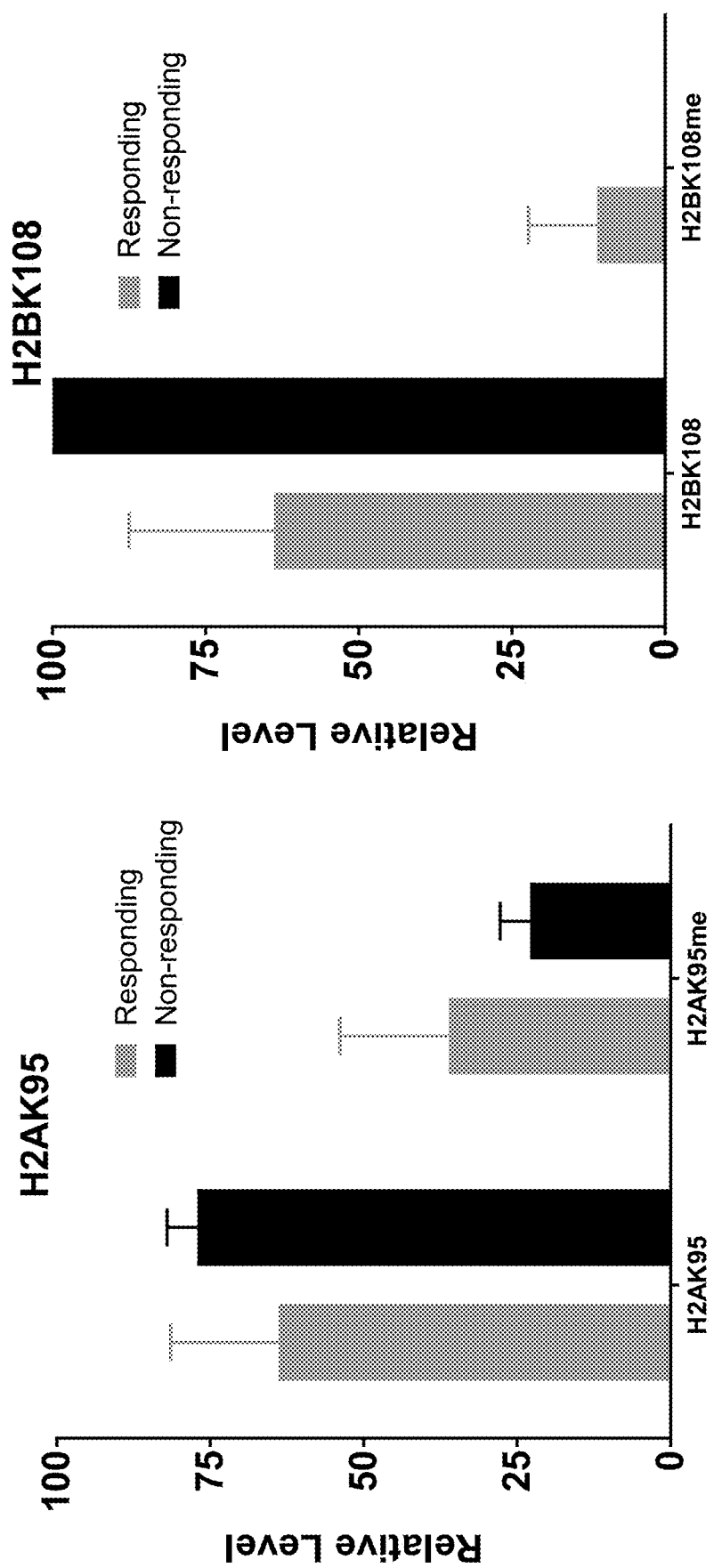
Figure 10:
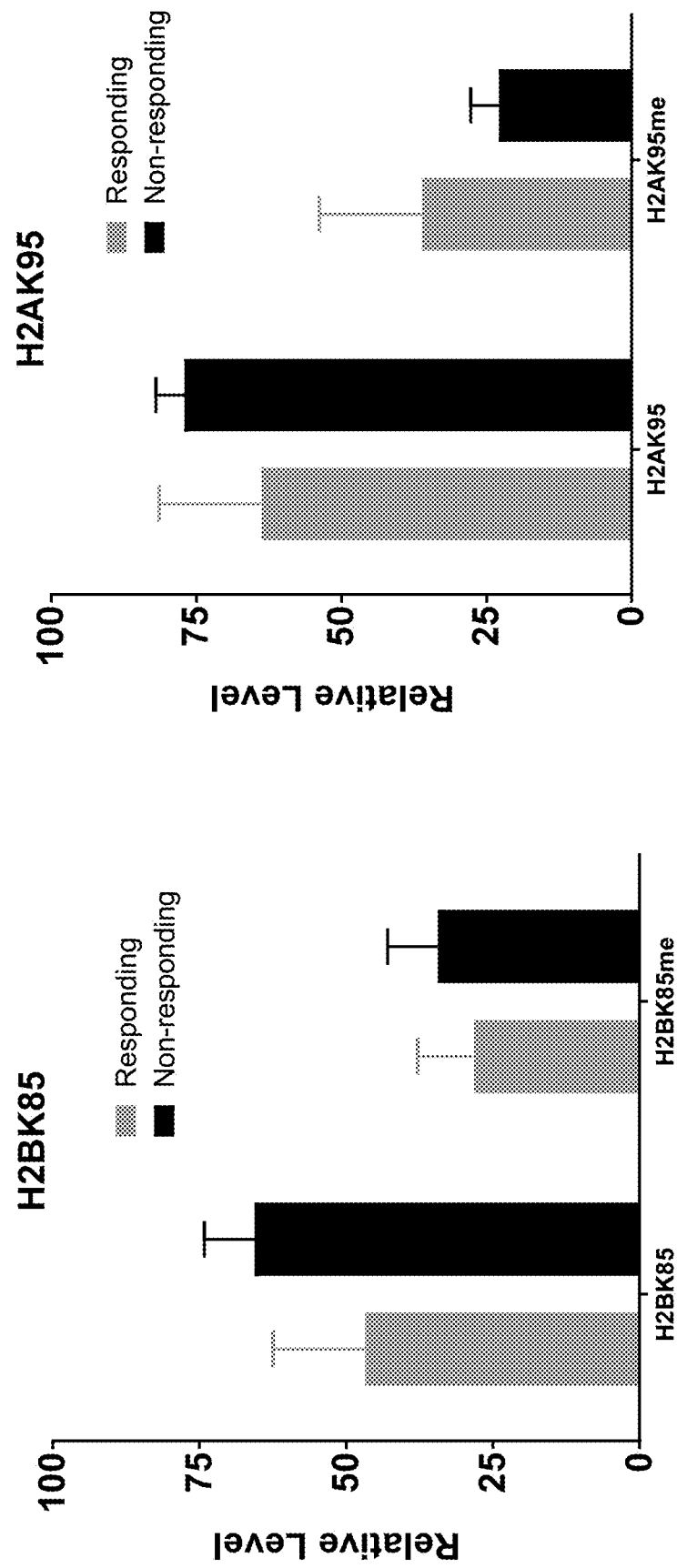
Figure 11:
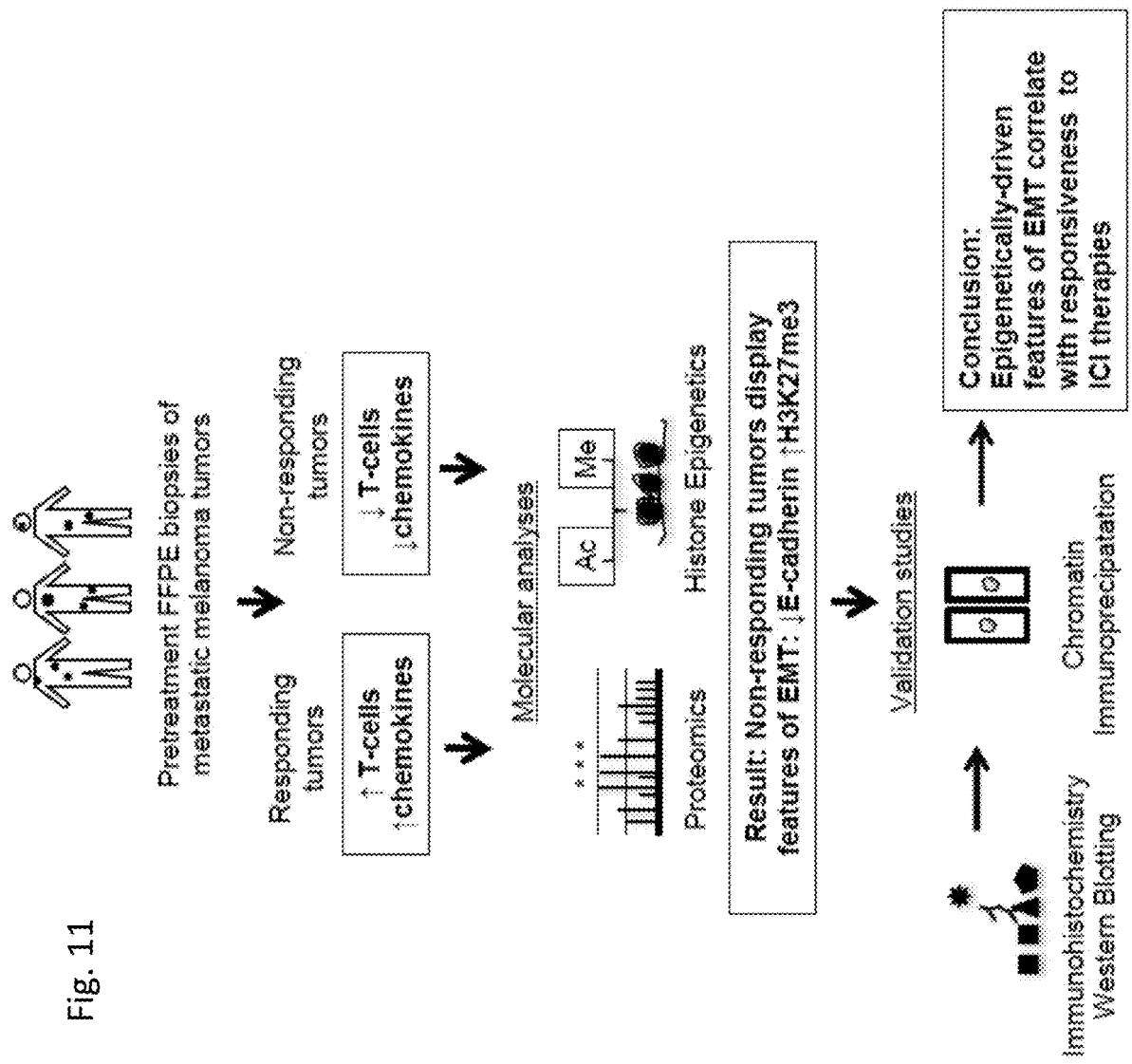
FIG. 11 shows a Graphical Abstract showing the studies performed in the Examples.

Identification of mis-regulated proteins between responding tumors and non-responding tumors lead us to study potential points of mis-regulation. Aberrant histone post-translational modifications (PTMs) are now widely recognized as critical events in the development and progression of human cancers, such as melanoma[20,21]. However, the presence of epigenetic mis-regulation in the context of response to immune checkpoint inhibitors is unknown. Therefore, we then addressed whether histone PTMs would differentiate between responding versus non-responding tumors and if we could identify any points of mis-regulation of our candidate proteins. Histones were isolated for MS/MS analysis as described previously[9]. Peptide precursor ion intensity-based, label-free quantitation was used to measure relative amounts of unmodified and post-translationally modified histone peptides. We identified 61 uniquely modified histone peptides across H3, H4, H2A, and H2B in the 8 pre-treatment tumors. For this analysis, we focused on common histone PTMs including lysine methylations and acetylations. We plotted relative levels for each set of histone peptides (FIGS. 8-10 all parts). Only one histone PTM was significantly different (p<0.05) in bulk abundance between responding and non-responding tumors. Histone H3 lysine (27) trimethylation H3K27me3 was significantly elevated (p=0.019) in non-responding tumors by Student's T-test (FIG. 4A). Immunoblot analysis and densitometry confirmed the elevated levels of H3K27me3 in non-responding tumors (FIG. 4B). H3K27me3 is a repressive mark catalyzed by the lysine methyltransferase EZH2, which is implicated in the pathogenesis and progression of various cancers, including melanoma. EZH2 has been shown to play roles in melanoma pathogenesis via silencing of tumor suppressors. Additionally EZH2 is a known driver of EMT22.

Figure 4E:
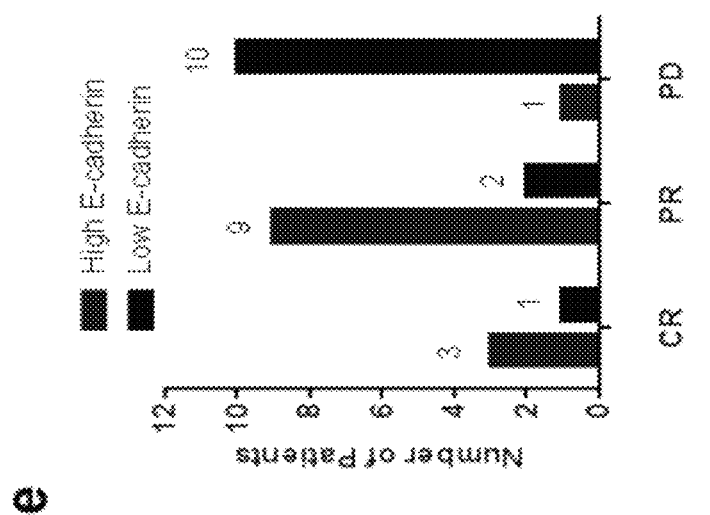
Figure 4D:
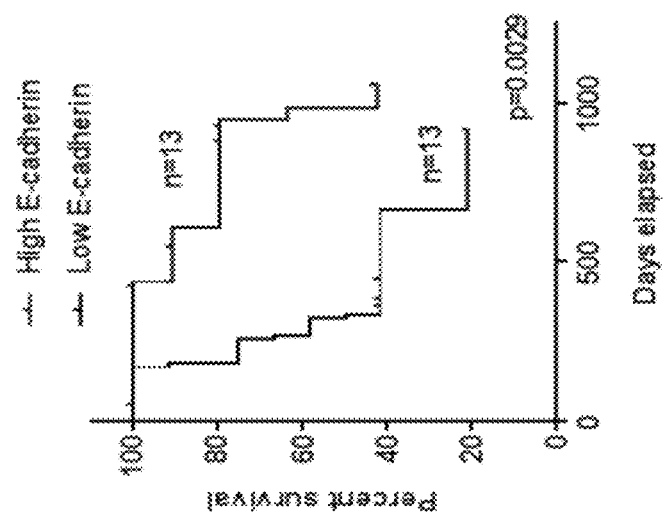
Figure 4C:
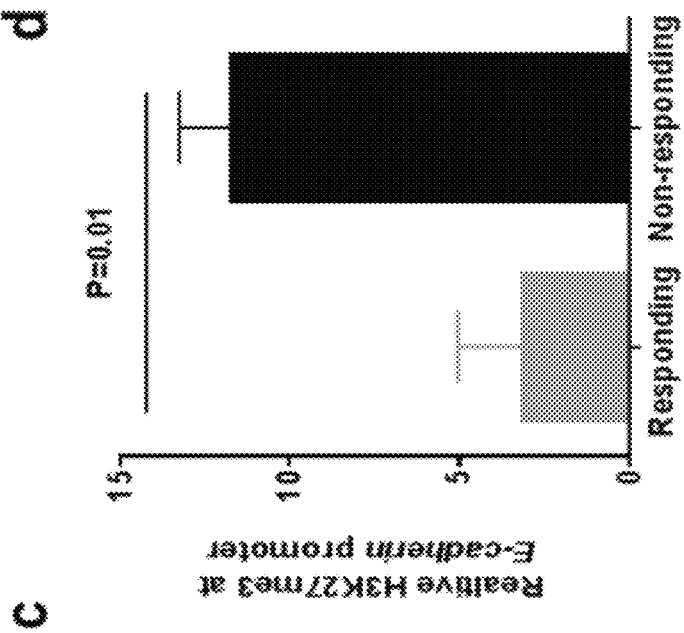

Since we identified the H3K27me3 mark elevated at a bulk level in non-responding tumors, we then sought to genomically correlate the presence of this repressive histone mark with mis-regulation of our candidate protein. To determine whether the down-regulated E-cadherin in non-responding tumors was a direct effect of H3K27me3 occupancy at the E-cadherin promoter, we performed ChIP to determine the relative level of H3K27me3 at the E-cadherin promoter. ChIP was performed using the 4 responding and 4 non-responding pretreatment tumor FFPE tissues. The non-responding tumors exhibited higher H3K27me3 at the promoter of E-cadherin (P=0.01) (FIG. 4C). We conclude that EZH2 is driving the epigenetic program present in the non-responding tumors within our sample set.

Loss of epithelial phenotype in melanoma tumors via direct silencing of E-cadherin by H3K27me3 in our set of non-responding tumors led us to examine other datasets to determine consequence and generalizability of these findings. We used a transcriptomic data set produced by Hugo et al. 2016 (data accessible at NCBI GEO database, accession GSE78220) which consisted of pretreatment melanoma tumor samples from patients undergoing anti-PD1 therapy[23]. We separated E-cadherin mRNA levels by the median value and plotted survival versus high or low E-cadherin (n=13 per group). Patients in the top half of levels of E-cadherin transcripts had significantly higher overall survival (P=0.0029) versus patients in the bottom half of E-cadherin transcripts (FIG. 4D). Next, we compared the top half and bottom half E-cadherin groups to response designation (FIG. 4E). Strikingly, only 1 of 13 patient who had an E-cadherin transcript level in the top half experienced disease progression, while 10 of 13 patients in the lower half of E-cadherin transcript levels experienced disease progression.

Dissemination and proliferation of a primary tumor to distant sites likely requires epithelial mesenchymal transition and escape from immunosurveillance. Upon establishment of metastatic lesions, data suggests the plasticity of the epithelial phenotype enables melanoma tumor cells to transition through multiple rounds of EMT and MET resulting in varied phenotypes along this spectrum[18]. Failure of T-cells to mount a response against certain metastatic tumors appears to preclude clinical benefits from checkpoint blockade therapies and is indicative of tumor phenotypes which allow for immune-escape (FIG. 1 all parts)[13,24]. Reduced expression of chemokines by tumors is one potential explanatory mechanism by which immunosurveillance could breakdown. On a more global scale, it appears chemokine expression is just one sign of a larger cellular program as evidenced by transciptomic and proteomic data (FIG. 2 all parts)[12]. Mesenchymal transition in non-responding tumors appears to correlate with lack of responsiveness to immune checkpoint inhibitors. Moreover, observation of H3K27me3-mediated silencing of E-cadherin led us to ask if the protein-level evidence could be verified at the transcriptomic level (FIG. 3 all parts). For melanoma patients not treated with ICI therapies E-cadherin levels trend with, but do not significantly correlate with overall survival[25]. However, we find patients who have low levels of E-cadherin transcripts in their pretreatment tumors have a high risk of innate resistance to immune checkpoint blockade and disease progression (FIG. 4 all parts). In the current era of immune checkpoint inhibitor therapy, renewed analysis of existing markers, along with identification of mis-regulated proteins in non-responding or responding tumors may serve as a powerful tool for patient stratification and responsible use of medical resources. Furthermore, it may be ultimately possible to modulate the epigenetic landscape driving the mesenchymal transition in certain tumors. We conclude that epigenetic modulation aimed at driving tumors towards a more epithelial phenotype could perhaps positively influence responsiveness to immune checkpoint inhibition.

Methods

Sample Acquisition

Pretreatment tumor biopsies were collected and separated into responding and non-responding groups. Responding tumors were from patients who achieved complete responses (CR) on ICI therapies. Non-responding tumors were from patients who had disease progression on therapy. These response categories were based upon irRECIST. Patient and sample demographics can be found in Table 2.

TABLE 2

Demographic and clinical characteristics of patients in the study. There were 8 total cases selected 4 responding; 4 non-responding as determined by irRECIST. There were 4 females and 4 males. The age range was 31-92.

| Variable | Responding | | | | Non-responding | | | |
|---|---|---|---|---|---|---|---|---|
| | R1 | R2 | R3 | R4 | NR1 | NR2 | NR3 | NR4 |
| Sex | Female | Male | Male | Female | Male | Male | Female | Female |
| Age | 46 | 78 | 78 | 86 | 72 | 31 | 92 | 68 |
| Location of metetsatic melanoma | lymph node | skin (leg) | lung | liver | lung | small intestine | colon | skin (foot) |
| BRAF Mutation | No | Yes | Yes | No | Yes | Yes | No | Yes |
| Primary Treatment | ipilimumab | combination[1] | combination[1] | pembrolizumab | ipilimumab | ipilimumab | ipilimumab | ipilimumab |
| Secondary Treatment | — | — | — | — | BRAF inhibitor | BRAF inhibitor | pembrolizumab | pembrolizumab |
| Third Treatment | — | — | — | — | nivolumab | combination[1] | | |
| Discontinuation due to toxcity | Yes | | | | | | | |
| LDH | normal | normal | normal | normal | normal | elevated | normal | normal |
| Overall Survival-months[2] | 15 | alive, CR[3] | alive, CR[3] | alive, CR[3] | 18 | 22 | 26 | 17 |

Notes:
[1]Combination of ipilimumab plus nivolumab.
[2]Overall survival was calculated from date of metastatic disease to the date of death or censoring of data.
[3]Complete Response, as of Dec. 14, 2016.
Source: UAMS Hospital Participating oncologists identified and flagged metastatic melanoma patients treated with the immunotherapy drugs ipilimumab, nivolumab, or pembrolizumab as either "responders" or "non-responders" (UAMS IRB-approved study #204543). The response designation was made by the judgment of the attending clinicians and was based upon clinical and radiographic evidence (PET-CT scans at 3, 6 and 9 months) as designated by the Immune-Related Response Criteria (irRECIST)[26].

The response designation was made by the judgment of the attending oncologist and was based upon clinical and radiographic evidence as designated by the Immune-Related Response Criteria (irRC). Patients treated with ICI therapies were evaluated at 3 months and 6 months by clinical exam and PET-CT. If immune-related response criteria were met at these intervals patients were designated "responders."

Pathology records were collected for the 21 flagged patients (11 non-responders and 13 responders). Records were then searched for pre-treatment metastatic lesion biopsies which tested positive for melanoma. Fine needle aspirations and biopsies without sufficient tissue for slide preparation were excluded. All the tissue blocks belonging to remaining biopsies were then retrieved from the University of Arkansas for Medical Sciences Department of Pathology archives. Original H&E stained slides from tissue blocks were then examined by a collaborating dermatopathologist in order to select the tissue block containing the most cross-sectional area of melanoma tumor. Selected tissue blocks were cut into twenty 5 µm sections on positively charged glass slides and designated for proteomic and immunohistochemistry analyses. Tumor boundaries for each case were demarcated on the slides by a dermatopathologist. Eight cases were selected for this study. Demographic and treatment data can be found in Table 2.

FFPE Tissue Processing

Using the methods previously described by our laboratory specimens were deparaffinized and formalin cross-linking was reversed[15]. After reversal of formalin cross-linking, the interface between normal tissue and metastatic melanoma was identified and demarcated on H&E and immunohistochemical-stained slides by a dermatopathologist. Then cells were collected with a needle to ensure the vast majority of cells collected were cells of interest (i.e., metastatic melanoma cells). To normalize the amount of protein across the samples, tumor area on slides was calculated and normalized, and a BSA assay was performed to load equal amounts of samples for gel electrophoresis. Thirty microliters of sample were loaded per lane and resolved by 4-20% SDS-PAGE (Invitrogen gels). ImageJ was used to normalize protein loading and gels were rerun with normalized load amounts (FIG. 1A). The gel was Coomassie-stained, cut into 24 sections and subjected to in-gel trypsin digestion as described previously by our lab[9]. Gel slices containing protein were destained in 50% methanol, 100 mM ammonium bicarbonate, followed by reduction in 10 mM Tris[2-carboxyethyl] phosphine and alkylation in 50 mM iodoacetamide. Gel slices were then dehydrated in acetonitrile, followed by addition of 100 ng porcine trypsin (Promega) in 100 mM ammonium bicarbonate and incubation at 37° C. for ~14 hours. Peptide products were then acidified in 0.1% formic acid to quench the trypsin digestion.

Immunohistochemistry

FFPE tissue slides from the same pool of slides cut for proteomic analysis were used for validation of mass spectrometry data. To expose antigens, slides were heated to 120° C. for 20 s in a Decloaking Chamber™ (Biocare Medical, Concord, Calif.) using 10 mM sodium citrate buffer, pH 6.0. Staining was performed using Vectastain Elite ABC kit (Vector Laboratories, Burlingame, Calif.). The following antibodies were used for staining: anti-E-cadherin (1:400; rabbit polyclonal, CST, catalog no. 3195) anti-CD63 (1:50; rabbit polyclonal, Sigma, catalog no. HPA010088) anti-SCGB2A1 (1:50; rabbit polyclonal, Sigma, catalog no. HPA034584) anti-DNAJC11 (1:50; rabbit polyclonal, Sigma, catalog no. HPA028705). Slides were counterstained with Mayer's hematoxylin (Thermo Fisher Scientific) for 1 min. Scoring of FFPE tissue samples was performed in a blinded fashion by a board-certified dermatopathologist (without access to the response status).

IHC Cell Counting

Images were taken at 20× objective on a life technologies Evos FL Auto microscope. Tumor margins were identified and demarcated by a collaborating dermatopathologist. A total of 20 images were taken of both the CD3+ and the CD8+ stained tumors. 10 images were selected at random from the intratumoral region and 10 images from the invasive margin using the Evos FL Auto. The images were then loaded into ImageJ and converted into binary (16-bit). Next, the threshold was converted to black and white and adjusted in order to maximize cell separation and reduce background. Following adjustment, watershed was applied to separate touching cells and analyze particles was used with adjustments made to size and circularity in order to quantify the number of cells present. This method was manually verified on each image by 2 examiners who performed a manual count in a selected stained region and confirmed the accuracy of that count upon each run. Regions were selected and manually counted and compared to optimize the parameters associated with the threshold adjustment and particle analysis.

Protein Arrays

Human chemokine antibody arrays (Proteome Profiler, R&D Systems; Ary017) were used to analyze chemokine expression profiles according to the manufacturer's protocol. Briefly, tumor tissue lysates were mixed with a biotinylated detection antibody cocktail at room temperature for 1 hour while the array membrane was blocking with blocking buffer provided by the manufacturer. Array membranes were incubated with the tumor tissue lysate/antibody cocktail overnight and then exposed for ten minutes the following day to X-ray film. High resolution film images were scanned and quantitation was determined by mean pixel density using Western Vision Quick Spots Tool.

Mass Spectrometry and Protein Identification

Tryptic peptides were separated by reverse phase Jupiter Proteo resin (Phenomenex) on a 200×0.075 mm column using a nanoAcquity UPLC system (Waters). Peptides were eluted using a 30 min gradient from 97:3 to 65:35 buffer A:B ratio. [Buffer A=0.1% formic acid, 0.5% acetonitrile; buffer B=0.1% formic acid, 99.9% acetonitrile.] Eluted peptides were ionized by electrospray (2.35 kV) followed by MS/MS analysis using collision induced dissociation on an Orbitrap Fusion Tribrid mass spectrometer (Thermo) in top-speed data-dependent mode. MS data were acquired using the FTMS analyzer in profile mode at a resolution of 240,000 over a range of 375 to 1500 m/z. MS/MS data were acquired following HCD activation using the ion trap analyzer in centroid mode and normal mass range with precursor mass-dependent normalized collision energy between 28.0 and 31.0.

A total of 4318 proteins were identified (FDR <1%) by MaxQuant (Version 1.5.3.30) with the following search parameters: precursor ion tolerance 2 ppm, fragment ion tolerance 0.50 Da, fixed modifications of carbamidomethyl on cysteine, variable modifications of oxidation on methionine and N-terminal acetylation, and 3 missed cleavages possible with trypsin. We first searched a contaminants database (262 entries) to identify common contaminating proteins followed by a main search using the UniProtKB database specific for *Homo sapiens* (151,869 entries). Label-free quantitation using iBAQ normalization was performed in MaxQuant.

Quantitative Analysis of Protein Levels

To determine the significantly differentiating levels of proteins between responding and non-responding tumors a label-free quantitation approach was used. iBAQ (Intensity-based absolute quantification) sums raw peptide intensities belonging to a protein, divides them by the number of theoretical tryptic peptides (between 6-30AA) produced by a trypsin digestion[27]. This method takes a value proportional to mass (intensity) and converts it to a value highly correlated with protein abundance; thereby normalizing for protein molar concentration[27].

Hierarchical Clustering

A heat map was generated using Hierarchical Clustering Explorer (HCE version 3.0) with all 106 significant proteins, the average linkage method, and Euclidean distance metric. The responding and non-responding tumors were clearly separated into two separate clusters based on these significantly differentiating proteins. Up- or down-regulated proteins are indicated in red and blue, respectively (FIG. 2B).

Pathway Analysis

Ingenuity pathway analysis (IPA) was used to identify known pathways containing the proteins of interest. The significant protein list was uploaded into IPA and the Ingenuity Knowledge Base was used as the reference set. The default parameters were used for the analysis including a hypergeometric distribution and p-value threshold of 5%. Fisher's exact test (right-tailed) to calculate the probability of a pathway's presence based upon the number of present members and the relative protein levels.

Immunoblotting

Whole cell extracts were prepared from FFPE slides and resolved by SDS-PAGE as described previously[9]. Detection was performed using Western Lightning Plus ECL enhanced chemiluminescent substrate (Perkin-Elmer Inc., #NEL103001EA) according to manufacturer's instructions. For probing, the following antibodies were used: anti-Histone H3 (1:5000; rabbit polyclonal, Abcam, Cambridge, Mass., #ab1791), anti-Histone H3 trimethyl K27 (1:2000; rabbit monoclonal, Cell signaling, Danvers, Mass., #9733). Images were obtained using ImageQuant LAS H3K27me3 is elevated in melanoma 11 4000 imager (GE Healthcare, Pittsburgh, Pa.). The images were obtained as tiff files. Images were obtained using ImageQuant LAS 4000 imager (GE Healthcare, Pittsburgh, Pa.). The images were obtained as a tiff file, and densitometric quantification was performed using the Image J software.

Chromatin Immunoprecipation

Chromatin Immunoprecipatation was performed on FFPE tissues as described previously[9], The ChIP antibodies used were anti-H3 (Abcam, catalog no. ab1791) and anti-H3K27me3 (Cell Signaling, catalog no. 9733). For quantification of enrichment of H3K27me3 (normalized to histone H3) at the E-cadherin promoter, qPCR was performed as described previously[9]. Fold changes were determined using a Mini-Opticon real time PCR detection system (Bio-Rad). The following primers were used for real time analysis: E-CADHERIN promoter region: E-CADHERIN forward (5'-AGAGGGTCACCGCGTCTATG-3') (SEQ ID NO: 1), and E-CADHERIN reverse (5'-TCACAGGTGCTTTGCTGTTC-3') (SEQ ID NO: 2). For normalization: β-actin forward (5'-CTTGGCATC-CACGAAACTA-3') (SEQ ID NO: 3), and β-actin reverse (5-'GAGCCAGAGCAGTGATCTCC-3') (SEQ ID NO: 4)

Statistical Analysis

Protein Arrays

Western Digital Quick Spots Tool was used to process scanned array films. Quick Spots is guided by selecting reference spots and then it automatically averages the duplicate spots based upon the mean pixel intensity and subtracts the pixel intensity of the negative control spots. Next, we summed the mean pixel intensities from each array, grouped by response status and calculated a fold change of responding/non-responding. Ratios >2 were defined as significant. Summation was chosen because median values of some chemokines were 0 due to no signal detected and averages were heavily influenced by wide variation between individual samples. The biological question to answer was which tumor set has more chemokine signaling.

Mass Spectrometry iBAQ intensity values for identified proteins were exported from MaxQuant to an Excel spreadsheet. Prior to statistical analysis, iBAQ values were normalized between sample comparisons using the following process. First, the intensity values for each protein across all patient samples were summed to give a total intensity of the protein. The proteins are then ranked from largest sum intensity to the smallest allowing us to identify the most abundant proteins in the data set. Zero intensity values were replaced by ten times the global non-zero minimum intensity value. This allows us to calculate the Log 2 transformation and perform hypothesis statistical analysis. Next, the summed intensities across all proteins for each patient sample were calculated to generate total protein intensity for each patient. A normalization factor was created by setting the patient sample with the lowest total protein intensity value to 1 and dividing the other patient sum totals by the lowest total protein intensity. Then each of the protein intensities in a patient sample was multiplied by its normalization factor. This allows the patient samples to be normalized for total protein intensity in the data set. Finally, the data was Log 2 transformed to account for heteroscedasticity and subjected to a Student's t-test to exam a null hypothesis of no difference between responding and non-responding tumors.

Proteins with a p-value <0.05 (by Student's T-test) and a fold change greater than 2 were considered to have the most significance (Table 1). Proteins meeting significance criteria are illustrated in a volcano plot (FIG. 2B). 106 proteins found to meet the criteria of p-value <0.05, and fold change >2 were selected for further investigation.

Immunohistochemistry

After immunostaining, an H-score was generated by a dermatopathologist using the following method. A staining percentage was calculated with 4 intensities. The staining percentages were 0-25%, 26-50%, 51-75%, 76-100%. The intensity values were 0 (negative), 1 (weak), 2 (moderate), 3 (strong). Then, the staining percentage was multiplied by the staining intensity resulting in scores from 0-300. A Student's t test was used to test for significant differences between two conditions.

Ordination Analysis

Non-metric multidimensional scaling (NMS) was performed using Bray-Curtis dissimilarities of the iBAQ values for each significant protein from responding and non-responding tumors. Bray-Curtis dissimilarity was selected as the distance measure because it results in less distortion than Euclidean distance, and analyses of quantitative data are less sensitive to outliers[28]. NMS plots were generated using PC-ORD 6.

NMS of protein abundance values produced a two-dimensional ordination (FIG. 2D) with a final stress of 0.00795 (final stress is the significance of difference from a random distribution; scaled here from 0-1). All ordination methods are subject to error when trying to preserve sample to sample relationships as high-dimensional data are being viewed in a lower-dimensional (often 2-D) plot. The simplest indicator of NMS ordination success is the Kruskal's stress value. Stress <0.05 gives excellent representation with no prospect of misinterpretation, stress <0.01 is a good ordination with no real risk of drawing false inferences, stress >0.20 is likely to yield plots dangerous to interpret and stress over 0.35 indicates samples are likely randomly placed[17]. In the plane defined by the two axes of the NMS ordination, triangles representing responding tumors were distant from triangles representing non-responding tumors, plotting high on NMS 1. Using the Pearson r values closest to 1 for NMS axis 1, we were able to identify protein changes which explained the maximal amount of difference between responding and non-responding tumors with the minimal amount of redundancy.

REFERENCES

1. Dunn, G. P., Old, L. J. & Schreiber, R. D. The Three Es of Cancer Immunoediting. *Annu. Rev. Immunol.* 22, 329-360 (2004).
2. Hodi, F. S. et al. Improved Survival with Ipilimumab in Patients with Metastatic Melanoma. *N. Engl. J. Med.* 363, 711-723 (2010).
3. Topalian, S. L. et al. Safety, Activity, and Immune Correlates of Anti-PD-1 Antibody in Cancer. *N. Engl. J. Med.* 366, 2443-2454 (2012).
4. Hamid, O. et al. Safety and Tumor Responses with Lambrolizumab (Anti-PD-1) in Melanoma. *N. Engl. J. Med.* 369, 134-144 (2013).
5. Brown, J. A. et al. Blockade of programmed death-1 ligands on dendritic cells enhances T cell activation and cytokine production. *J. Immunol.* 170, 1257-66 (2003).
6. M, K. D. & Gros, G. Le. The role of CTLA-4 in the regulation of T cell immune responses. *Immunol. Cell Biol.* 77, 1-10 (1999).
7. Larkin, J. et al. Combined Nivolumab and Ipilimumab or Monotherapy in Untreated Melanoma. *N. Engl. J. Med.* 373, 23-34 (2015).
8. Souroullas, G. P. et al. An oncogenic Ezh2 mutation induces tumors through global redistribution of histone 3 lysine 27 trimethylation. *Nat. Med.* 22, 632-40 (2016).
9. Sengupta, D. et al. Quantitative Histone Mass Spectrometry Identifies Elevated Histone H3 Lysine 27 (Lys27) Trimethylation in Melanoma. *Mol. Cell. Proteomics* 15, 765-75 (2016).
10. Snyder, A. et al. Genetic Basis for Clinical Response to CTLA-4 Blockade in Melanoma. *N. Engl. J. Med.* 371, 2189-2199 (2014).
11. Ibrahim, N. et al. A phase I trial of panobinostat (LBH589) in patients with metastatic melanoma. *Cancer Med.* (2016). doi: 10.1002/cam4.862
12. Hugo, W. et al. Genomic and Transcriptomic Features of Response to Anti-PD-1 Therapy in Metastatic Melanoma. *Cell* 165, 35-44 (2016).
13. Tumeh, P. C. et al. PD-1 blockade induces responses by inhibiting adaptive immune resistance. *Nature* 515, 568-71 (2014).
14. Harlin, H. et al. Chemokine expression in melanoma metastases associated with CD8+ T-cell recruitment. *Cancer Res.* 69, 3077-85 (2009).
15. Byrum, S. et al. A quantitative proteomic analysis of FFPE melanoma. *J. Cutan. Pathol.* 38, 933-936 (2011).
16. D. Byrum, S. et al. Quantitative Proteomics Identifies Activation of Hallmark Pathways of Cancer in Patient Melanoma. *J. Proteomics Bioinform.* 6, 43-50 (2013).
17. Clarke, K. R. Non-parametric multivariate analyses of changes in community structure. *Aust. J. Ecol.* 18, 117-143 (1993).
18. Lamouille, S., Xu, J. & Derynck, R. Molecular mechanisms of epithelial-mesenchymal transition. *Nat. Rev. Mol. Cell Biol.* 15, 178-196 (2014).
19. Lupia, A. et al. CD63 Tetraspanin Is a Negative Driver of Epithelial-to-Mesenchymal Transition in Human Melanoma Cells. *J. Invest. Dermatol.* 134, 2947-2956 (2014).
20. Soshnev, A. A., Josefowicz, S. Z. & Allis, C. D. Greater Than the Sum of Parts: Complexity of the Dynamic Epigenome. *Mol. Cell* 62, 681-694 (2016).
21. Sarkar, D., Leung, E. Y., Baguley, B. C., Finlay, G. J. & Askarian-Amiri, M. E. Epigenetic regulation in human melanoma: past and future. doi: 10.1080/15592294.2014.1003746
22. Zingg, D. et al. The epigenetic modifier EZH2 controls melanoma growth and metastasis through silencing of distinct tumour suppressors. *Nat. Commun.* 6, 6051 (2015).
23. Hugo, W. et al. Genomic and Transcriptomic Features of Response to Anti-PD-1 Therapy in Metastatic Melanoma. *Cell* 165, 35-44 (2016).
24. Ji, R.-R. et al. An immune-active tumor microenvironment favors clinical response to ipilimumab. *Cancer Immunol. Immunother.* 61, 1019-1031 (2012).
25. Kreizenbeck, G. M., Berger, A. J., Subtil, A., Rimm, D. L. & Gould Rothberg, B. E. Prognostic significance of cadherin-based adhesion molecules in cutaneous malignant melanoma. *Cancer Epidemiol. Biomarkers Prev.* 17, 949-58 (2008).
26. Wolchok, J. D. et al. Guidelines for the evaluation of immune therapy activity in solid tumors: immune-related response criteria. *Clin. Cancer Res.* 15, 7412-20 (2009).
27. Schwanhausser, B. et al. Global quantification of mammalian gene expression control. *Nature* 473, 337-42 (2011).
28. Beals, E. W. Bray-Curtis Ordination: An Effective Strategy for Analysis of Multivariate Ecological Data. *Adv. Ecol. Res.* 14, 1-55 (1984).

The invention claimed is:

1. A method of treating cancer in a subject comprising administering to the subject a therapeutically effective amount of an immunotherapeutic agent based on the expression level of at least three biomarkers in a tumor sample from the subject; wherein at least three of the biomarkers are selected from CDH1, CXCL4, ILK, LIMIS1, MYLK, PIGR and H3K27me3.

2. The method of claim 1, wherein the biomarkers further comprise at least one biomarker selected from the group consisting of CD63, CXCL12, TPM2, and CREB1.

3. The method of claim 1, wherein the biomarkers further comprise at least one biomarker selected from the group consisting of CD63 and CXCL12.

4. The method of claim 1, wherein the expression levels of at least two five and no more than 25 biomarkers are measured.

5. The method of claim 1, wherein the expression level of the biomarker is the protein expression level.

6. The method of claim 1, wherein the tumor sample is from a melanoma, carcinoma, lung cancer, bladder cancer, or an epithelial cancer.

7. The method of claim 1, wherein the subject is a human patient.

8. The method of claim 1, wherein the immunotherapeutic agent is selected from the group consisting of an cytotoxic T-lymphocyte antigen-4 (CTLA-4) inhibitor, a programmed death-1/programmed death-ligand (PD-1/PD-L) inhibitor, and a T cell immunoglobulin mucin-3 (TIM-3) inhibitor.

* * * * *